United States Patent
Hillson

(10) Patent No.: US 9,361,427 B2
(45) Date of Patent: Jun. 7, 2016

(54) SCAR-LESS MULTI-PART DNA ASSEMBLY DESIGN AUTOMATION

(75) Inventor: Nathan J. Hillson, San Francisco, CA (US)

(73) Assignee: The Regents of the University Of California, Oakland, CA (US)

( * ) Notice: Subject to any disclaimer, the term of this patent is extended or adjusted under 35 U.S.C. 154(b) by 82 days.

(21) Appl. No.: 13/364,285

(22) Filed: Feb. 1, 2012

(65) Prior Publication Data

US 2012/0259607 A1 Oct. 11, 2012

Related U.S. Application Data

(60) Provisional application No. 61/438,601, filed on Feb. 1, 2011.

(51) Int. Cl.
| | | |
|---|---|---|
| G01N 33/48 | (2006.01) | |
| G01N 33/50 | (2006.01) | |
| G06F 19/22 | (2011.01) | |
| G06F 19/16 | (2011.01) | |
| G06F 19/18 | (2011.01) | |
| G06F 19/20 | (2011.01) | |

(52) U.S. Cl.
CPC .............. *G06F 19/22* (2013.01); *G06F 19/16* (2013.01); *G06F 19/18* (2013.01); *G06F 19/20* (2013.01)

(58) Field of Classification Search
None
See application file for complete search history.

(56) References Cited

U.S. PATENT DOCUMENTS

| | | | | |
|---|---|---|---|---|
| 5,858,725 A | * | 1/1999 | Crowe et al. ................. | 435/69.7 |
| 6,458,530 B1 | * | 10/2002 | Morris et al. ................. | 435/6.13 |
| 2002/0058252 A1 | * | 5/2002 | Ananiev ........................... | 435/6 |
| 2002/0164348 A1 | * | 11/2002 | Kirkegaard et al. ........ | 424/186.1 |
| 2006/0269922 A1 | * | 11/2006 | Sagner et al. .................... | 435/6 |

OTHER PUBLICATIONS

Lee et al. A functional analysis of the spacer of V(D)J recombination signal sequences. PLoS Biology, 2003, 11 pages.*
Homologous. Merrian-Webster Dictionary, 2013, 6 pages. Obtained online on May 6, 2013 from <<http://www.merriam-webster.com>>.*
Li et al. Harnessing homologous recombination in vitro to generate recombinant DNA via SLIC. Nature Methods, vol. 4, 2007, pp. 251-256.*
Hillson et al. j5 DNA assembly design automation software. ACS Synthetic Biology, Dec. 7, 2011, vol. 1, pp. 14-21.*
Gibson (2009) Enzymatic assembly of DNA molecules up to several hundred kilobases. *Nature Meth.*, 6: 343-345.
Quan and Tian (2009) Circular Polymerase Extension Cloning of Complex Gene Libraries and Pathways. *PLoS ONE*, 4(7): e6441.
Vector NTI Advance 11 manual—Dated Dec. 15, 2008.
Vector NTI Advance 11.5 manual—Dated Jan. 12, 2011.
Zhang et al. (2012) SLiCE: a novel bacterial cell extract-based DNA cloning method. *Nucleic Acids Res.* 40(8): e55.
Gibson et al., "Enzymatic assembly of DNA molecules up to several hundred kilobases (supplemental materials)," Nat. Meth., vol. 6, No. 5, May 2009, pp. 343-347.
Ramon et al., "Single-step linker-based combinatorial assembly of promoter and gene cassettes for pathway engineering," Biotechnol. Lett. 33, 2011, pp. 549-555.

* cited by examiner

*Primary Examiner* — Russell S Negin
(74) *Attorney, Agent, or Firm* — Tom Hunter; Weaver Austin Villeneuve & Sampson LLP

(57) ABSTRACT

The present invention provides a method of a method of designing an implementation of a DNA assembly. In an exemplary embodiment, the method includes (1) receiving a list of DNA sequence fragments to be assembled together and an order in which to assemble the DNA sequence fragments, (2) designing DNA oligonucleotides (oligos) for each of the DNA sequence fragments, and (3) creating a plan for adding flanking homology sequences to each of the DNA oligos. In an exemplary embodiment, the method includes (1) receiving a list of DNA sequence fragments to be assembled together and an order in which to assemble the DNA sequence fragments, (2) designing DNA oligonucleotides (oligos) for each of the DNA sequence fragments, and (3) creating a plan for adding optimized overhang sequences to each of the DNA oligos.

76 Claims, 89 Drawing Sheets

Fig. 27A

Non-degenerate Part IDs and Sources

| Part ID Number | Name | Source Plasmid | Location Reverse Complement | Start (bp) | End (bp) | Size (bp) | Sequence |
|---|---|---|---|---|---|---|---|
| 0 | pES119_SbfI_AscI_vector_fragment | pES119 | FALSE | 7965 | 4382 | 8529 | CGCGCCTTCC |
| 1 | atfA_3prime | pES119 | FALSE | 4383 | 4701 | 319 | GGACTCAACA |
| 2 | BBa_B1002_term | BBa_B1002 | FALSE | 1 | 34 | 34 | CGCAAAAAAC |
| 3 | lacUV5_lacO | pBbE5a-RFP | FALSE | 1449 | 1579 | 131 | CCTGTGGCGC |
| 4 | EcoRI_mutation | pES119 | FALSE | 4769 | 4769 | 1 | A |
| 5 | pdc_without_3prime_end | pES119 | FALSE | 4769 | 6237 | 1469 | AATTCAAAGG |
| 6 | pdc_3prime_and_adhB | pES119 | FALSE | 6238 | 7704 | 1467 | TGATGGTCCG |
| 7 | BBa_B1006_term | BBa_B1006 | FALSE | 1 | 39 | 39 | AAAAAAAAAC |
| 8 | ITetA_5prime | pES119 | FALSE | 7770 | 7964 | 195 | AATTCAAAGG |

Fig. 27B

Target Part Ordering/Selection/Strategy

| Part Order | ID Number | Name | Orientation | Strategy |
|---|---|---|---|---|
| 0 | 0 | pES119_SbfI_AscI_vector_fragment | forward | DIGEST |
| 1 | 1 | atfA_3prime | forward | PCR |
| 2 | 2 | BBa_B1002_term | forward | Embed_in_primer_reverse |
| 3 | 3 | lacUV5_lacO | forward | SOE |
| 4 | 4 | EcoRI_mutation | forward | Embed_in_primer_reverse |
| 5 | 5 | pdc_without_3prime_end | forward | PCR |
| 6 | 6 | pdc_3prime_and_adhB | forward | PCR |
| 7 | 7 | BBa_B1006_term | forward | Embed_in_primer_reverse |
| 8 | 3 | lacUV5_lacO | forward | SOE |
| 9 | 4 | EcoRI_mutation | forward | Embed_in_primer_reverse |
| 10 | 8 | ITesA_5prime | forward | SOE |

Fig. 28

| Oligo Synthesis ID Number | Name | First Target | Last Target | Length | Tm | Tm (3' only) | Cost | Sequence |
|---|---|---|---|---|---|---|---|---|
| 0 | NJH08001_(atfA_3prime)_pure_forward | 1 | 1 | 26 | 55.703 | 55.703 | 2.6 | GGACTCAACA |
| 1 | NJH08002_(atfA_3prime)_forward | 1 | 1 | 52 | 71.429 | 55.703 | 5.2 | ATAGTGCTGT |
| 2 | NJH08003_(atfA_3prime)_pure_reverse | 1 | 1 | 26 | 51.003 | 51.003 | 2.6 | ATCCTTAATT |
| 3 | NJH08004_(atfA_3prime)_(BBa_B1002_term)_reverse | 1 | 2 | 73 | 79.039 | 51.003 | 47.3 | CCGGCGCCA |
| 4 | NJH08005_(lacUV5_lacO)_pure_forward | 3 | 3 | 18 | 60.561 | 60.561 | 1.8 | CCTGTGGCG |
| 5 | NJH08006_(lacUV5_lacO)_forward | 3 | 3 | 31 | 71.378 | 60.561 | 3.1 | GCGGTTTTT |
| 6 | NJH08007_(lacUV5_lacO)_pure_reverse | 3 | 3 | 30 | 60.122 | 60.122 | 3 | TGAAATTGTT |
| 7 | NJH08008_(lacUV5_lacO)_(EcoRI_mutation)_reverse | 3 | 4 | 44 | 62.252 | 60.122 | 4.4 | CTTCCTTTGA |
| 8 | NJH08009_(pdc_without_3prime_end)_pure_forward | 3 | 5 | 26 | 55.978 | 55.973 | 2.6 | AATTCAAAGG |
| 9 | NJH08010_(pdc_without_3prime_end)_forward | 5 | 5 | 48 | 67.649 | 55.973 | 4.8 | TGTGAGCGG |
| 10 | NJH08011_(pdc_without_3prime_end)_pure_reverse | 5 | 5 | 26 | 56.655 | 56.655 | 2.6 | TCGATCATAA |
| 11 | NJH08012_(pdc_without_3prime_end)_reverse | 5 | 5 | 45 | 68.089 | 56.655 | 4.5 | GTTGTTGTTAC |
| 12 | NJH08013_(pdc_3prime_and_adhB)_pure_forward | 6 | 6 | 31 | 62.232 | 62.232 | 3.1 | TGATGGTCCG |
| 13 | NJH08014_(pdc_3prime_and_adhB)_forward | 6 | 6 | 44 | 67.026 | 62.232 | 4.4 | AAGTTATGAT |
| 14 | NJH08015_(pdc_3prime_and_adhB)_pure_reverse | 6 | 6 | 36 | 63.896 | 63.896 | 3.6 | AGATCCTTAG |
| 15 | NJH08016_(pdc_3prime_and_adhB)_(BBa_B1006_term)_reverse | 6 | 7 | 88 | 79.73 | 63.896 | 48.8 | CCGGCGCCA |
| 16 | NJH08005_(lacUV5_lacO)_pure_forward | 8 | 8 | 18 | 60.561 | 60.561 | 0 | CCTGTGGCG |
| 17 | NJH08017_(lacUV5_lacO)_forward | 8 | 8 | 31 | 68.631 | 60.561 | 3.1 | CCGGTTTTT |
| 18 | NJH08007_(lacUV5_lacO)_pure_reverse | 8 | 8 | 30 | 60.122 | 60.122 | 0 | TGAAATTGTT |
| 19 | NJH08008_(lacUV5_lacO)_(EcoRI_mutation)_reverse | 8 | 9 | 44 | 65.252 | 60.122 | 0 | CTTCCTTTGA |
| 20 | NJH08018_(fTesA_5prime)_pure_forward | 10 | 10 | 34 | 61.372 | 61.372 | 3.4 | AATTCAAAGG |
| 21 | NJH08019_(fTesA_5prime)_forward | 10 | 10 | 56 | 69.666 | 61.372 | 5.6 | TGTGAGCGGA |
| 22 | NJH08020_(fTesA_5prime)_pure_reverse | 10 | 10 | 23 | 61.914 | 61.914 | 2.3 | CCAGTCCTTG |
| 23 | NJH08021_(fTesA_5prime)_reverse | 10 | 10 | 53 | 79.201 | 61.914 | 5.3 | GATGCTGTT |

Fig. 29A

PCR/SOE Reactions

| ID Number | Primary Template | Alternative Template | Forward Oligo Name | Forward Oligo ID | Reverse Oligo Name | Reverse Oligo ID | First Target | Last Target | Note | Mean Oligo Tm | Δ Oligo Tm | Mean Oligo Tm (3') | Δ Oligo Tm (3') | Length | Amplified sequence |
|---|---|---|---|---|---|---|---|---|---|---|---|---|---|---|---|
| 0 | pES119 | | NJH00001 | 0 | NJH00002 | 2 | 1 | 1 | PCR | 53.353 | 4.7 | 53.353 | 4.7 | 319 | GGACTGAACA |
| 1 | pBbE5a-RFP | | NJH00003 | 4 | NJH00006 | 6 | 3 | 3 | SOE | 60.3415 | 0.439 | 60.3415 | 0.439 | 131 | CCTGTGCGGC |
| 2 | pES119 | | NJH00005 | 8 | NJH00010 | 10 | 5 | 5 | PCR | 56.3165 | 0.677 | 56.3165 | 0.677 | 1469 | AATTCAAAGG |
| 3 | pES119 | | NJH00009 | 12 | NJH00011 | 14 | 6 | 6 | PCR | 63.064 | 1.664 | 63.064 | 1.664 | 1467 | TGATGGTCCG |
| 4 | pBbE5a-RFP | | NJH00013 | 16 | NJH00014 | 18 | 8 | 8 | SOE | 60.3415 | 0.439 | 60.3415 | 0.439 | 131 | CCTGTGCGGC |
| 5 | pES119 | | NJH00005 | 20 | NJH00002 | 2 | 10 | 10 | SOE | 61.643 | 0.542 | 61.643 | 0.542 | 195 | AATTCAAAGG |
| 6 | PCR/SOE Reaction 0 | pES119 | NJH00002 | 1 | NJH00003 | 3 | 1 | 2 | PCR | 75.234 | 7.61 | 53.353 | 4.7 | 392 | ATAGTGGTGT |
| 7 | PCR/SOE Reaction 1 | pBbE5a-RFP | NJH00006 | 5 | NJH00007 | 7 | 3 | 4 | SOE | 68.315 | 6.126 | 60.3415 | 0.439 | 188 | GCGGTTTTTT |
| 8 | PCR/SOE Reaction 2 | pES119 | NJH00010 | 9 | NJH00011 | 11 | 5 | 5 | PCR | 67.929 | 0.36 | 56.3165 | 0.677 | 1510 | TGTGACGGGA |
| 9 | PCR/SOE Reaction 3 | pES119 | NJH00013 | 13 | NJH00015 | 15 | 6 | 7 | PCR | 73.378 | 12.704 | 63.064 | 1.664 | 1532 | AAGTTATGAT |
| 10 | PCR/SOE Reaction 4 | pBbE5a-RFP | NJH00014 | 17 | NJH00019 | 19 | 8 | 9 | SOE | 66.9415 | 3.379 | 60.3415 | 0.439 | 188 | CCGGGTTTTT |
| 11 | PCR/SOE Reaction 5 | pES119 | NJH00019 | 21 | NJH00023 | 3 | 10 | 10 | SOE | 74.4535 | 9.935 | 61.643 | 0.542 | 247 | TGTGACGGGA |

Fig. 29B

Non-degenerate Part IDs and Sources

| Part ID Number | Name | Source Plasmid | Location Reverse Complement | Start (bp) | End (bp) | Size (bp) | Sequence |
|---|---|---|---|---|---|---|---|
| 0 | pES119_ShfI_AscI_vector_fragment | pES119 | FALSE | 7963 | 4382 | 8520 | CGCGCCTTCC |
| 1 | afA_3prime | pES119 | FALSE | 4383 | 4701 | 319 | GGACTCAACA |
| 2 | BBa_B1002_term | BBa_B1002 | FALSE | 1 | 34 | 34 | CGCAAAAAAC |
| 3 | lacUV5_lacO | pbbE5a-RFP | FALSE | 1449 | 1579 | 131 | CCTTGTTGCGC |
| 4 | EcoRI_mutation | pES119 | FALSE | 4769 | 4769 | 1 | A |
| 5 | pdc_without_3prime_end | pES119 | FALSE | 4769 | 6237 | 1469 | AATTCAAAGG |
| 6 | pdc_3prime_and_adhB | pES119 | FALSE | 6238 | 7704 | 1467 | TGATGGTCCG |
| 7 | BBa_B1006_term | BBa_B1006 | FALSE | 1 | 39 | 39 | AAAAAAAAC |
| 8 | TesA_5prime | pES119 | FALSE | 7770 | 7964 | 195 | AATTCAAAGG |

SCAR-LESS MULTI-PART DNA ASSEMBLY DESIGN AUTOMATION

RELATED APPLICATIONS

This application claims priority to U.S. Provisional Patent Application Ser. No. 61/438,601, filed Feb. 1, 2011, which is hereby incorporated by reference in its entirety.

STATEMENT OF GOVERNMENT SUPPORT

This invention was made with government support under Contract No. DE-AC02-05CH11231 awarded by the U.S. Department of Energy. The government has certain rights in this invention.

FIELD OF THE INVENTION

The present invention relates to the field of DNA assembly, and particular relates to a method of designing an implementation of a DNA assembly.

BACKGROUND OF THE INVENTION

A challenge in the field of DNA assembly is to take a set of double-stranded DNA sequence fragments, and stitch them together in the proper order and proper orientation to yield a single, potentially circular, assembled DNA sequence. These DNA sequence fragments are often referred to as "parts" in the synthetic biology lexicon, especially when the fragments are each associated with a particular biological function, such as a promoter, a coding sequence, a terminator, etc. For the purposes of j5, "parts" simply refer to generalized DNA sequences.

Prior art FIG. 1A depicts a prior art DNA assembly. The DNA assembly starts with 8 non-degenerate (non-repeated) composite biological parts (shown at the bottom of the figure): a vector backbone, 5 protein coding sequences (orfA to orfE) with upstream ribosome binding sites (RBS), a terminator, and a promoter. These 8 parts are assembled into the target expression vector, shown at the top of FIG. 1A. Note that in this particular example, the same terminator and promoter parts were used twice to achieve the target expression vector.

PRIOR ART

For a recent review on the many available experimental methodologies for addressing this challenge, see Ellis[1].

Multiple Cloning Site Approach

One prior art DNA assembly technique is the multiple cloning site, restriction enzyme, ligase cloning approach.

Prior art FIG. 1B depicts a typical expression destination vector designed with the prior art multiple cloning site, restriction enzyme, ligase cloning approach.

In this specific example, a multiple cloning site (MCS) follows a T7 promoter, and is in turn followed by a T7 terminator. If a researcher wants to integrate a protein coding sequence of interest into this expression vector, he or she: 1) identifies two restriction sites present in the MCS, but absent in the coding sequence of interest, 2) PCR amplifies the coding sequence of interest with DNA oligo primers flanked with the selected restriction sites, 3) digests the PCR product as well as the destination vector with the corresponding restriction enzymes, 4) gel-purifies the digested PCR product and the destination vector backbone, 5) ligates the purified digested PCR product and destination vector, and 6) transforms the resulting ligation reaction into competent E. coli.

This approach works well for integrating a single coding sequence into the MCS of the destination expression vector. The large number of multiple cloning sites (11 in the example shown above) results in a high likelihood that at least two of the sites will be absent from the coding sequence of interest. However, as soon as we would like to incorporate multiple DNA sequence fragments into the same destination vector, such as an entire metabolic pathway or genetic circuit, as shown in the previous DNA assembly example, the odds are less on our side. Now, we must find as many distinct restriction sites (or resulting overhang sequences, to be more precise; with sequential sites absent from the DNA fragment they flank) as the number of DNA fragments to be assembled (including the destination vector), and two of these (flanking the linearized destination vector) must be present in the MCS. In the previous DNA assembly example, with 10 fragments total (the terminator and promoter were each used twice), we would need 10 restriction sites with distinct resulting overhang sequences, including two from the MCS, with the corresponding requirement that each is absent from its flanking assembly fragments. Generally speaking, it becomes increasingly unlikely that this constraint will be met with each additional sequence fragment to be assembled.

Molecular biologists have tackled this recurring obstacle with various strategies. A non-exhaustive set of examples includes: adding (silent) point mutations to DNA fragments to disrupt restriction site sequences, splicing together two or more fragments with PCR (e.g. splicing by overlap extension (SOE)), using compatible single-stranded overhangs that (when ligated) do not result in a recognizable/recleavable restriction site, partial DNA digests, annealing single stranded DNA fragments to yield double stranded DNA with the desired single stranded overhangs, site specifically protecting a methyl-sensitive restriction enzyme site from methylation with a DNA oligo/RecA complex, sequentially performing the assembly hierarchically (so that the same restriction site may potentially be used more than once; however, this makes downstream cloning and re-use more difficult), and the list goes on and on. It should be explicitly pointed out here that direct DNA synthesis, while perhaps cost-prohibitive at the moment (although certainly less so in the near future), is a very viable alternative to DNA assembly in general, and has the capacity to make many of these obstacles and concerns obsolete. We will return to direct DNA synthesis during the brief survey of j5 functionality.

The BioBrick, SLIC, Gibson, CPEC and Golden-gate DNA assembly methods utilize, or are derived from, many of these modifications to the multiple cloning site method. What sets these methods apart from the traditional approach is "standardization". In traditional cloning, the set of selected restriction enzymes (as well as the point mutations made to disrupt undesired replicate restriction sites) is entirely dependent on the number, sequences and order of the fragments to be assembled. Thus, every different assembly might require a different combination of restriction enzymes, point mutations, reaction temperature and buffer conditions. Furthermore, a given sequence fragment may have to be re-cloned entirely for each new assembly, precluding re-use. While restriction enzyme companies (such as NEB and Fermentas), have made much progress in ensuring that all of their restriction enzymes can operate under a single reaction condition (temperature, buffer, etc.), in general, it is very unlikely that a single enzymatic "master mix" can be applied across independent traditional assemblies, making the process less amenable to parallelization and automation (especially via high-throughput liquid handling robotics platforms). The BioBrick, SLIC/Gibson/CPEC and Golden-gate methods, in contrast, use the same (standardized) set of enzymes and reaction conditions for every assembly. When point mutations are required (as is potentially the case for BioBrick and Golden-gate assembly, which utilize restriction enzyme(s)), the same mutations are required for every assembly, and thereby each sequence fragment only needs to be cloned once, facilitating re-use. Thus, these standardized methods are much more amenable to parallelization and automation than the traditional approach.

BioBrick Approach

Another prior art DNA assembly technique is the BioBrick approach. BioBricks standardize the DNA assembly process, facilitating automation and part re-use. There are several BioBrick assembly standards, such as that originally developed at MIT (See Shetty[2].), as well as the UC Berkeley BglBrick standard (See Anderson[3].), which is depicted in FIG. 1C.

Prior art FIG. 1C depicts a prior art BglBrick assembly of partA, partB, and the partA-bearing vector backbone. In the BglBrick standard, a part (or DNA sequence fragment that is nominally associated with a biological function) is flanked with two restriction enzyme sites at its 5' end, namely EcoRI and BglII and is flanked with BamHI and XhoI at its 3' terminus. To comply with the BglBrick standard, these four restriction sites must be absent from the sequence of the part itself. The "BglBrick", then, spans from the EcoRI to the XhoI site, and the BioBrick-bearing vector backbone makes up the residual plasmid sequence, which should also be devoid of the four BglBrick restriction sites. To assemble partA followed by partB, followed by the partA-bearing vector backbone, the partA BglBrick vector is digested with BamHI and XhoI, and the partB vector is digested with BglII and XhoI. The resulting digest fragments containing partA and partB are then ligated together, resulting in the desired plasmid. The overhang sequences resulting from BamHI and BglII digest are complementary (base-pair/anneal perfectly with one-another), but the resulting ligation product sequence is not recognized/recleaved by either BamHI or BglII. Thus, the assembly results in a new BglBrick, containing partA followed by a six bp scar sequence, followed by partB. A key consequence of BglBrick assembly is that assembling two parts results in a new BglBrick, so that this process can be iterated successively to assemble an arbitrary number of parts together, using the same protocol repetitively. It is possible to assemble partB in front of partA, and/or to select the partA or partB-bearing vector backbone for the resulting construct, by using different combinations of the four BglBrick restriction enzymes. Other BioBrick standards are completely analogous to BglBricks, and simply use alternate sets of the four restriction enzymes.

Contrasting with the traditional approach, there are several advantages to using BioBricks: 1) only four restriction enzymes are utilized, 2) once a part is BioBrick'd, it is never necessary to re-clone it (or even re-PCR amplify it, reducing the probability of PCR-derived mutations), and 3) assembling an arbitrary number of parts (in any desired arrangement) is no more difficult than putting two together (plasmid size considerations aside). It should be highlighted that, in contrast with SLIC, Gibson, CPEC and Golden-gate methods, BioBrick assembly not only standardizes the assembly process (e.g. the set of four restriction enzymes, protocols, etc.), but also physically standardizes the BioBrick'd parts themselves, as they all have the same 5' and 3' terminal sequences, and internally share the same 6-bp scar vestiges of prior assemblies. There are burgeoning repositories of these standardized parts (physical and/or informatic), such as the MIT Registry of Standard Biological Parts, and supporting organizations, such as the BioBricks Foundation, that allow and facilitate researcher re-use of characterized and validated parts, preempting wasteful redundant efforts.

Prior art FIG. 1D depicts how the prior art BioBrick approach could be used to assemble a pathway. Note that there are many different possible routes (assembly trees) to put together this pathway using BioBricks. Some of the intermediate parts, such as the terminator fused to the promoter, need only be made once, and can be re-used multiple times. Recently, algorithms have been developed (See Densmore[4].) to optimize the design of binary BioBrick assembly trees, and the development of an automated in vivo BglBrick assembly process utilizing liquid-handling robotics is currently underway.

BioBrick Limitations and Obstacles

Despite the many merits of the BioBrick approach, there are some drawbacks. First, there is no control over the existence and sequence of the 6-bp scars resulting from each binary BioBrick assembly. While in many cases, these scars will not prove problematic, there are scenarios where the scar sequences, affecting coding sequences or mRNA secondary structure, can adversely perturb the desired protein, RBS, terminator, etc., function. Second, unless every intermediate part is archived along the binary assembly tree, it is necessary to repeat the entire process from scratch in order to replace a composite part (e.g. orfC in the example above) in the assembled BioBrick; even if all intermediate parts are archived, many of the steps must still be repeated. Third, combinatorial library diversity generation is potentially at odds with the BioBrick assembly process, because diversity must be recaptured after each and every binary assembly step (which requires aggregating 5 times as many post-transformation colonies per binary assembly as the sequence diversity to be retained), Fourth, BioBrick assembly only works with previously BioBrick'd parts, and another cloning method must be used to first create the BioBricks to be assembled.

Given the availability of design tools for BioBrick assembly, and a forth-coming automated in-vivo BioBrick assembly methodology, j5 does not design BioBrick assembly, but instead designs for the SLIC, Gibson, CPEC and Golden-gate methods, which address the short comings of the BioBrick approach, and retain compatibility with the established BioBrick standard(s) (i.e. the methods employed by j5 can be used to assemble BioBrick vectors, although not using BioBrick assembly to do so).

SLIC, Gibson and CPEC Assembly Methods

Prior art DNA assembly methods SLIC, Gibson, and CPEC are related methods that offer standardized, scarless, (largely) sequence-independent, multi-part DNA assembly. Some discussion of the advantages of each method over the others is provided below.

SLIC

Prior art SLIC, or sequence and ligase independent cloning (See Li[5].), as its name implies, does not utilize restriction enzymes or ligase. A DNA sequence fragment to be cloned into a destination vector is PCR amplified with oligos whose 5' termini contain about 25 bp of sequence homology to the ends of the destination vector, linearized either by restriction digest or PCR amplification. Sequence homology regions are depicted in white and grey in prior art FIG. 1E.

Prior art FIG. 1E depicts a prior art SLIC assembly of partA with a linearized destination vector. The linearized destination vector and the PCR product containing partA are separately treated with T4 DNA polymerase in the absence of dNTPs. In the absence of dNTPs, T4 DNA polymerase has 3' exonuclease activity, which begins to chew-back the linearized destination vector and the PCR product from 3' to 5'. Once the termini of the linearized destination vector and the PCR product have sufficient complementary single-stranded 5' overhangs exposed, dCTP is added to arrest the chew-back reaction. With the addition of dCTP, the T4 DNA polymerase changes activity from 3' exonuclease to polymerase, but stalls because not all dNTPs are present, retaining most, if not the entirety, of each chewed-hack overhang. Alternatives to the 3' chew-hack with T4 DNA polymerase in the absence of dNTPs include the use of mixed or incomplete PCR products (so this does not apply to the linearized vector backbone if it is derived from a restriction enzyme digest), which can also result in the desired 5' overhangs, as described in the original SLIC publication (See Li[5].). The chewed-back linearized destination vector and PCR product are mixed together, and annealed to each other. Since there is no ligase in the reaction, this results in a plasmid with four single stranded gaps or nicks. Once transformed into competent *E. coli*, the gaps are repaired. Note that SLIC assembly is standardized, in that it always uses the same reaction components and conditions, scar-less, since there is no sequence in the resulting assembly that is not user-designed, and sequence-independent, as the method is not (at least to a large extent, but see below) sensitive to the sequences of either the destination vector or the part to be incorporated.

Gibson

Prior art Gibson DNA assembly, so named after the developer of the method (See Gibson[6].), is analogous to SLIC, except that it uses a dedicated exonuclease (no dNTP addition step), and uses a ligase to seal the single stranded nicks.

Prior art FIG. 1F depicts Gibson assembly of partA with a linearized destination vector. The linearized destination vector and the PCR product containing partA are mixed together with T5 exonuclease, which chews-back the linearized destination vector and the PCR product from 5° to 3', Phusion polymerase, which (with the annealed linearized destination vector and PCR product effectively priming each other) fills in the gaps, and ligase, which seals the four single stranded nicks. The polymerase chases the exonuclease around the plasmid, with the polymerase eventually overtaking, as the exonuclease is gradually heat-inactivated (and Phusion is extremely fast). Like SLIC, Gibson assembly is standardized, scar-less, and largely sequence-independent. Gibson is advantageous over SLIC in that it is a simultaneous one pot reaction (the two-step addition of dCTP is not required), the presence of ligase may boost assembly efficiency, and since the assembly reaction occurs at an elevated temperature relative to SLIC, there may be fewer problems when somewhat stable secondary structures occur at the ends of assembly pieces; the disadvantage of the Gibson method is that the T5 exonuclease, Phusion polymerase, and Taq ligase cocktail is more expensive than that required for SLIC (only T4 DNA polymerase, or none at all if mixed or incomplete PCR products are used). An anecdotal/empirical limitation of the Gibson method is that it works best to assemble DNA fragments that are at least 250 bp in length or longer; this is perhaps due to the likelihood that the 15 exonuclease would entirely chew through a short DNA fragment before it has a chance to anneal and prime the Phusion polymerase for extension. While the same could be said for SLIC, the timing of dCTP addition provides some control in switching from the exonuclease to the polymerase activity of T4 DNA polymerase (the use of mixed or incomplete PCR products can prevent this problem all together), although caution should be applied when using SLIC to assemble small DNA fragments. Prior to Gibson (or SLIC) assembly, it is recommended to SOE (splice by overlap extension) together neighboring assembly fragments until their cumulative size is larger than 250 bp. Fortunately, the very same PCR products designed for Gibson (and SLIC) assembly, already contain the flanking homology sequences required for SOEing.

CPEC

Prior art CPEC, or circular polymerase extension cloning (See Quan[7].), is analogous to SOEing together the fragments to be assembled, except that no oligos are utilized (the linearized destination vector and PCR product prime each other, as in SLIC/Gibson assembly) and there are typically only a few thermo-cycles required.

Prior art FIG. 1G depicts CPEC assembly of partA with a linearized destination vector. Since there are no (or very few) re-amplifications of a given template sequence, PCR-derived mutations are not propagated to the same extent as one would anticipate for standard SOEing reactions. Like SLIC and Gibson assembly, CPEC is standardized, scar-less, and largely sequence-independent. CPEC is advantageous in that, since there is no exonuclease chew-back, small sequence fragments can be assembled directly without a preliminary SOEing step, there is no (ATP addition step (unlike SLIC), there is only a single enzyme (polymerase) required (unlike Gibson), and since the CPEC assembly reaction occurs at higher temperatures than either SLIC or Gibson, stable secondary structures at the ends of assembly pieces are relatively less of a concern. The main disadvantages of CPEC is that it is more likely to result in polymerase-derived mutations than SLIC or Gibson, and mis-priming events are now possible anywhere along the sequences of the fragments to be assembled (as opposed to only at the termini of the fragments), although the Gibson method, depending on how much of a head start the T5 exonuclease has, could suffer from similar drawbacks.

SLIC/Gibson/CPEC Similarities

Despite their differences in implementation, SLIC, Gibson, and CPEC assembly methods all start with the same starting materials and result in the same final products, a shown in prior art FIG. 1H. Thus, an assembly designed for CPEC will be equally applicable to SLIC or Gibson assembly.

Prior art FIG. 1I depicts how SLIC/Gibson/CPEC assembly could be used to put together the pathway. In this example, each homology region is color-coded, from red to violet, in an analogous fashion to the white and grey homology region coloring in the previous single part SLIC/Gibson/CPEC examples above. It should be noted that with SLIC/Gibson/CPEC, unlike BioBrick assembly, we can put together many parts at the same time in the same pot (multi-part assembly). Consequences of multi-part, in contrast with hierarchical binary BioBrick, assembly is that we have immediate access to each and every part to be assembled, and with only one transformation step, combinatorially generated diversity is captured a single time. As shown in this example, we can use SLIC/Gibson/CPEC assembly to generate a BioBrick (Bgl-Brick) vector, although since we didn't use BioBrick assembly during the construction process, we did not introduce any undesirable scar sequences. The downside of SLIC/Gibson/CPEC assembly is that we must now design the 5' flanking homology sequence of each oligo specifically for each assembly junction, a process that can be tedious, laborious, and error-prone.

SLIC/Gibson/CPEC Limitations and Obstacles

A major limitation to prior art SLIC/Gibson/CPEC assembly is that the termini of the DNA sequence fragments to be assembled should not have stable single stranded DNA secondary structure, such as a hairpin or a stem loop (as might be anticipated to occur within a terminator sequence), as this would directly compete with the required single-stranded annealing/priming of neighboring assembly fragments. To some extent, it may be possible to mitigate this by padding these problematic termini with sequence from their neighboring assembly fragments. Repeated sequences (such as the repeated terminators and promoters in the example above are often obstacles to SLIC/Gibson/CPEC assembly, since assembly is directed by sequence homology, and if two distinct assembly fragments are identical at one terminus (such as the 3' termini of the terminators in the example above), this can lead to assemblies that do not contain all of the desired parts, or may contain parts arranged in the wrong order. To circumvent these obstacles, which j5 refers to as assembly fragment incompatibilities, it is often necessary to perform a sequential hierarchical assembly so as not to place assembly fragments with identical termini in the same assembly reaction at the same time. When ever possible, it is highly preferred to substitute repeated sequences with sequence pairs that are not identical, yet encode comparable biological function; this provides a benefit not only to the DNA assembly process, but will also enhance the DNA stability of the resulting construct. Finally, SLIC/Gibson/CPEC might not be the optimal choice for combinatorial assembly if sequence diversity occurs at the very ends of the sequence fragments to be assembled (within about 15 bps of the termini), since this will preclude the reuse of the same homology sequences throughout all of the combinations. However, in certain situations, combinatorial SLIC/Gibson/CPEC assembly can be a very reasonable and effective choice (See for example Ramon[8].), if the sequence identity throughout all combinations and assembly junctions is extensive enough not to be a limitation. These limitations, which assert that the SLIC/Gibson/CPEC assembly methods are not completely sequence-independent, are largely addressed by the Golden-gate assembly method.

Golden-Gate Assembly Method

The prior art Golden-gate method (See Engler[9] and Engler[10].) offers standardized, quasi-scarless, multi-part DNA assembly, and is an excellent choice for combinatorial library construction, The prior art Golden-gate method relies upon the use of type IIs endonucleases, whose recognition sites are distal from their cut sites. Although there are several different type IIs endonucleases to choose from, the example below uses BsaI (equivalent to Eco31I) (the Golden-gate method only uses a single type IIs endonuclease at time).

Prior art FIG. 1J depicts prior art Golden-gate assembly of partA with a linearized destination vector. The BsaI recognition sequence "GGTGTC" is separated from its four by overhang by a single bp, and BsaI activity is independent of the sequences of the single by spacer and the four by overhang. The recognition site for BsaI is not palindromic, and is therefore directional. In the notation used here, the recognition site is abstractly represented by a rectangle below the dsDNA line (with an arrowhead on the bottom segment of the rectangle pointing to the cut site), and the four by overhang sequence is represented by a colored box (with different colors indicating different 4 by sequences). Using this notation, the PCR product containing partA in the example above is flanked by two BsaI recognition sites, both pointing inward towards partA, with a red overhang at its 5' terminus and a blue overhang at its 3' end. The linearized destination vector is similarly depicted. If the PCR product shown above is mixed with BsaI and ligase, the PCR product is (reversibly) digested, resulting in three DNA fragments (the squiggly line abstractly representing the double-stranded cut), and ligated back together again. The same is true of the linearized destination vector. However, if the PCR product and the linearized destination vector (each of which contains one red and one blue 4 bp overhang) are both mixed together with BsaI and ligase, as shown, the cut linearized destination vector will irreversibly ligate (dead-end reaction product) with the cut PCR product containing partA. This particular ligation is irreversible, because the ligation product no longer contains any BsaI recognition sequences. Thus, over time, all reactions will tend towards the desired assembly product. It should be pointed out that the sequences of the of red and blue 4 bp overhangs are (almost) entirely user-specifiable. In this regard, Golden-gate assembly is scar-less, since we have complete control over the sequence of the resulting assembly product. There are some exceptions to this (such as the overhang sequences themselves must not be palindromic (or they would be self-complimentary), and any two (e.g. the red and the blue) overhang sequences must differ by at least one and preferably two bps so that the different overhangs are not cross-complimentary), but in general this is not an issue, because we can shift the relative overhang position (see the target part order list documentation for more details) and still end up with a scar-less assembly. It should be pointed out that the original Golden-gate method calls for the assembly using uncut plasmids, in contrast with the PCR products, and a PCR-linearized destination vector, shown in FIG. 1J (See Engler[9] and Engler[10].). The proposed benefit of using uncut plasmids as the source material is that it is easier to control the assembly stoichiometry, and with each of the plasmid substrates sequence verified and without the use of PCR, accumulating PCR-derived point mutations is not a concern. The limitation of using uncut plasmids as the source material is that the destination vector, and all of the parts to be assembled, must already be cloned into a Golden-gate format plasmid system, and the overhang sequences are set in stone. While PCR amplifying the destination vector backbone and the parts to assembly may result in PCR-derived point mutations, using PCR products as the Golden-gate assembly source material provides the freedom to use any destination vector, and any parts to be assembled into it, without an initial round of cloning that locks in the overhang sequences. One additional point is that for optimal performance of Golden-gate assembly, the linearized destination vector and the part to be incorporated should lack any additional BsaI recognition sites, other than those explicitly depicted in the example above. Since the digestion/ligation reaction is reversible for any internal BsaI recognition sites, it is generally not obligatory to make (silent) point mutations to remove them, however it is usually preferable to do so to maximize efficiency, and to assure that the internal overhang sequences will not anneal to the designed overhangs, and lead to incorrect assemblies.

Prior art FIG. 1K depicts how prior art Golden-gate assembly could be used to put together the pathway. In this example, each 4 bp overhang is color-coded, from red to violet, in an analogous fashion to the red and blue overhang coloring in the previous single part example above (the BsaI recognition sites, while present and inwardly facing in all of the sequence fragments to be assembled, are not depicted here). As is true of SLIC/Gibson/CPEC assembly, we can put together many parts at the same time in the same pot (multi-part assembly), and consequently Golden-gate assembly provides immediate access to each and every part to be assembled, and with only one transformation step, combinatorially generated diversity is captured a single time. As shown in this example, and as is the case for SLIC/Gibson/CPEC assembly, we can use Golden-gate assembly to generate a BioBrick (BglBrick) vector, and since we didn't use BioBrick assembly during the construction process, we did not introduce any undesirable scar sequences. The downside of Golden-gate assembly (as for SLIC/Gibson/CPEC) is that we must now design the 4-bp overhang sequences for each assembly junction and incorporate them into the 5' flanking sequence of each oligo, a process that can be tedious, laborious, and error-prone.

Golden-gate assembly is a particularly good choice for constructing combinatorial libraries. As shown in the example below, every part in each combinatorial bin (the linearized destination vector is the first bin, the red, orange and yellow parts the second, and the purple, blue and green parts are the third) is flanked by the same two 4-hp overhang sequences.

Prior art FIG. 1L depicts how prior art Golden-gate assembly could be use to put together a combinatorial library. Any two parts in a bin are completely interchangeable with respect to Golden-gate assembly, and only a single pair of oligos is required for each part across the entire assembly. Since the same 4 bp overhang sequences are used throughout a combinatorial bin, it is optimal to place the overhangs in sequence regions that are identical across all of the DNA fragments in the bin. If there are no 4-bp stretches of sequence identity at the termini of the bin's sequence fragments, the combinatorial Golden-gate assembly will result in scars (between 1 and 4 bp in length). Even so, this is far superior to BioBrick assembly that always results in 6 bp scar sequences, and very preferable to SLIC/Gibson/CPEC assembly which, while potentially scarless if all sequences have about 15 bp of sequence identity at their termini, will either result in longer scar sequences, or require many more oligos per combinatorial part to achieve a comparable sear length.

Golden Gate Limitations and Obstacles

Perhaps the most significant limitation of the Golden-gate method is that it is less sequence-independent than SLIC/Gibson/CPEC, in the sense that, like BioBrick assembly, the selected type IIs recognition site (e.g. BsaI) should be absent from the internal portions of all of the DNA fragments to be assembled. However, like BioBrick assembly, once the modifications are made to remove these sites, they never have to be remade. In addition, since the overhangs are only 4 bp in length, and we would like at least 1 and preferably 2 bp to be different between each and every overhang in an assembly reaction, it may not be possible to find a set of overhangs that are compatible with each other that allows for a single multi-part assembly step, especially if the number of fragments to assemble together becomes large (greater than about 10 fragments), or if the % GC content of the fragment termini is highly skewed to one extreme or the other. While rarely necessary in practice, in these circumstances, it is possible to do a hierarchical Golden-gate assembly.

Therefore, a method of designing an implementation of a DNA assembly is needed

SUMMARY OF THE INVENTION

The present invention provides a method of a method of designing an implementation of a DNA assembly. In an exemplary embodiment, the method includes (1) receiving a list of DNA sequence fragments to be assembled together and an order in which to assemble the DNA sequence fragments, (2) designing DNA oligonucleotides (oligos) for each of the DNA sequence fragments, and (3) creating a plan for adding flanking homology sequences to each of the DNA oligos. In an exemplary embodiment, the method includes (1) receiving a list of DNA sequence fragments to be assembled together and an order in which to assemble the DNA sequence fragments, (2) designing DNA oligonucleotides (oligos) for each of the DNA sequence fragments, and (3) creating a plan for adding optimized overhang sequences to each of the DNA oligos.

BRIEF DESCRIPTION OF THE DRAWINGS

FIG. 27A and FIG. 27B show data in accordance with the present invention.
In FIG. 27A, sequence for ID Number 0 is SEQ ID NO:1, sequence for ID Number 1 is SEQ ID NO:2, sequence for ID Number 2 is SEQ ID NO:3, sequence for ID Number 3 is SEQ ID NO:4, sequence for ID Number 5 is SEQ ID NO:5, sequence for ID Number 6 is SEQ ID NO:6, sequence for ID Number 7 is SEQ ID NO:7, and sequence for ID Number 8 is SEQ ID NO:8.
FIG. 28 shows data in accordance with the present invention. Sequence for ID Number 0 is SEQ ID NO:9, sequence for ID Number 1 is SEQ ID NO:10, sequence for ID Number 2 is SEQ ID NO:11, sequence for ID Number 3 is SEQ ID NO:12, sequence for ID Number 4 is SEQ ID NO:13, sequence for ID Number 5 is SEQ ID NO:14, sequence for ID Number 6 is SEQ ID NO:15, sequence for ID Number 7 is SEQ ID NO:16, sequence for ID Number 8 is SEQ ID NO:17, sequence for ID Number 9 is SEQ ID NO:18, sequence for ID Number 10 is SEQ ID NO:19, sequence for ID Number 11 is SEQ ID NO:20, sequence for ID Number 12 is SEQ ID NO:21, sequence for ID Number 13 is SEQ ID NO:22, sequence for ID Number 14 is SEQ ID NO:23, sequence for ID Number 15 is SEQ ID NO:24, sequence for ID Number 16 is SEQ ID NO:25, sequence for ID Number 17 is SEQ ID NO:26, sequence for ID Number 18 is SEQ ID NO:27, sequence for ID Number 19 is SEQ ID NO:28, sequence for ID Number 20 is SEQ ID NO:29, sequence for ID Number 21 is SEQ ID NO:30, sequence for ID Number 22 is SEQ ID NO:31, sequence for ID Number 23 is SEQ ID NO:32.

FIG. 29A and FIG. 29B show data in accordance with the present invention. In FIG. 29A, amplified sequence for ID Number 0 is SEQ ID NO:33, amplified sequence for ID Number 1 is SEQ ID NO:34, amplified sequence for ID Number 2 is SEQ ID NO:35, amplified sequence for ID Number 3 is SEQ ID NO:36, amplified sequence for ID Number 4 is SEQ ID NO:37, amplified sequence for ID Number 5 is SEQ ID NO:38, amplified sequence for ID Number 6 is SEQ ID NO:39, amplified sequence for ID Number 7 is SEQ ID NO:40, amplified sequence for ID Number 8 is SEQ ID NO:41, amplified sequence for ID Number 9 is SEQ ID NO:42, amplified sequence for ID Number 10 is SEQ ID NO:43, amplified sequence for ID Number 11 is SEQ ID NO:44. In FIG. 29B, sequence for ID Number 0 is SEQ ID NO:1, sequence for ID Number 1 is SEQ ID NO:2, sequence for ID Number 2 is SEQ ID NO:3, sequence for ID Number 3 is SEQ ID NO:4, sequence for ID Number 5 is SEQ ID NO:5, sequence for ID Number 6 is SEQ ID NO:6, sequence for ID Number 7 is SEQ ID NO:7, and sequence for ID Number 8 is SEQ ID NO:8.

DETAILED DESCRIPTION OF THE INVENTION

Figure 1A:
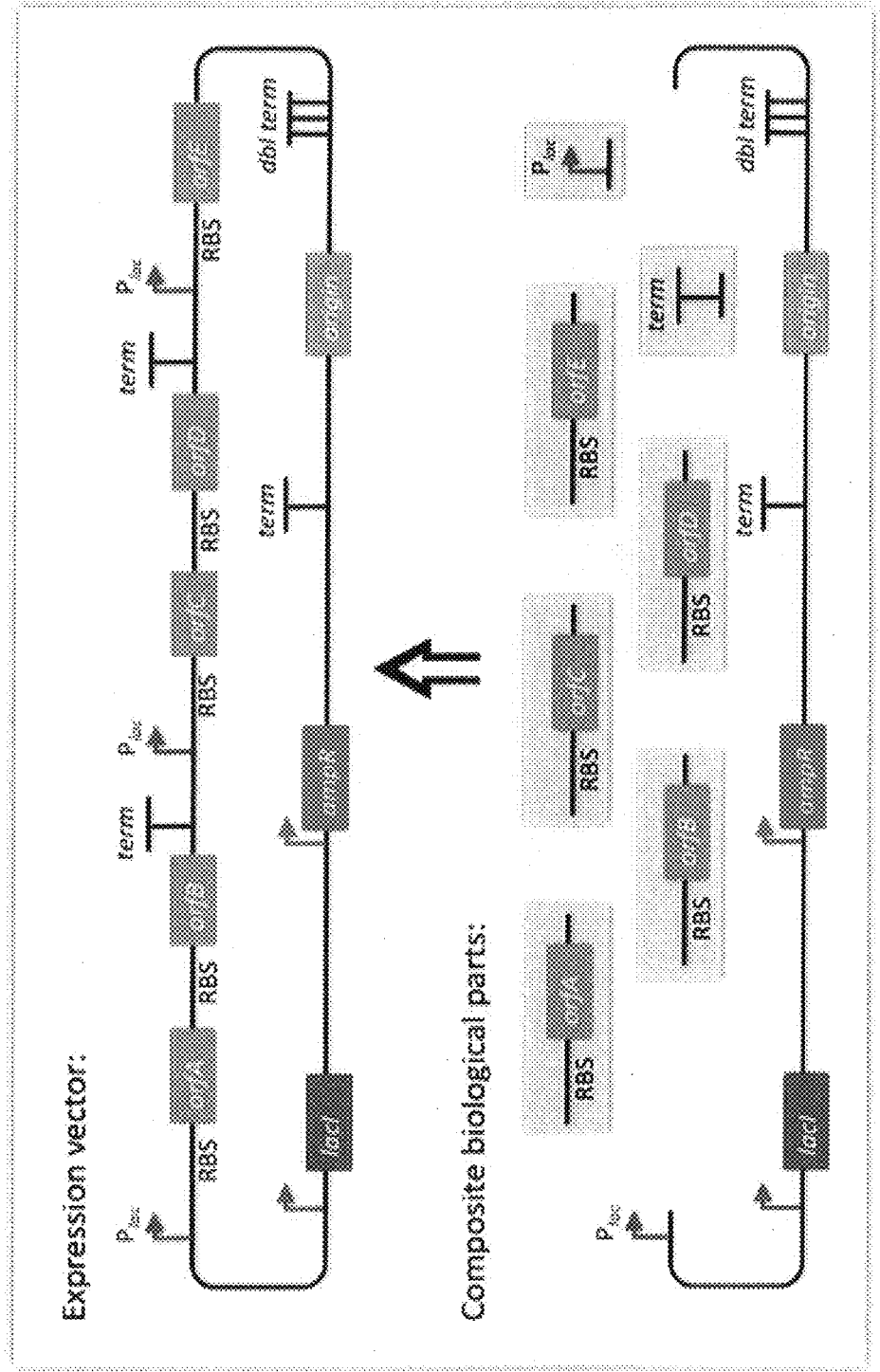
FIG. 1A-1L illustrate prior art systems.
Figure 1B:
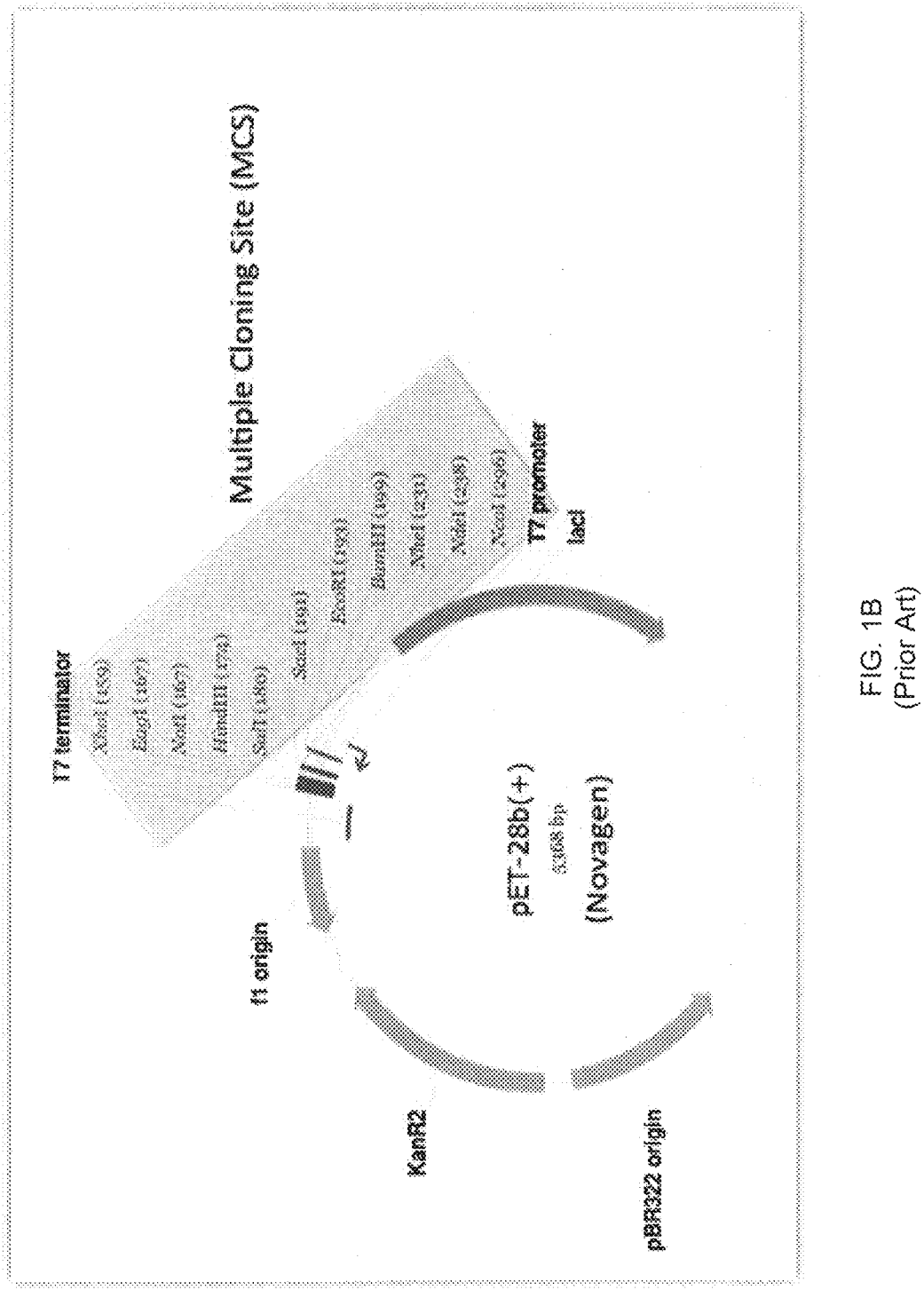
Figure 1C:
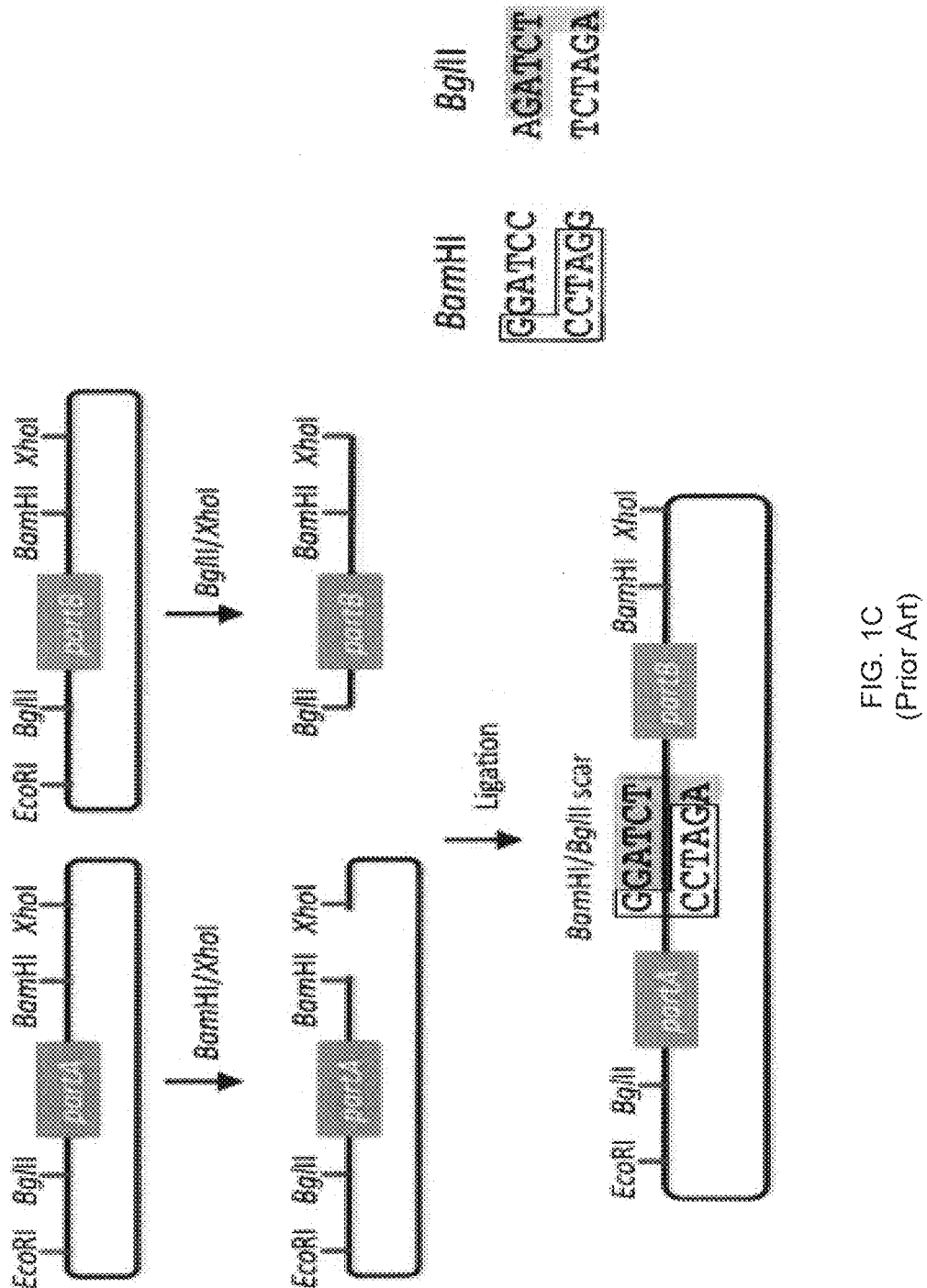
Figure 1D:
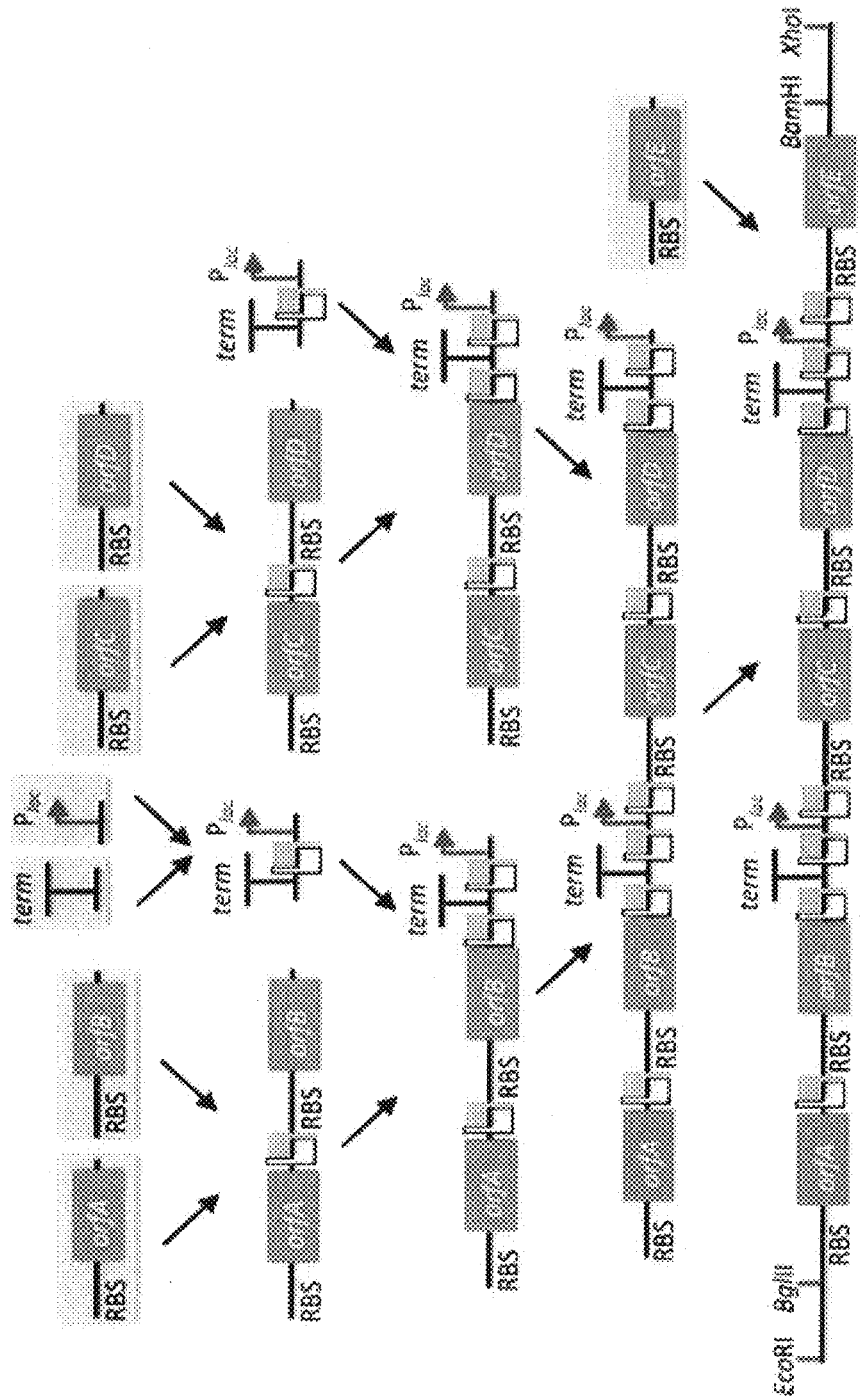
Figure 1E:
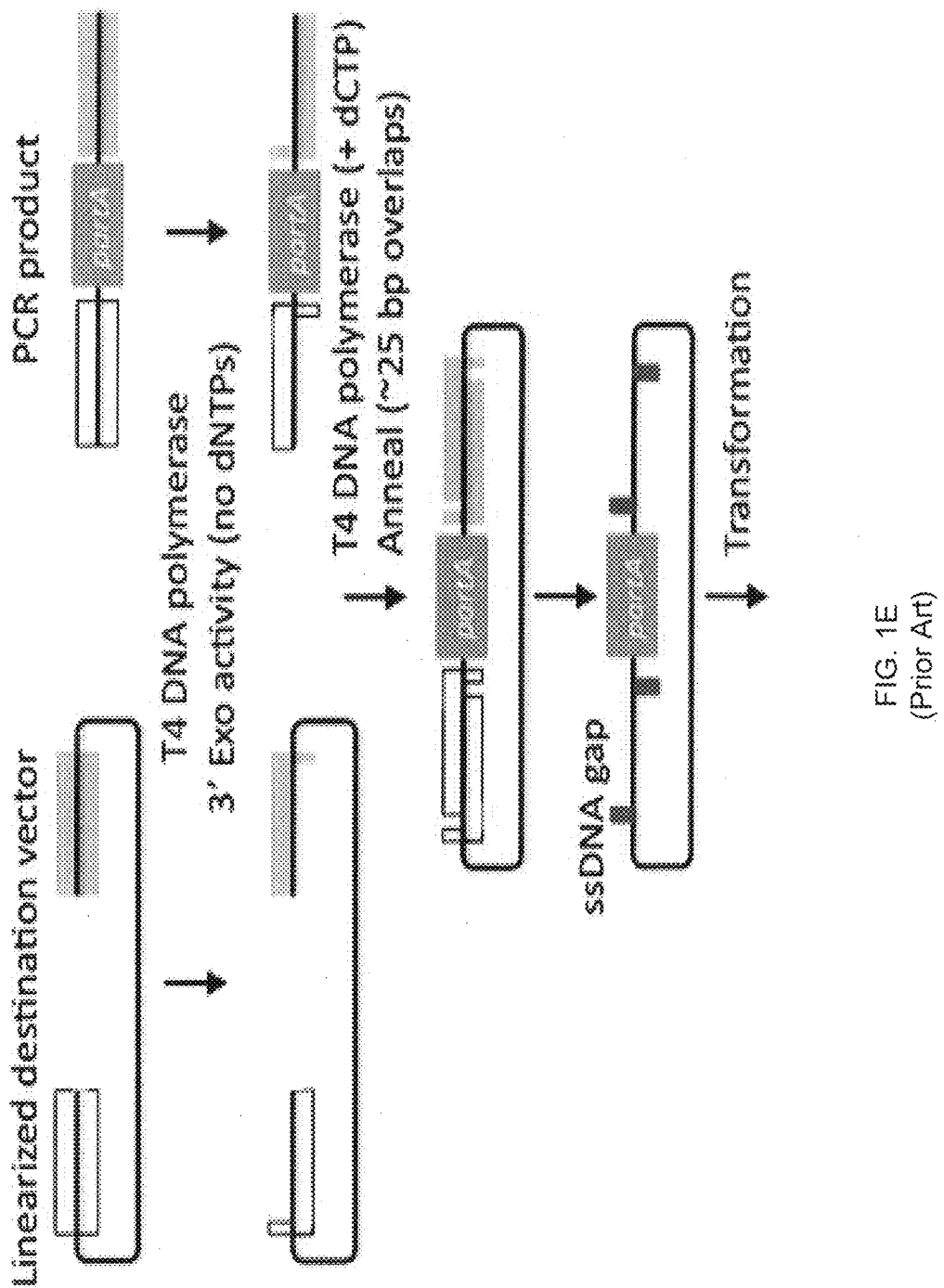
Figure 1F:
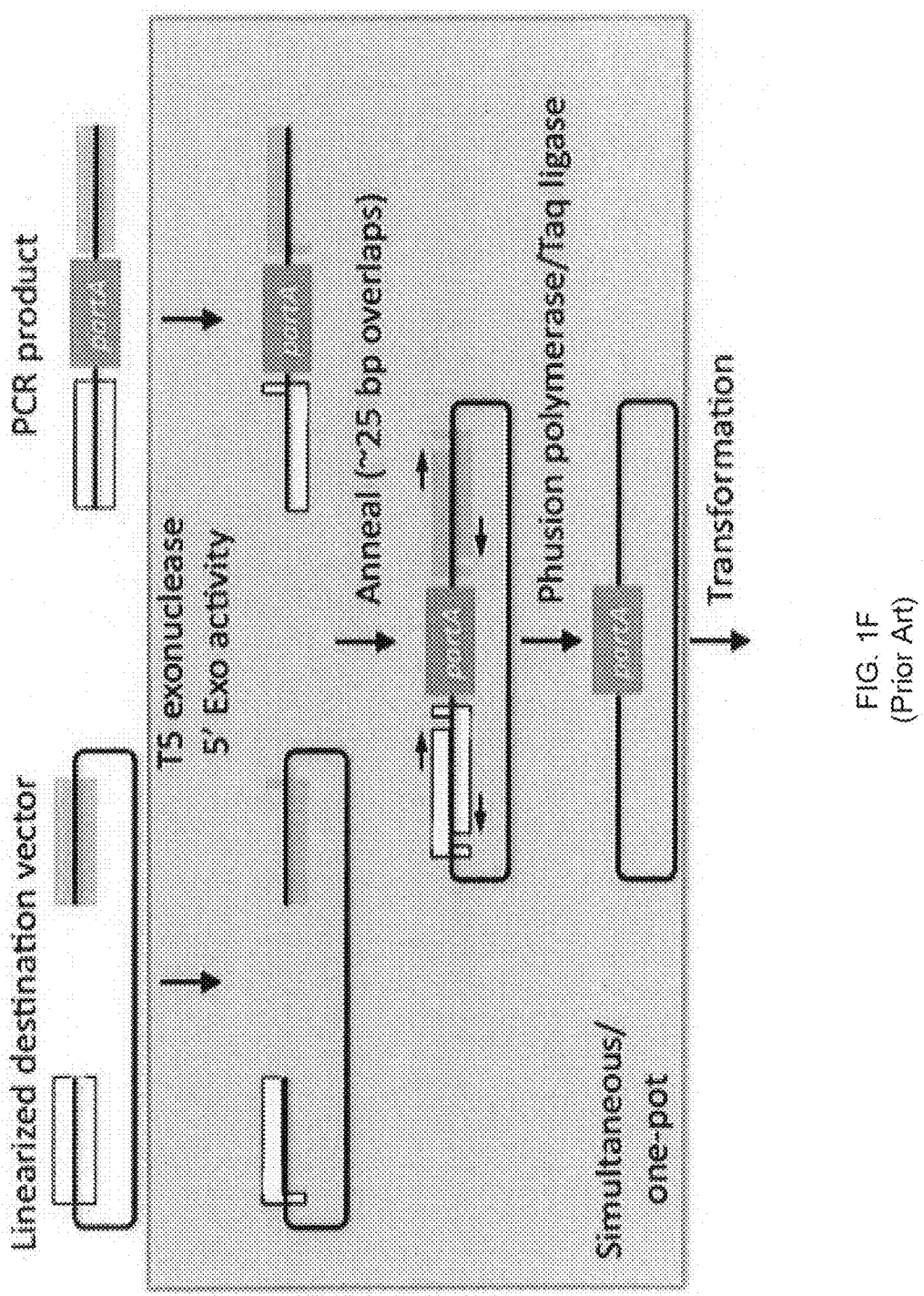
Figure 1G:
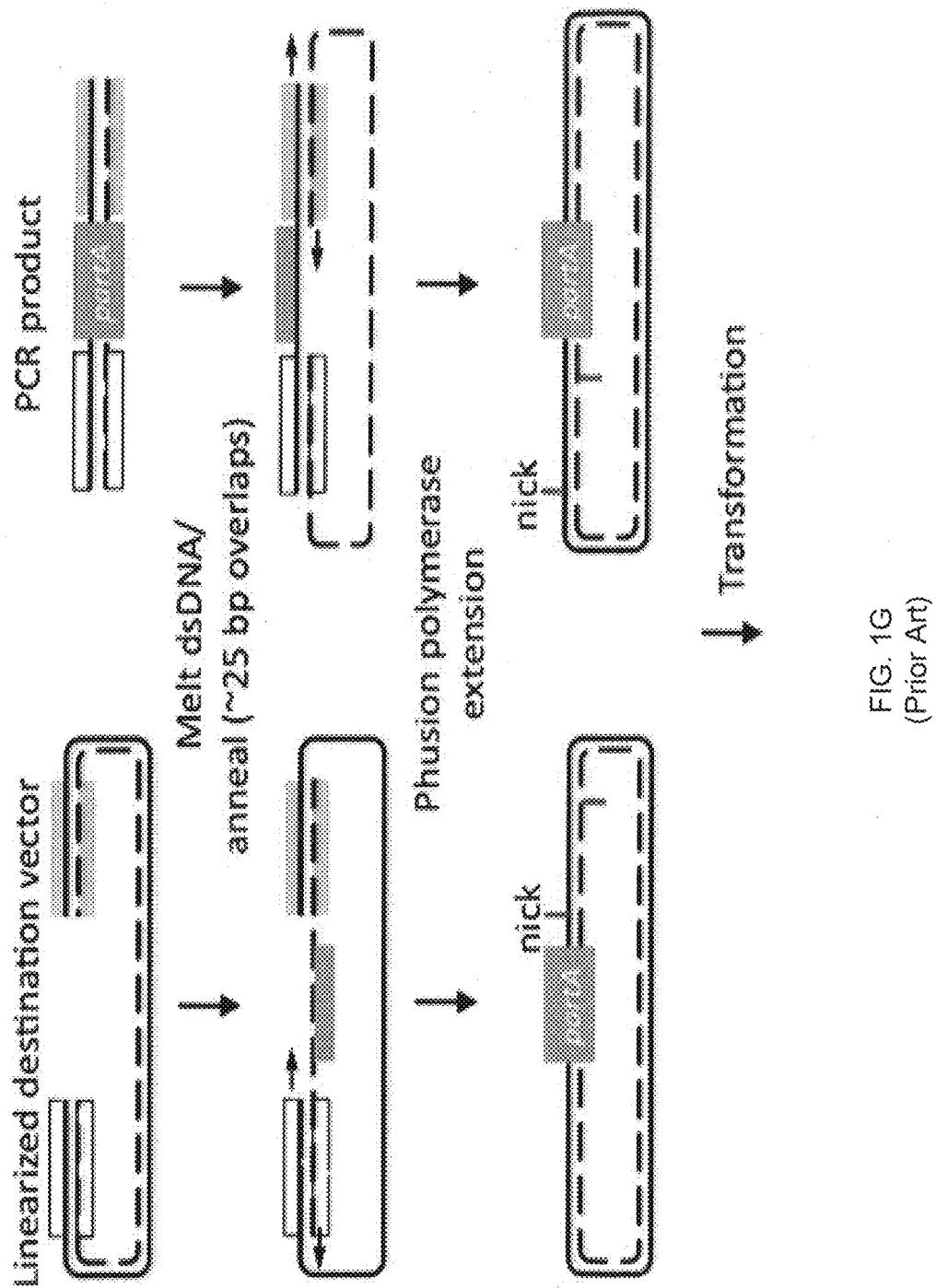
Figure 1H:
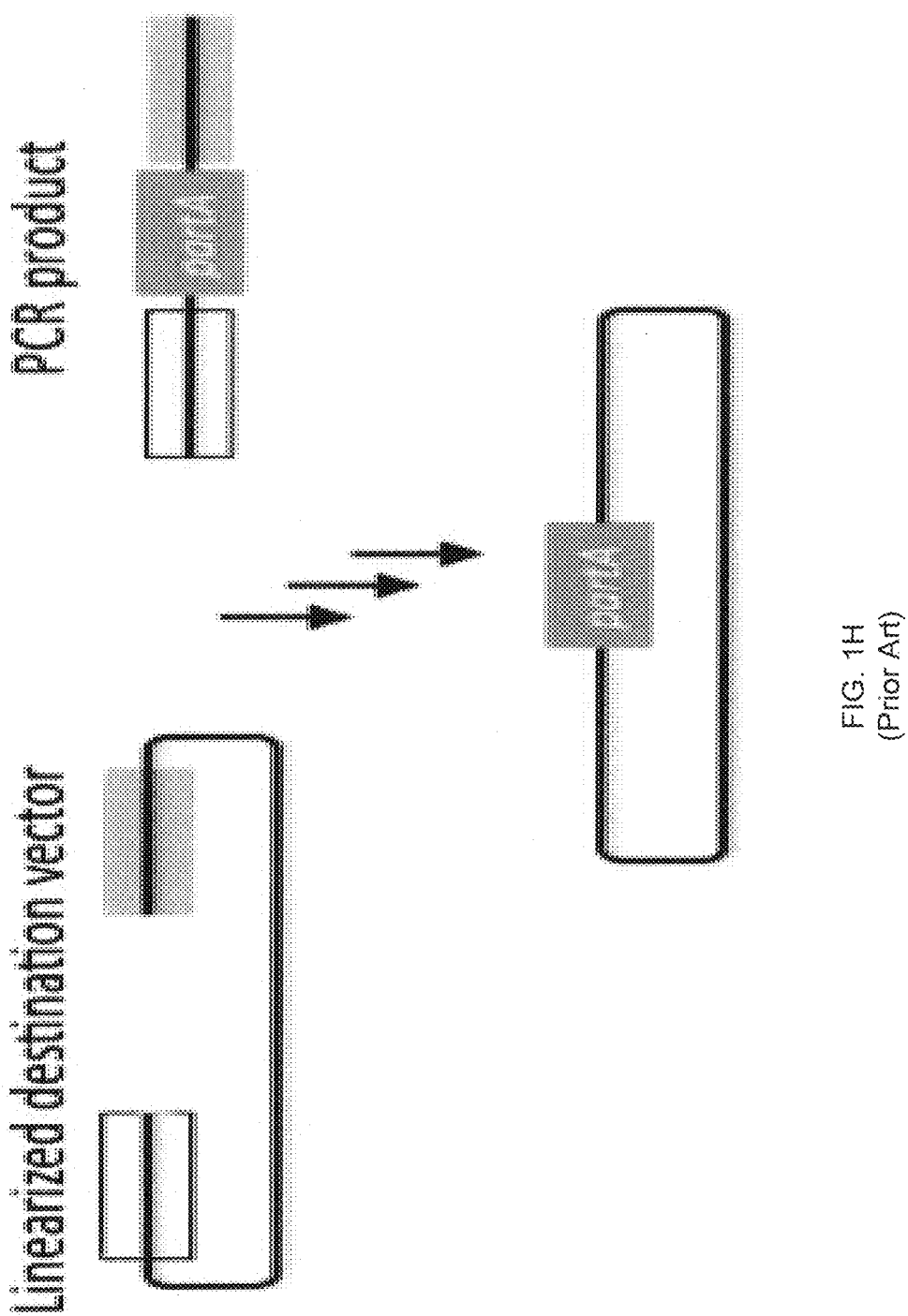
Figure 1I:
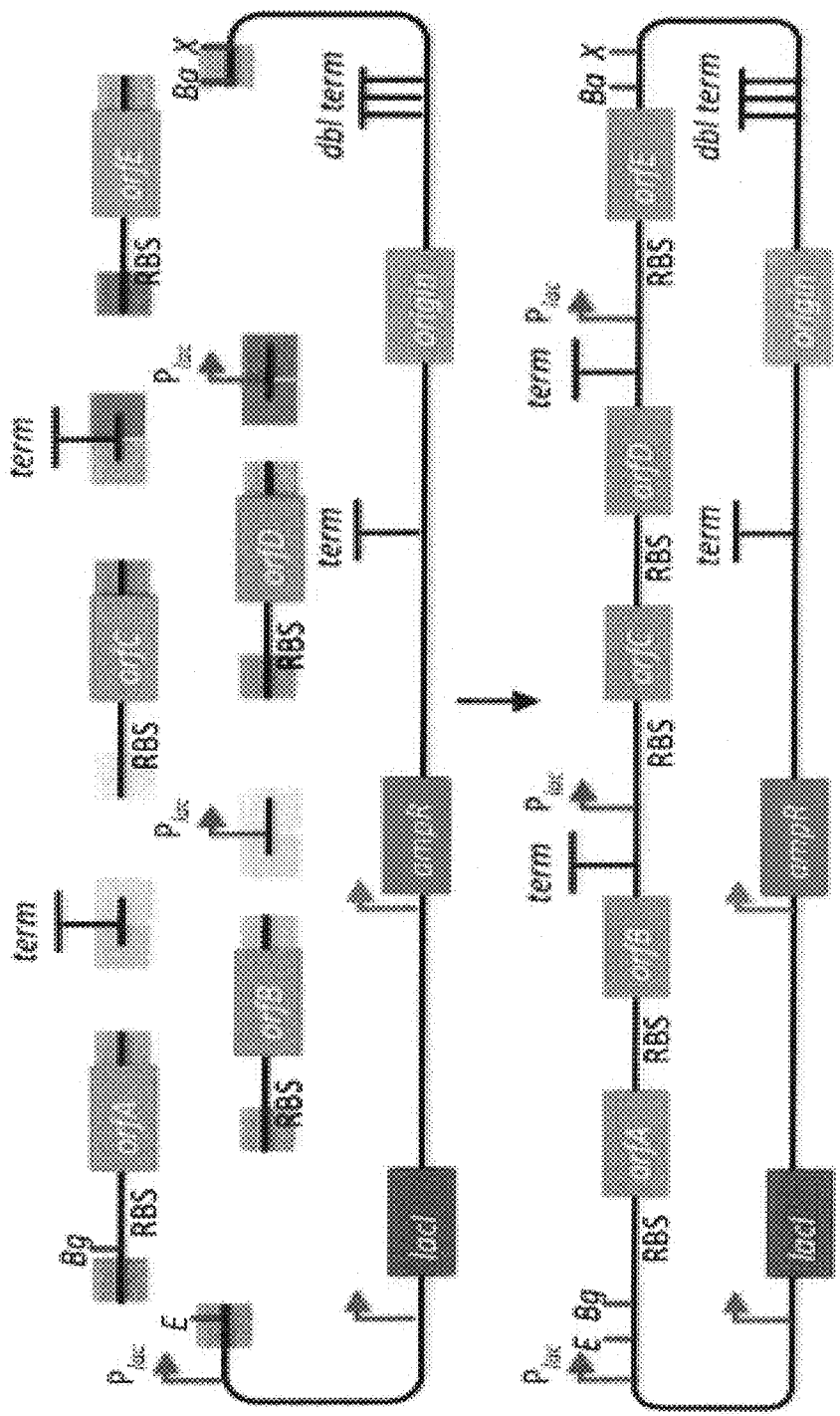
Figure 1J:
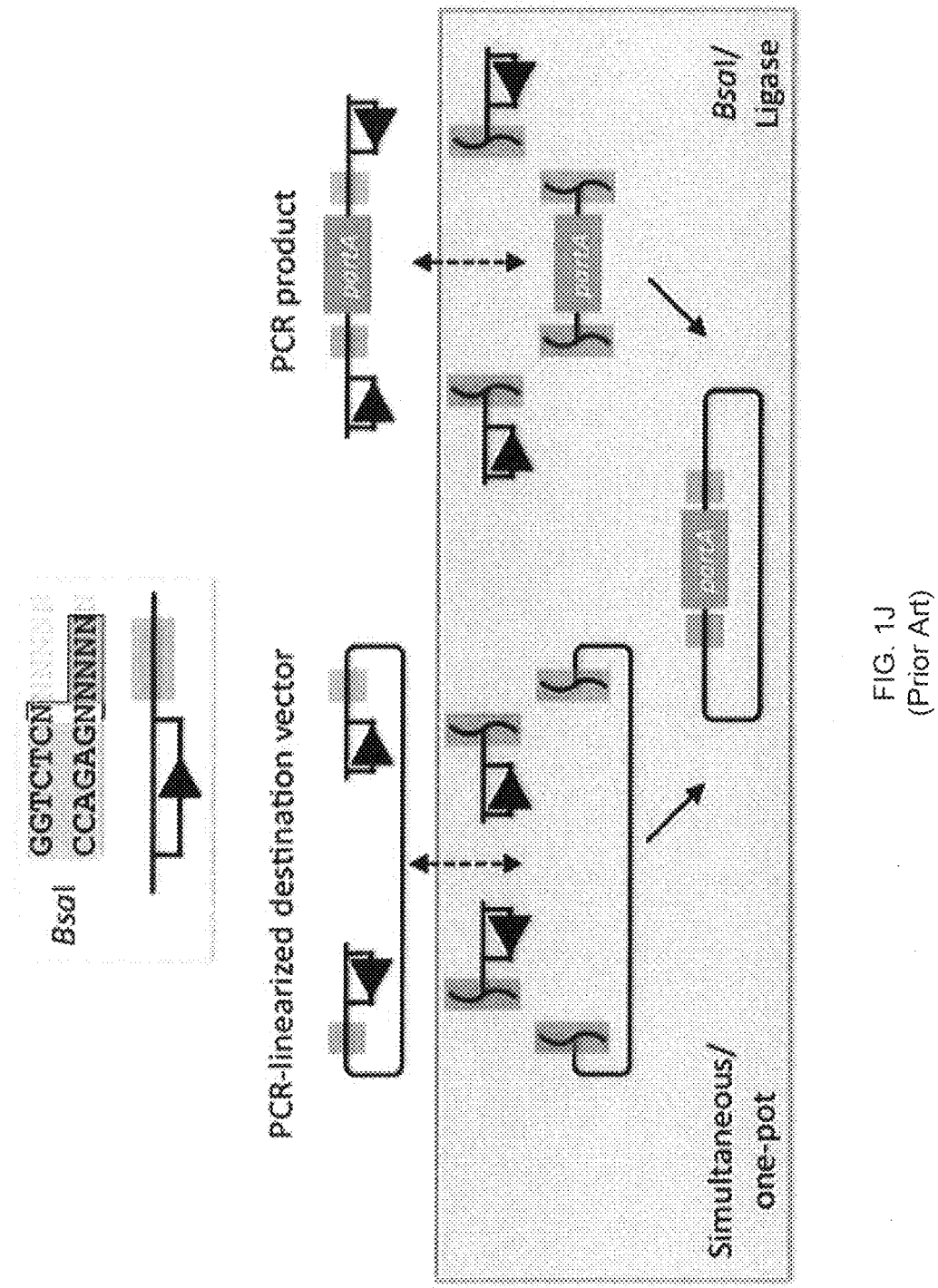
Figure 1K:
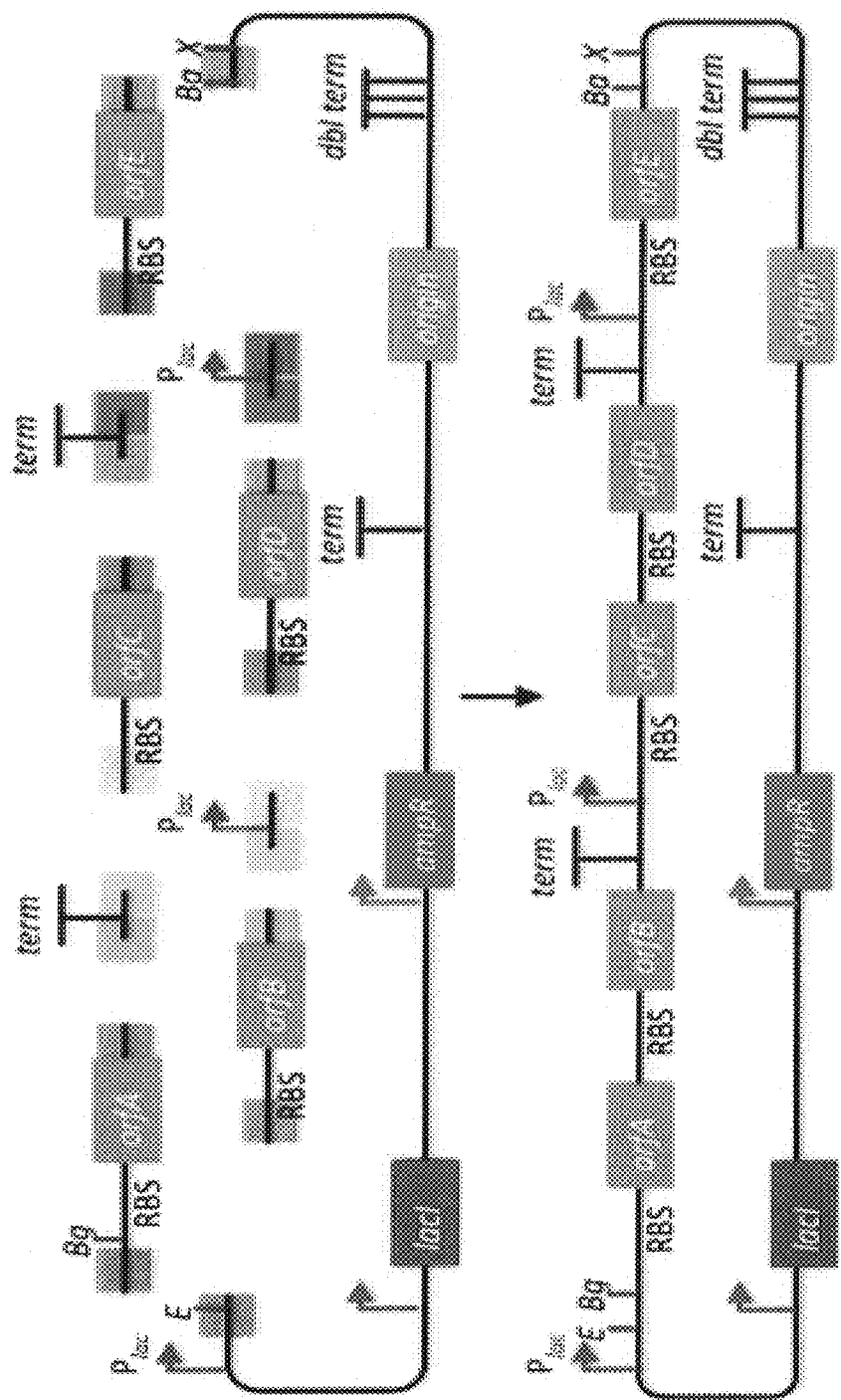
Figure 1L:
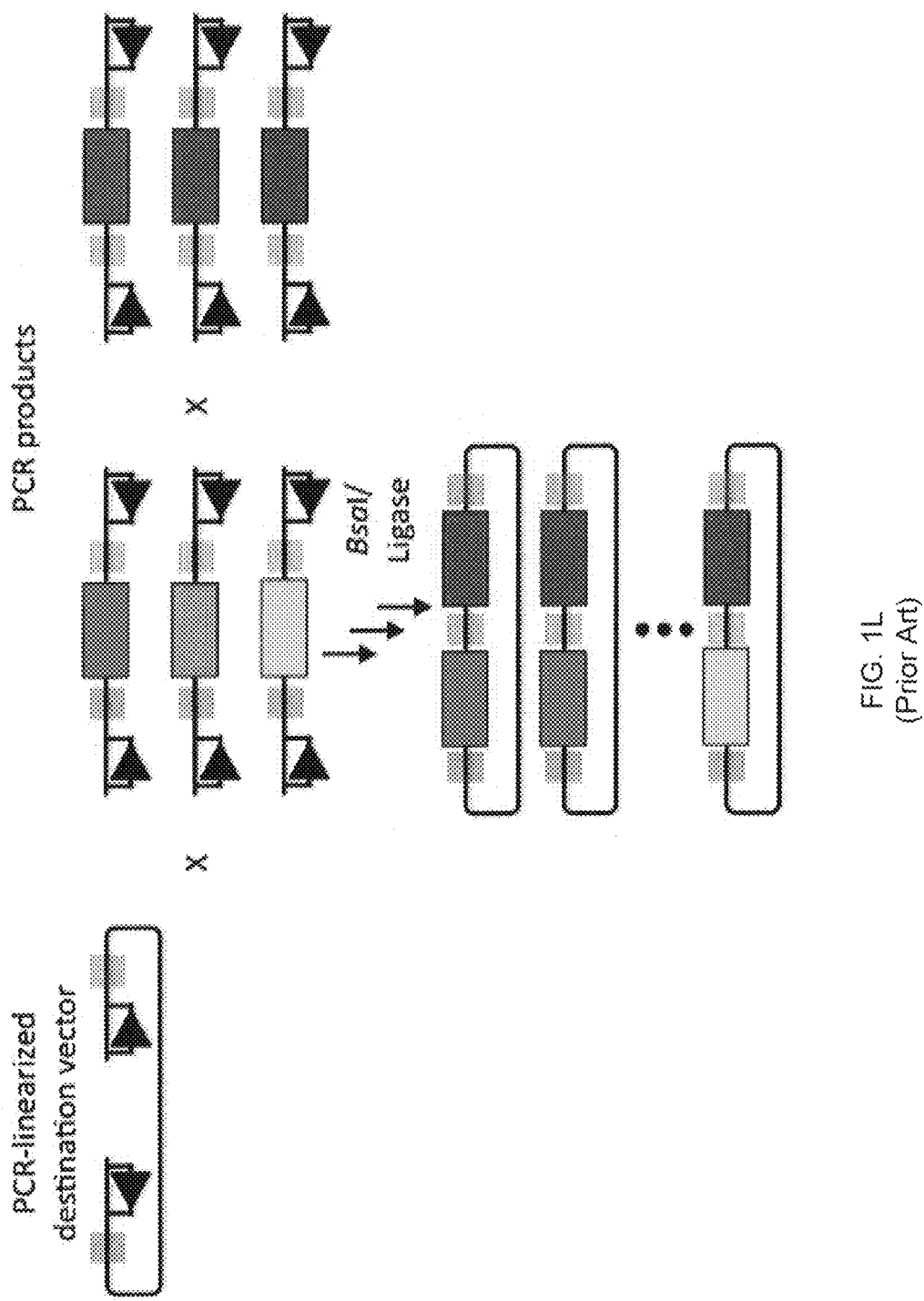

The present invention provides a method of designing an implementation of a DNA assembly. In an exemplary embodiment, the method includes (1) receiving a list of DNA sequence fragments to be assembled together and an order in which to assemble the DNA sequence fragments, (2) designing DNA oligonucleotides (oligos) for each of the DNA sequence fragments, and (3) creating a plan for adding flanking homology sequences to each of the DNA oligos.

In an exemplary embodiment, the method includes (1) receiving a list of DNA sequence fragments to be assembled together and an order in which to assemble the DNA sequence fragments, (2) designing direct synthesis pieces and DNA oligonucleotides (oligos) for each of the DNA sequence fragments, and (3) creating a plan for adding flanking homology sequences to each of the direct synthesis pieces.

In an exemplary embodiment, the method includes (1) receiving a list of DNA sequence fragments to be assembled together and an order in which to assemble the DNA sequence fragments, (2) designing DNA oligonucleotides (oligos) and direct synthesis pieces for each of the DNA sequence fragments, and (3) creating a plan for adding flanking homology sequences to each of the DNA oligos and to each of the direct synthesis pieces.

In an exemplary embodiment, the method includes (1) receiving a list of DNA sequence fragments to be assembled together and an order in which to assemble the DNA sequence fragments, (2) designing DNA oligonucleotides (oligos) for each of the DNA sequence fragments, and (3) creating a plan for adding optimized overhang sequences to each of the DNA oligos.

In an exemplary embodiment, the method includes (1) receiving a list of DNA sequence fragments to be assembled together and an order in which to assemble the DNA sequence fragments, (2) designing direct synthesis pieces and DNA oligonucleotides (oligos) for each of the DNA sequence fragments, and (3) creating a plan for adding optimized overhang sequences to each of the direct synthesis pieces.

In an exemplary embodiment, the method includes (1) receiving a list of DNA sequence fragments to be assembled together and an order in which to assemble the DNA sequence fragments, (2) designing DNA oligonucleotides (oligos) and direct synthesis pieces for each of the DNA sequence fragments, and (3) creating a plan for adding optimized overhang sequences to each of the DNA oligos and to each of the direct synthesis pieces.

Given (putatively combinatorial) sequences of a linearized vector backbone and insert parts, the present invention designs SLIC/Gibson/CPEC flanking homology sequences or Golden-gate overhangs for each assembly piece, and performs an analysis to determine for which, if any, portions of the assembly direct synthesis would be more cost-effective than either PCR/SOE or oligo embedding. The present invention then designs the resulting DNA sequences for cost-effective direct synthesis, as well as the DNA oligos (suggesting re-use of existing oligos where possible) to amplify the desired assembly pieces. Finally, the present invention outputs the PCR reactions to perform, details the resulting DNA sequences that will be assembled together, checks for any incompatibilities between the assembly pieces, and prepares an annotated sequence file for the resulting assembly. Thus, the present invention automates the tedious, laborious, and error-prone portions of the DNA assembly design process. Furthermore, the present invention condenses/aggregates multiple independent assembly designs (into 96-well plate format, including optimally distributing reactions across a thermo-cycler annealing temperature gradient, thereby facilitating the execution of assembly protocols utilizing liquid handling robotics.

Flanking Homology Sequences

Figure 2:
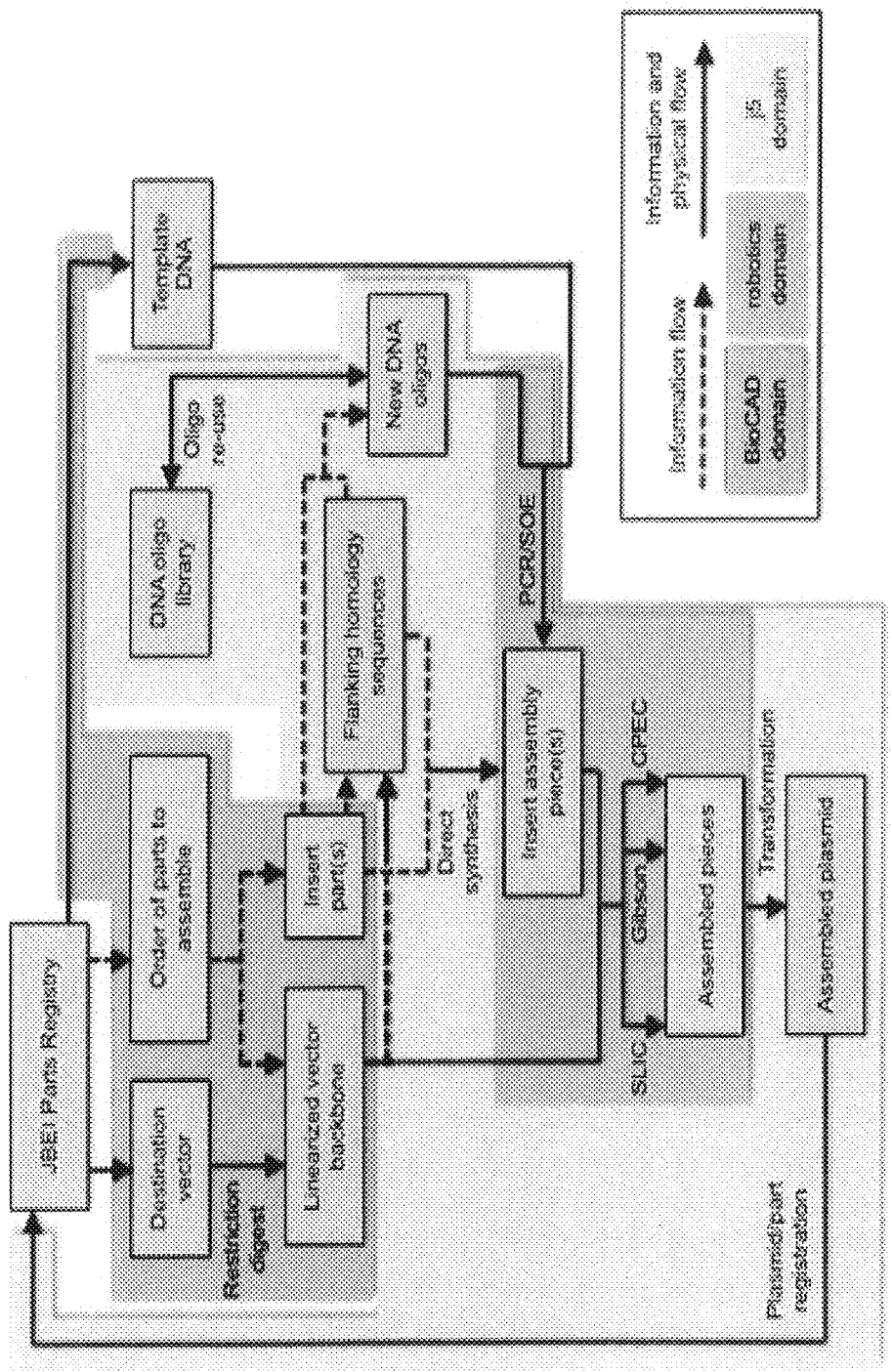
FIG. 2 illustrates a system in accordance with an embodiment of the present invention.

FIG. 2 depicts a process flow of an exemplary embodiment of the present invention using flanking homology sequences via SLIC/Gibson/CPEC assembly. In an exemplary embodiment, the present invention allows for the selection of parts to assemble from a Registry of Biological Parts (e.g., the JBEI Parts Registry) or a local collection of DNA sequences. In an exemplary embodiment, the present invention uses BioCAD (biological computer-aided design) tools in this process. Specifically, to the benefit of SLIC/Gibson/CPEC BioBrick-compatible assembly, in an exemplary embodiment, the present invention uses BioCAD tools (1) to suggest viable alternatives to undesirable repeated homologous sequences (e.g., identifying two distinct terminators with comparable function), (2) to suggest point mutations to make that disrupt internal BioBrick/BsaI restriction sites, and (3) to query collections of DNA sequences for physically existing and available sequences that already contain two or more of the parts to be assembled together in the proper order and proper orientation, thereby reducing redundant fragment assembly steps where at all possible. The present invention then categorizes the parts to be assembled into either the linearized destination vector, or insert parts. The linearized destination vector is nominally physically achieved by digesting the destination vector with restriction enzymes or by polymerase chain reaction (PCR)-amplifying the vector backbone, although direct DNA synthesis of an entire vector backbone could be done as well.

Given the sequences of the linearized vector backbone and the insert parts, the present invention designs the flanking homology sequences for each assembly piece, and performs an analysis to determine for which, if any, portions of the assembly direct synthesis would be more cost-effective than either PCR/SOE or oligo embedding. The present invention then designs DNA oligos for synthesis, and/or suggests re-use of existing oligos where possible, to amplify the desired assembly pieces. Notably, the vector backbone and/or any of the insert parts to be assembled do not necessarily need to physically exist (a prerequisite endonuclease digestion or PCR amplification) before the present invention is used to design the assembly, since it is possible to specify a direct synthesis strategy for any assembly fragment.

The present invention allows for liquid handling robotics or other devices to assist the execution of PCR/SOE to generate the assembly pieces, as well as their subsequent SLIC/Gibson/CPEC assembly. The present invention facilitates this process by condensing/aggregating designs for multiple independent assemblies (into 96-well plate format, including optimally distributing reactions across a thermo-cycler annealing temperature gradient. After transforming a competent cloning strain with the assembly reaction, the present invention sequence verifies a clonal isolate of the assembled plasmid, and deposits the clonal isolate into the parts registry or local collection for subsequent re-use.

DNA Oligonucleotides (Oligos)

Figure 3A:
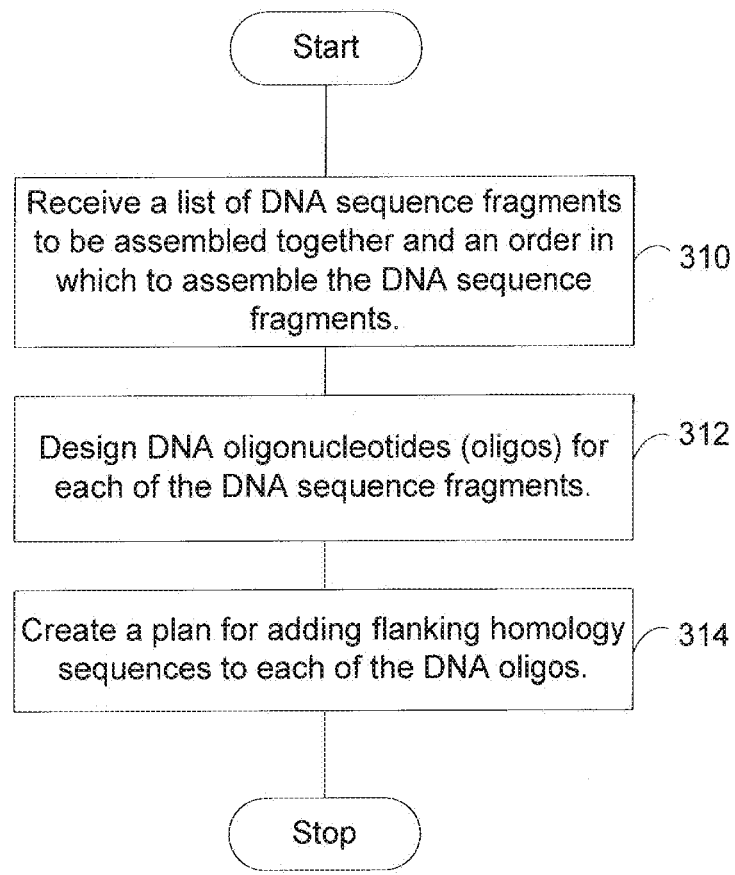
FIG. 3A-3F are flowcharts in accordance with an exemplary embodiment of the present invention.
Figure 3B:
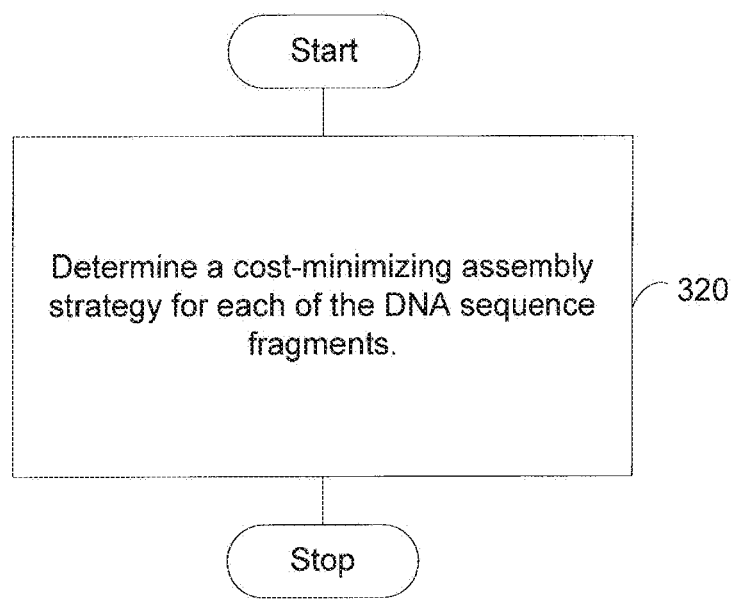

Referring to FIG. 3A, in an exemplary embodiment, the present invention includes a step 310 of receiving a list of DNA sequence fragments to be assembled together and an order in which to assemble the DNA sequence fragments, a step 312 of designing DNA oligonucleotides (oligos) for each of the DNA sequence fragments, and a step 314 of creating a plan for adding flanking homology sequences to each of the DNA oligos, Referring to FIG. 3B, in an exemplary embodiment, the present invention further includes a step 320 of determining a cost-minimizing assembly strategy for each of the DNA sequence fragments.

Figure 3C:
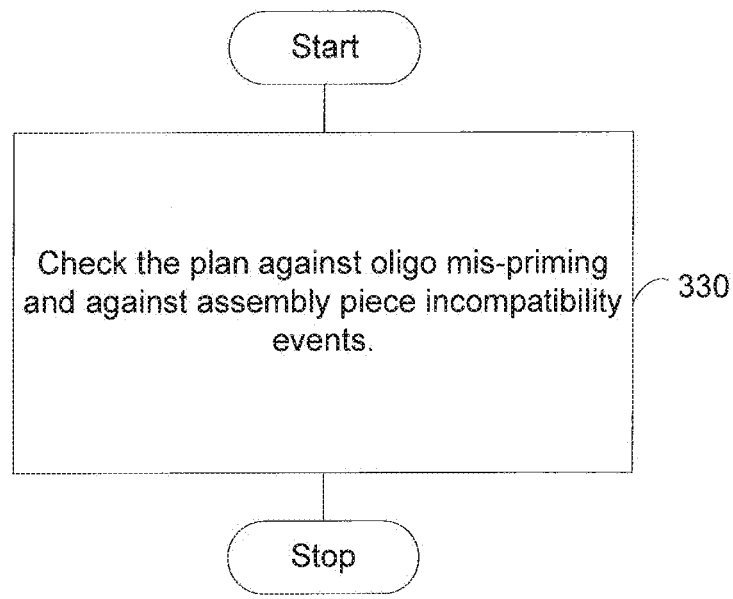
Figure 3D:
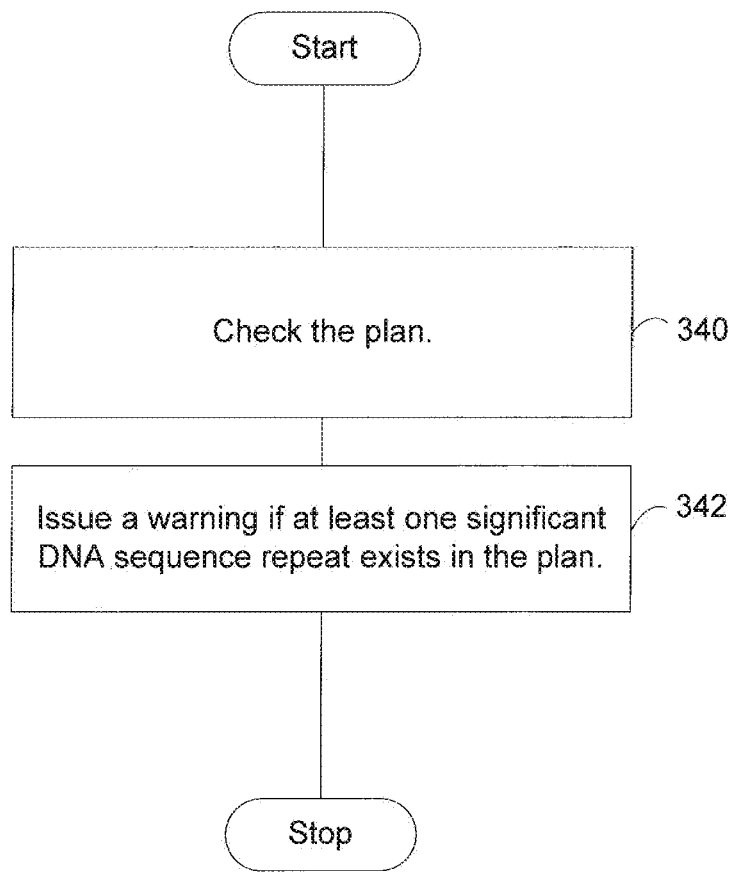

Referring to FIG. 3C, in an exemplary embodiment, the present invention further includes a step 330 of checking the plan against oligo mis-priming and against assembly piece incompatibility events. Referring to FIG. 3D, in an exemplary embodiment, the present invention further includes a step 340 of checking the plan and a step 342 of issuing a warning if at least one significant DNA sequence repeat exists in the plan.

Figure 3E:
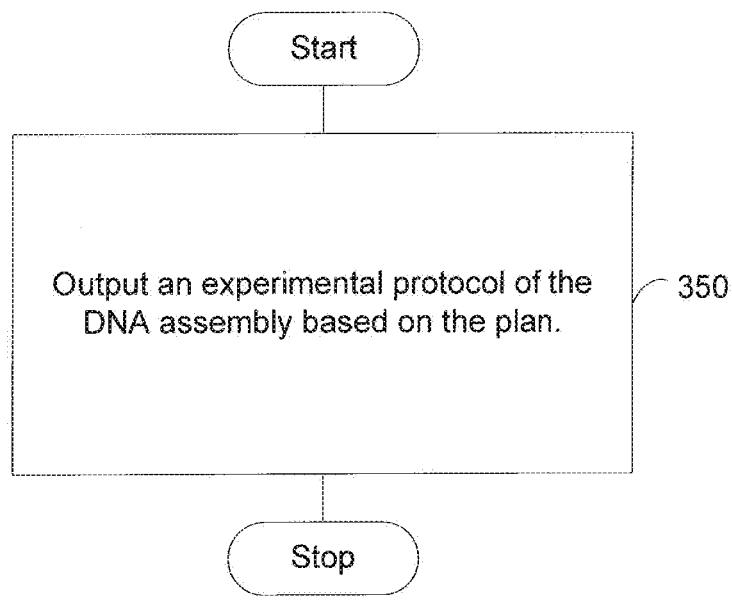
Figure 3F:
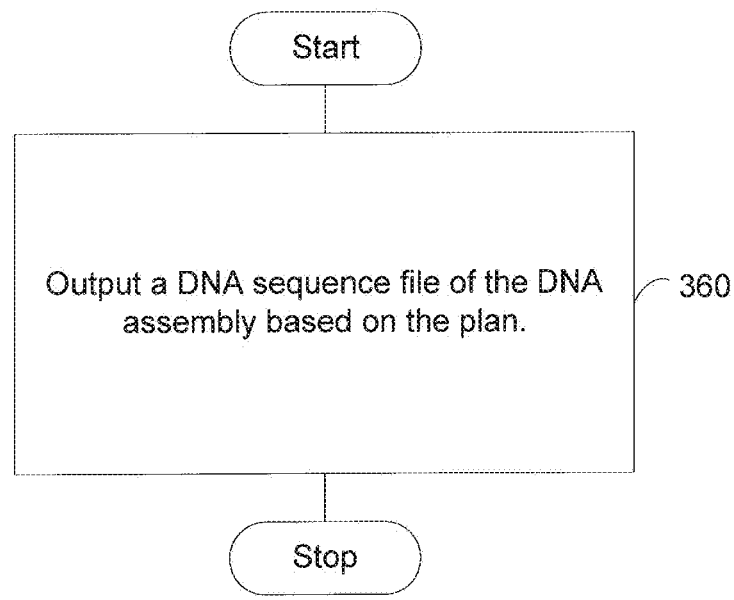

Referring to FIG. 3E, in an exemplary embodiment, the present invention further includes a step 350 of outputting an experimental protocol of the DNA assembly based on the plan. Referring to FIG. 3F, in an exemplary embodiment, the present invention further includes a step 360 of outputting a DNA sequence file of the DNA assembly based on the plan.

Receiving

Figure 4A:
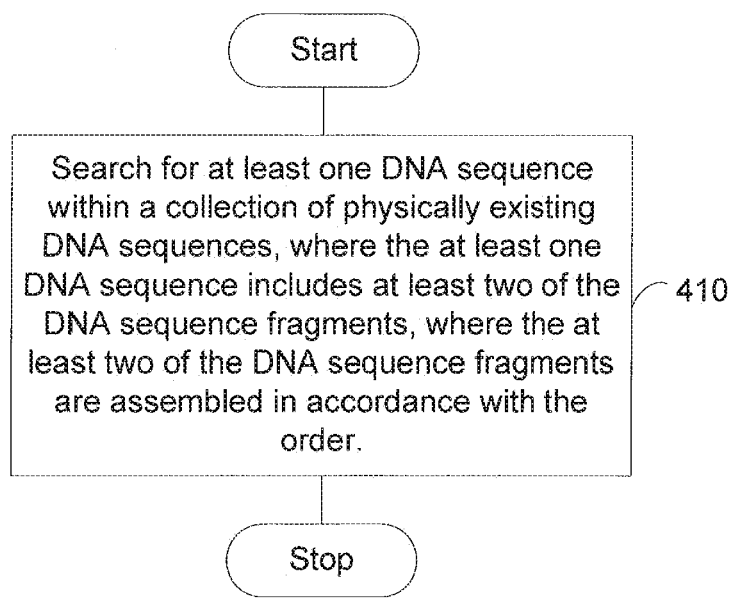
FIG. 4A-4E are flowcharts in accordance with an exemplary embodiment of the present invention.
Figure 4B:
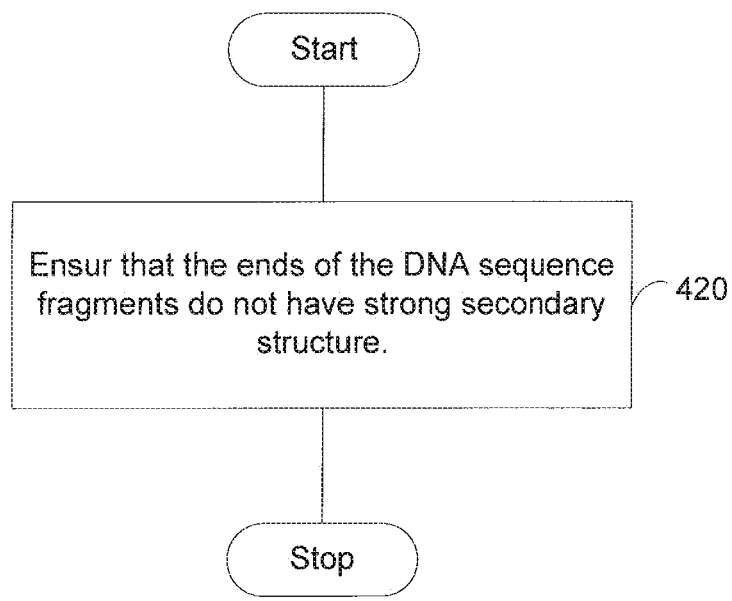

Referring to FIG. 4A, in an exemplary embodiment, receiving step 310 further includes a step 410 of searching for at least one DNA sequence within a collection of physically existing DNA sequences, where the at least one DNA sequence includes at least two of the DNA sequence fragments, where the at least two of the DNA sequence fragments are assembled in accordance with the order. Referring to FIG. 4B, in an exemplary embodiment, receiving step 310 further includes a step 420 of ensuring that the ends of the DNA sequence fragments do not have strong secondary structure.

Figure 4C:
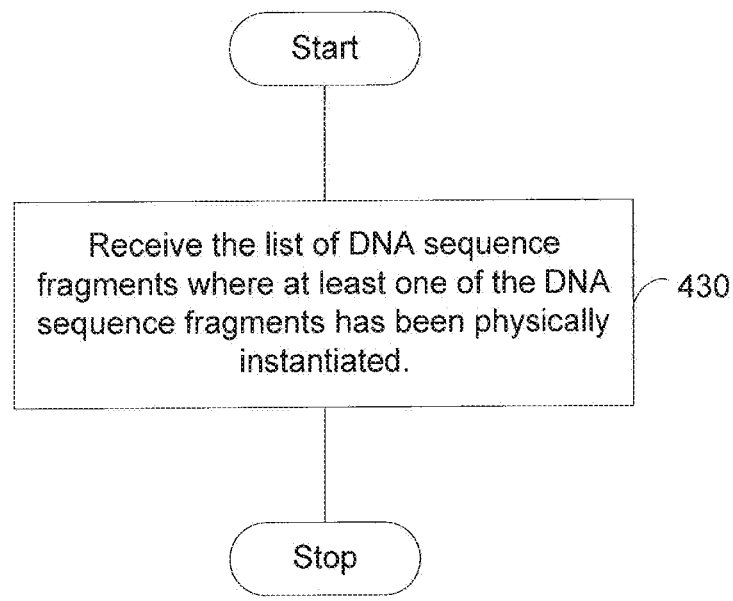
Figure 4D:
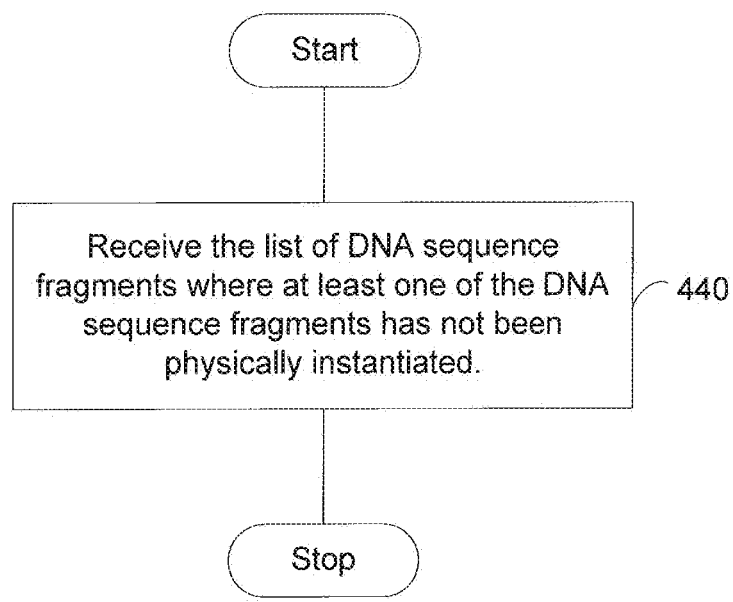
Figure 4E:
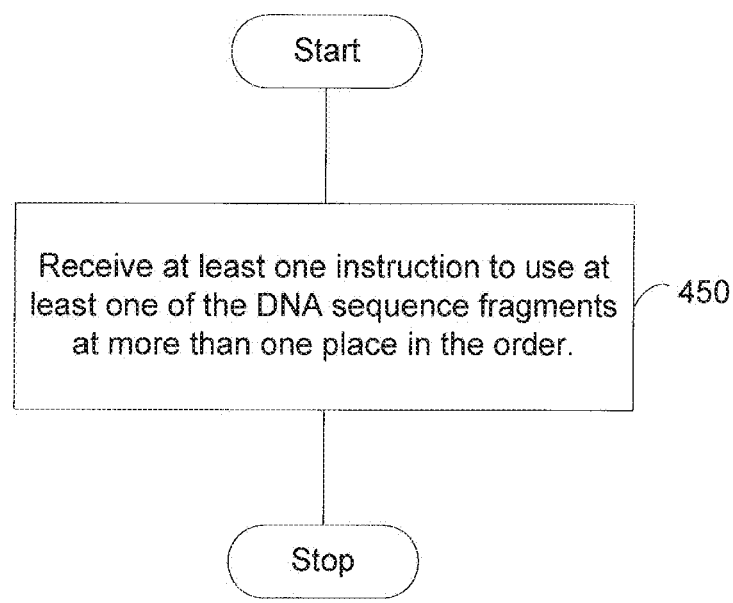

Referring to FIG. 4C, in an exemplary embodiment, receiving step 310 includes a step 430 of receiving the list of DNA sequence fragments where at least one of the DNA sequence fragments has been physically instantiated. Referring to FIG. 4D, in an exemplary embodiment, receiving step 310 includes a step 440 of receiving the list of DNA sequence fragments where at least one of the DNA sequence fragments has not been physically instantiated. Referring to FIG. 4E, in an exemplary embodiment, receiving step 310 includes a step 450 of receiving at least one instruction to use at least one of the DNA sequence fragments at more than one place in the order.

Creating

Figure 5A:
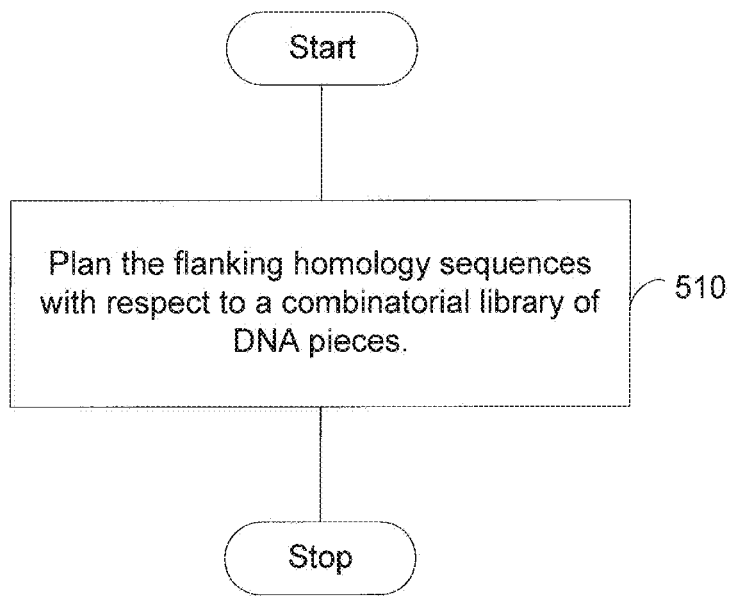
FIGS. 5A and 5B are flowcharts in accordance with an exemplary embodiment of the present invention.
Figure 5B:
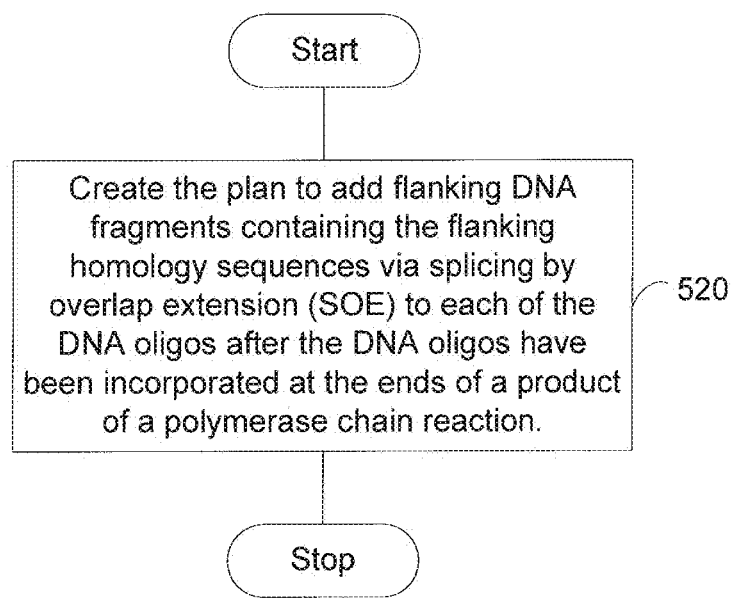

Referring to FIG. 5A, in an exemplary embodiment, creating step 314 includes a step 510 of planning the flanking homology sequences with respect to a combinatorial library of DNA pieces. Referring to FIG. 5B, in an exemplary embodiment, creating step 314 includes a step 520 of creating the plan to add flanking DNA fragments containing the flanking homology sequences via splicing by overlap extension (SOE) to each of the DNA oligos after the DNA oligos have been incorporated at the ends of a product of a polymerase chain reaction.

Determining

Figure 6A:
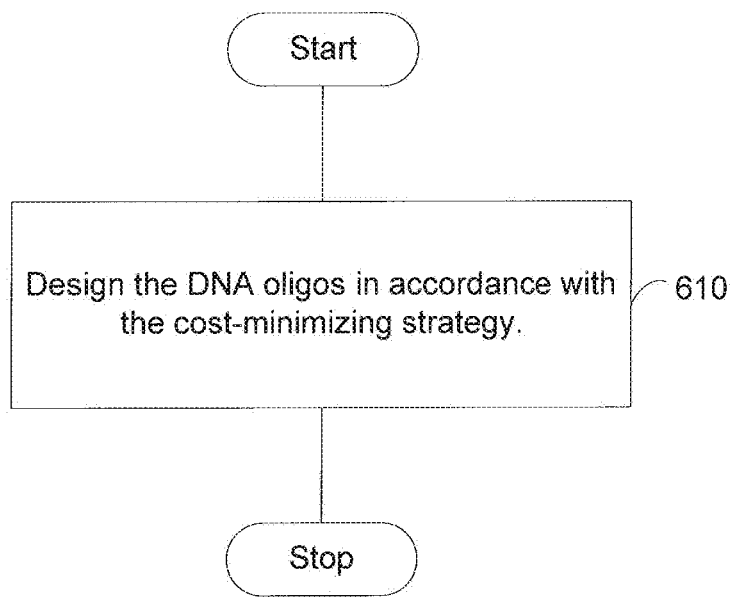
FIGS. 6A and 6B are flowcharts in accordance with an exemplary embodiment of the present invention.
Figure 6B:
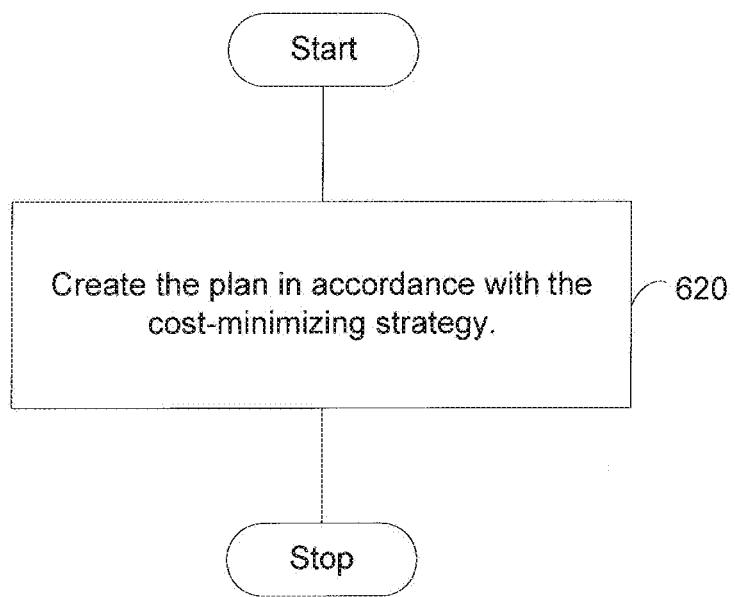

Referring to FIG. 6A, in an exemplary embodiment, determining step 320 includes a step 610 of designing the DNA oligos in accordance with the cost-minimizing strategy. Referring to FIG. 6B, in an exemplary embodiment, determining step 320 includes a step 620 of creating the plan in accordance with the cost-minimizing strategy.

Checking

Figure 7:
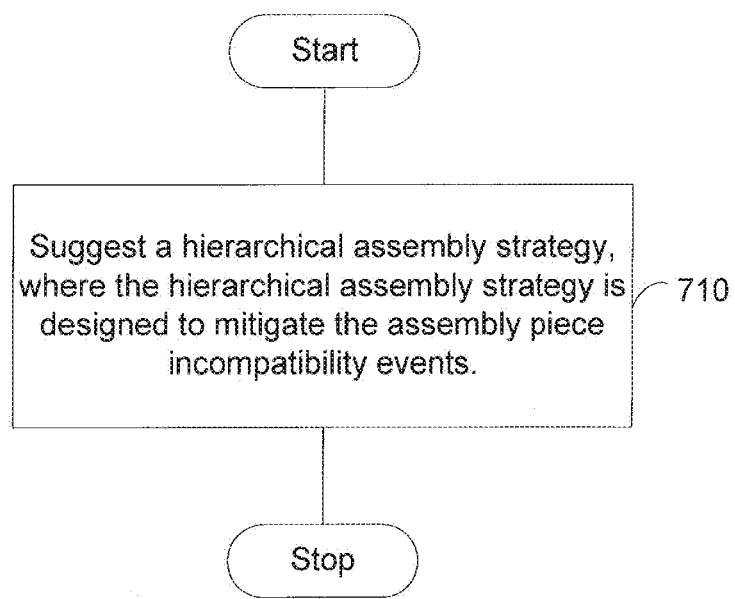
FIG. 7 is a flowchart in accordance with an exemplary embodiment of the present invention.

Referring to FIG. 7, in an exemplary embodiment, checking step 330 further includes a step 710 of suggesting a hierarchical assembly strategy, where the hierarchical assembly strategy is designed to mitigate the assembly piece incompatibility events.

Outputting

Figure 8A:
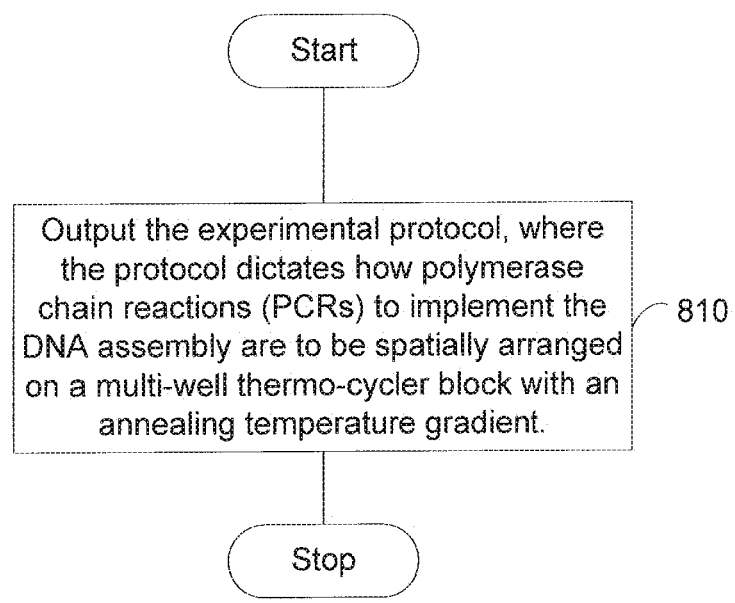
FIG. 8A-8D are flowcharts in accordance with an exemplary embodiment of the present invention.
Figure 8B:
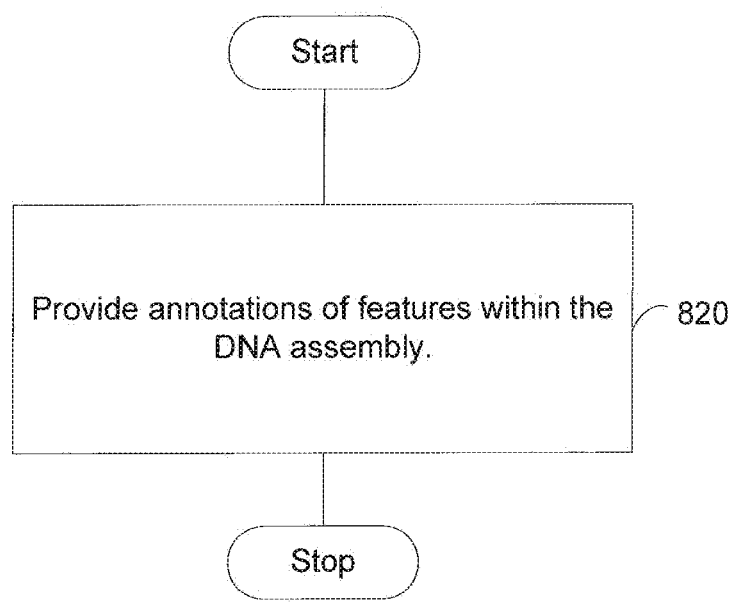

Referring to FIG. 8A, in an exemplary embodiment, outputting step 350 includes a step 810 of outputting the experimental protocol, where the protocol dictates how polymerase chain reactions (PCRs) to implement the DNA assembly are to be spatially arranged on a multi-well thermo-cycler block with an annealing temperature gradient. Referring to FIG. 8B, in an exemplary embodiment, outputting step 360 further includes a step 820 of providing annotations of features within the DNA assembly.

Figure 8C:
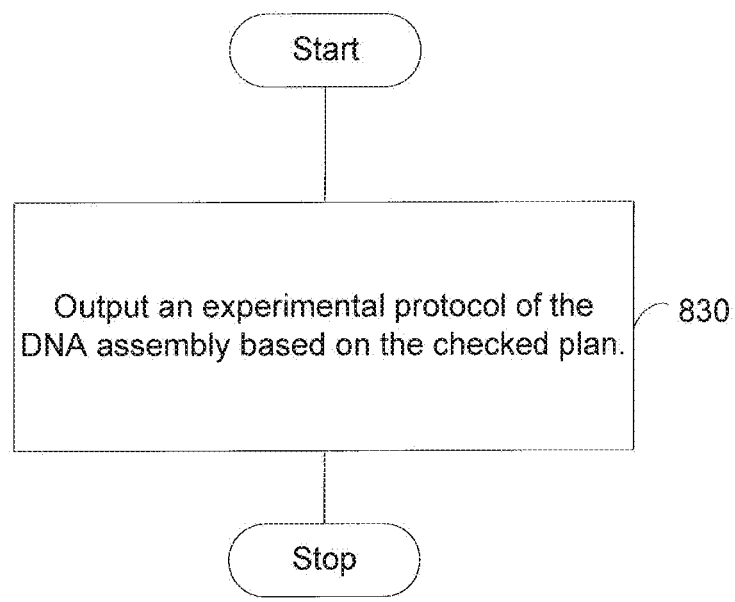
Figure 8D:
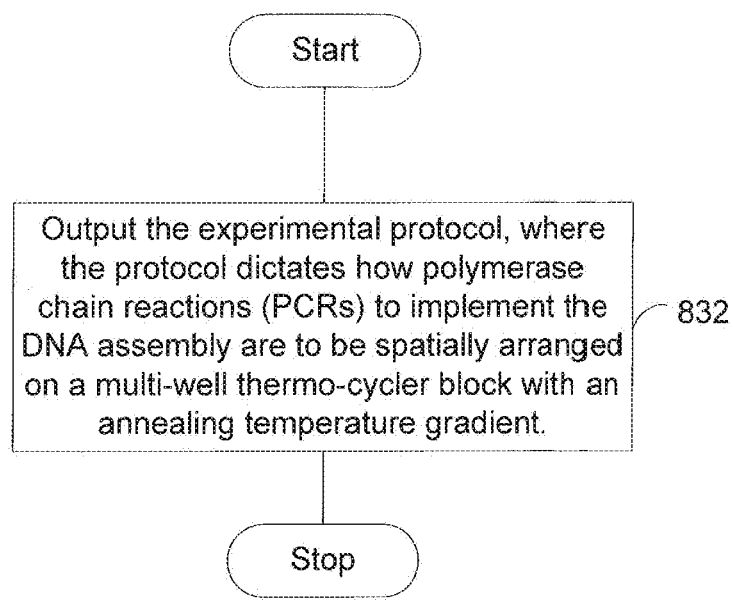

Referring to FIG. 8C, in an exemplary embodiment, checking step 330 further includes a step 830 of outputting an experimental protocol of the DNA assembly based on the Checked plan. Referring to FIG. 8D, in an exemplary embodiment, outputting step 830 includes a step 832 of outputting the experimental protocol, where the protocol dictates how polymerase chain reactions (PCRs) to implement the DNA assembly are to be spatially arranged on a multi-well thermo-cycler block with an annealing temperature gradient.

Direct Synthesis Pieces and DNA Oligonucleotides (Oligos)

Referring to FIG. 9, in an exemplary embodiment, the present invention includes a step 910 of receiving a list of DNA sequence fragments to be assembled together and an order in which to assemble the DNA sequence fragments, a step 912 of designing direct synthesis pieces and DNA oligonucleotides (oligos) for each of the DNA sequence fragments, and a step 914 of creating a plan for adding flanking homology sequences to each of the direct synthesis pieces. Referring to FIG. 9B, in an exemplary embodiment, the present invention further includes a step 920 of determining a cost-minimizing assembly strategy for each of the DNA sequence fragments.

Figure 9A:
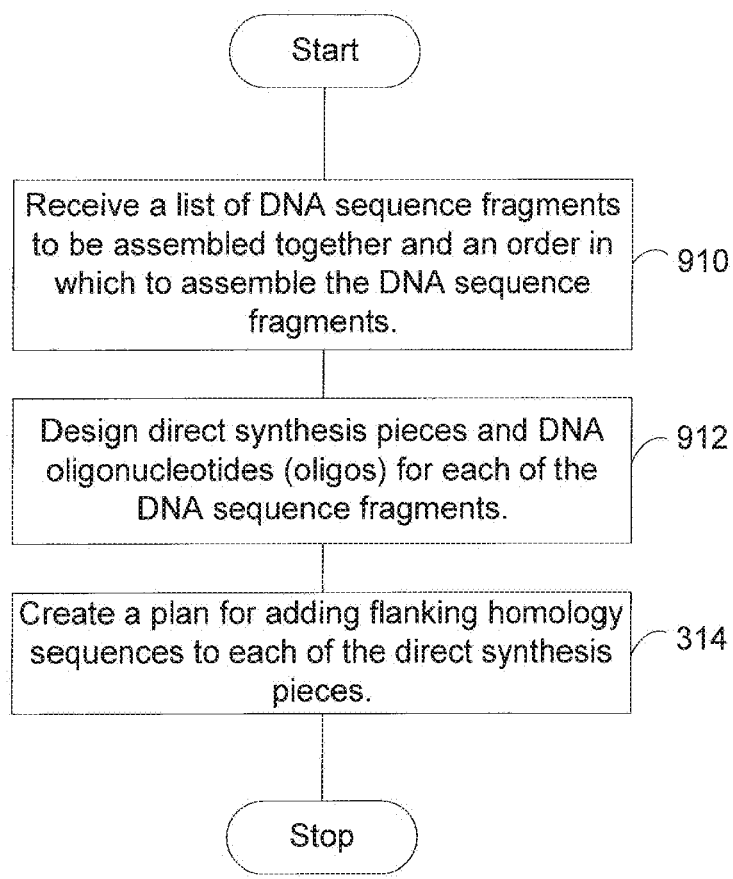
FIG. 9A-9F are flowcharts in accordance with an exemplary embodiment of the present invention.
Figure 9B:
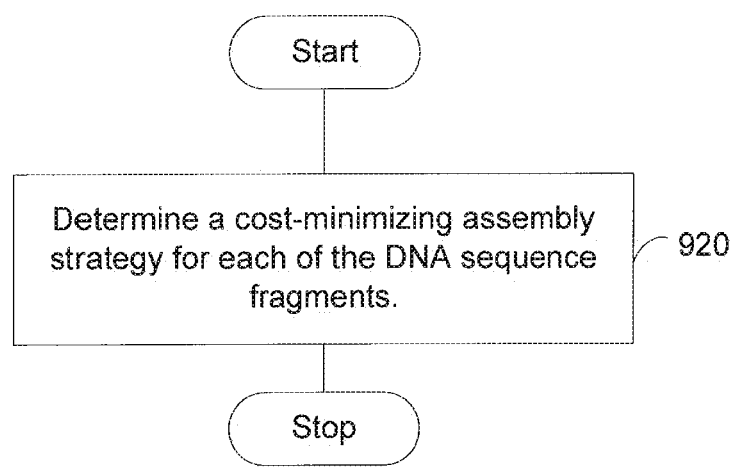
Figure 9C:
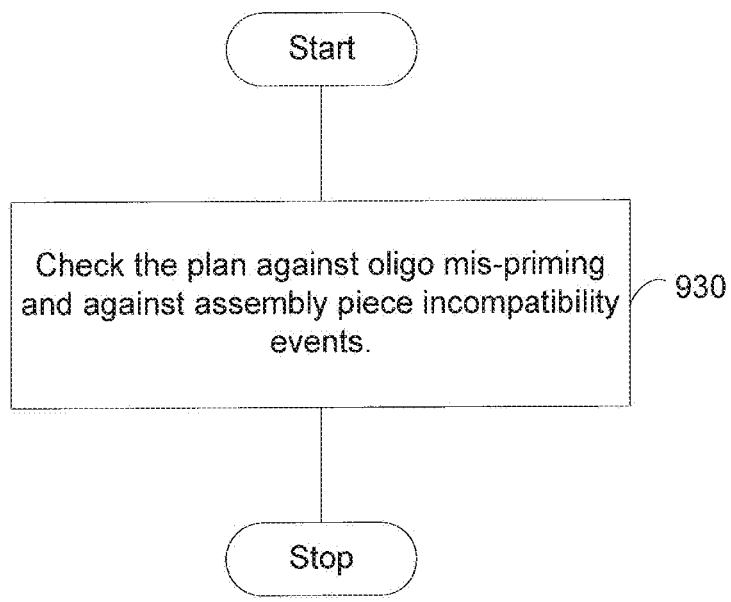
Figure 9D:
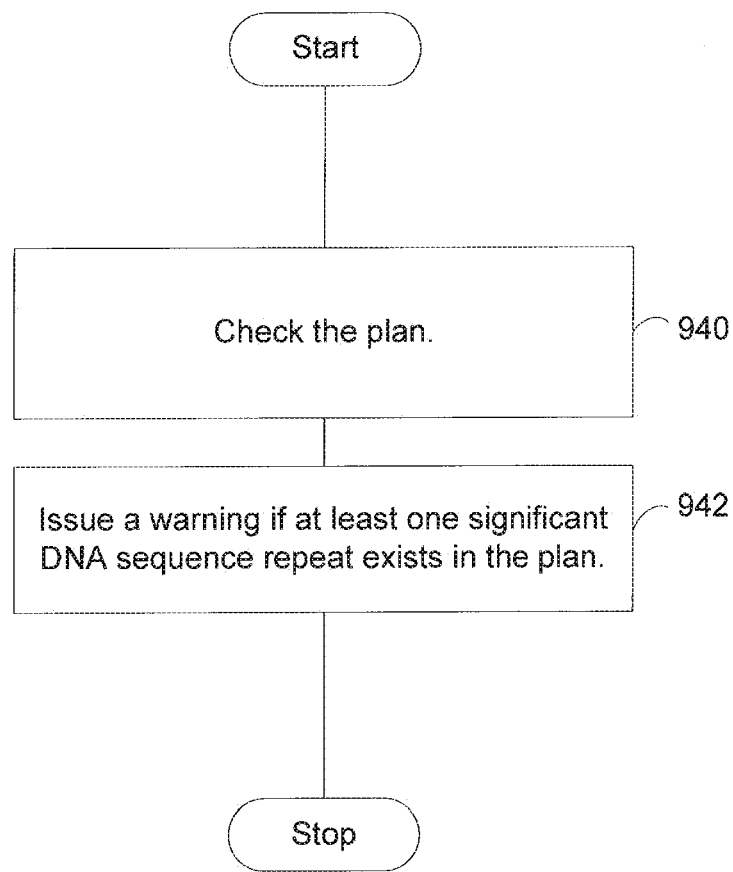

Referring to FIG. 9C, in an exemplary embodiment, the present invention further includes a step 930 of checking the plan against oligo mis-priming and against assembly piece incompatibility events. Referring to FIG. 9D, in an exemplary embodiment, the present invention further includes a step 940 of checking the plan and a step 942 of issuing a warning if at least one significant DNA sequence repeat exists in the plan.

Figure 9E:
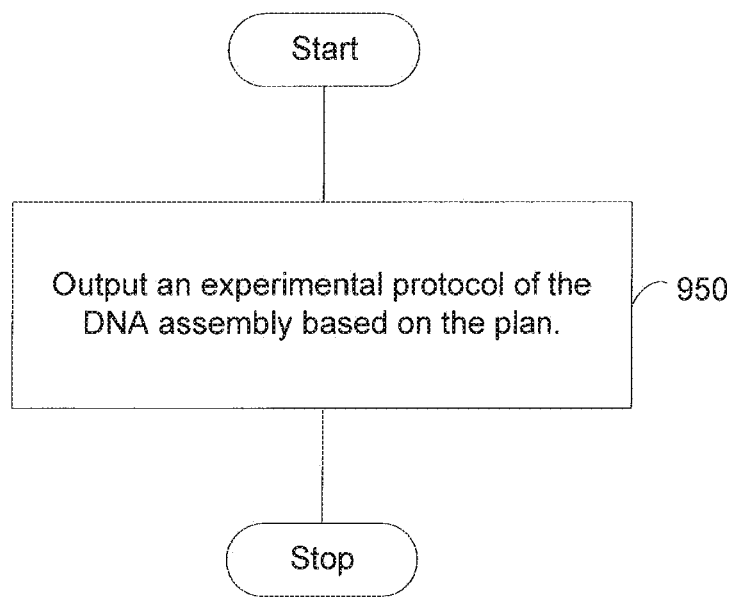
Figure 9F:
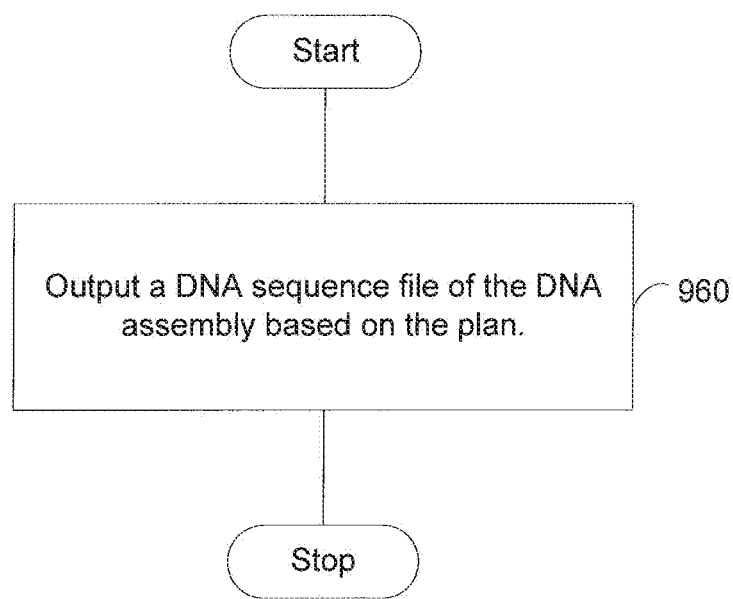

Referring to FIG. 9E, in an exemplary embodiment, the present invention further includes a step 950 of outputting an experimental protocol of the DNA assembly based on the plan. Referring to FIG. 9F, in an exemplary embodiment, the present invention further includes a step 960 of outputting a DNA sequence file of the DNA assembly based on the plan.

Receiving

In an exemplary embodiment, receiving step 910 further includes a step of searching for at least one DNA sequence within a collection of physically existing DNA sequences, where the at least one DNA sequence includes at least two of the DNA sequence fragments, where the at least two of the DNA sequence fragments are assembled in accordance with the order. In an exemplary embodiment, receiving step 910 further includes a step of ensuring that the ends of the DNA sequence fragments do not have strong secondary structure.

In an exemplary embodiment, receiving step 910 includes a step of receiving comprises receiving the list of DNA sequence fragments where at least one of the DNA sequence fragments has been physically instantiated. In an exemplary embodiment, receiving step 910 includes a step of receiving the list of DNA sequence fragments where at least one of the DNA sequence fragments has not been physically instantiated. In an exemplary embodiment, receiving step 910 includes a step of receiving at least one instruction to use at least one of the DNA sequence fragments at more than one place in the order.

Creating

In an exemplary embodiment, creating step 914 includes a step of planning the flanking homology sequences with respect to a combinatorial library of DNA pieces. In an exemplary embodiment, creating step 914 includes a step of creating the plan to add flanking DNA fragments containing the flanking homology sequences via splicing by overlap extension (SOE) to each of the direct synthesis pieces.

Determining

In an exemplary embodiment, determining step 920 includes a step of designing the direct synthesis pieces and the DNA oligos in accordance with the cost-minimizing assembly strategy. In an exemplary embodiment, determining step 920 includes a step of creating the plan in accordance with the cost-minimizing assembly strategy.

Checking

In an exemplary embodiment, checking step 930 further includes a step of suggesting a hierarchical assembly strategy, where the hierarchical assembly strategy is designed to mitigate the assembly piece incompatibility events.

Outputting

In an exemplary embodiment, outputting step 950 includes a step of outputting the experimental protocol, where the protocol dictates how polymerase chain reactions (PCRs) to implement the DNA assembly are to be spatially arranged on a multi-well thermo-cycler block with an annealing temperature gradient. In an exemplary embodiment, outputting step 960 includes a step of providing annotations of features within the DNA assembly.

In an exemplary embodiment, checking step 930 further includes a step of outputting an experimental protocol and a DNA sequence file of the DNA assembly based on the checked plan. In an exemplary embodiment, the outputting further includes a step of outputting the experimental protocol, where the protocol dictates how polymerase chain reactions (PCRs) to implement the DNA assembly are to be spatially arranged on a multi-well thermo-cycler block with an annealing temperature gradient.

DNA Oligonucleotides (Oligos) and Direct Synthesis Pieces

Figure 10A:
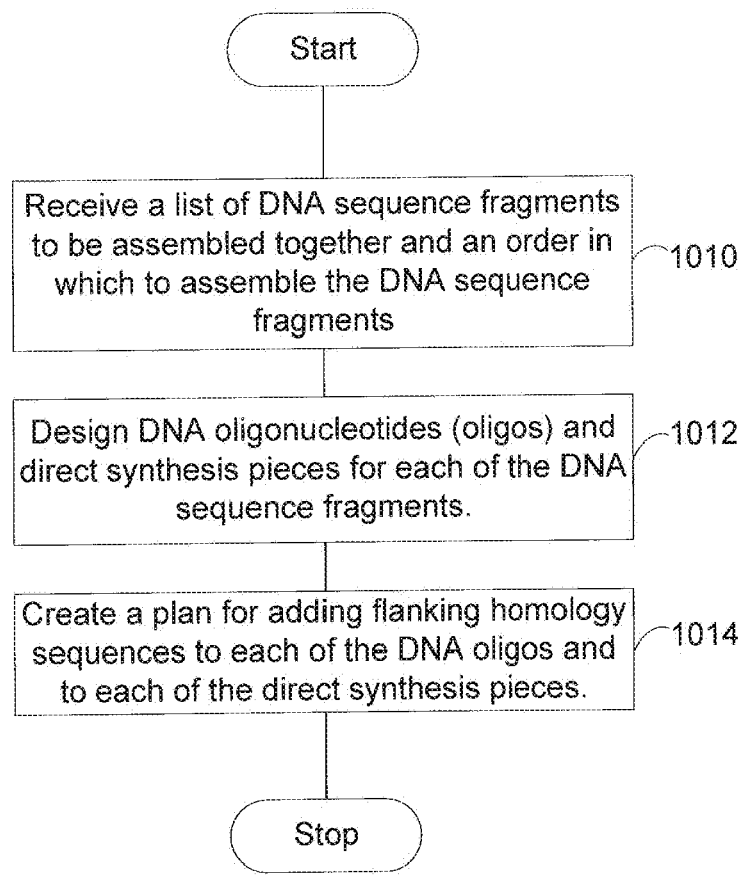
FIG. 10A-10F are flowcharts in accordance with an exemplary embodiment of the present invention.
Figure 10B:
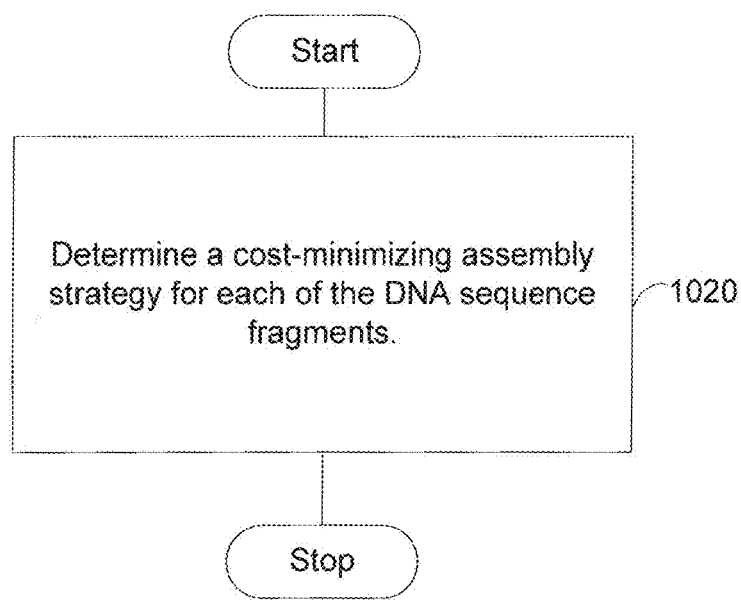

Referring to FIG. 10A, in an exemplary embodiment, the present invention includes a step 1010 of receiving a list of DNA sequence fragments to be assembled together and an order in which to assemble the DNA sequence fragments, a step 1012 of designing DNA oligonucleotides (oligos) and direct synthesis pieces for each of the DNA sequence fragments, and a step 1014 of creating a plan for adding flanking homology sequences to each of the DNA oligos and to each of the direct synthesis pieces. Referring to FIG. 10B, in an exemplary embodiment, the present invention further includes a step 1020 of determining a cost-minimizing assembly strategy for each of the DNA sequence fragments.

Figure 10C:
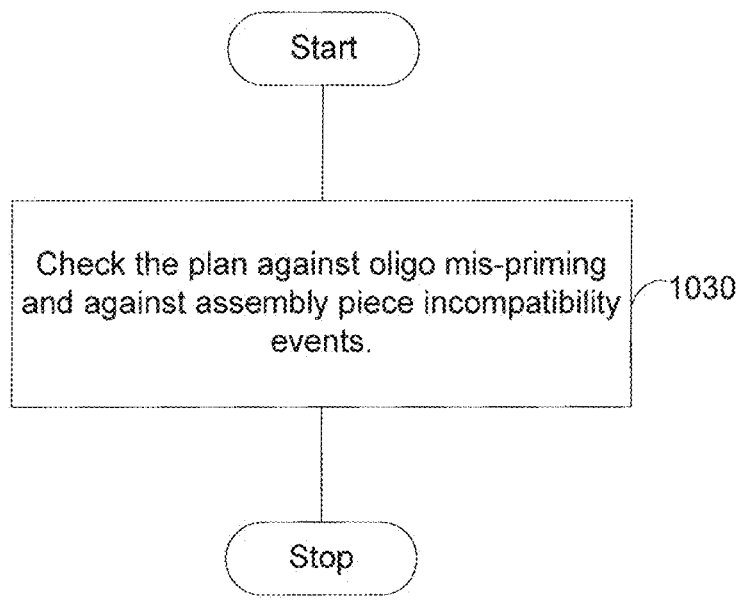
Figure 10D:
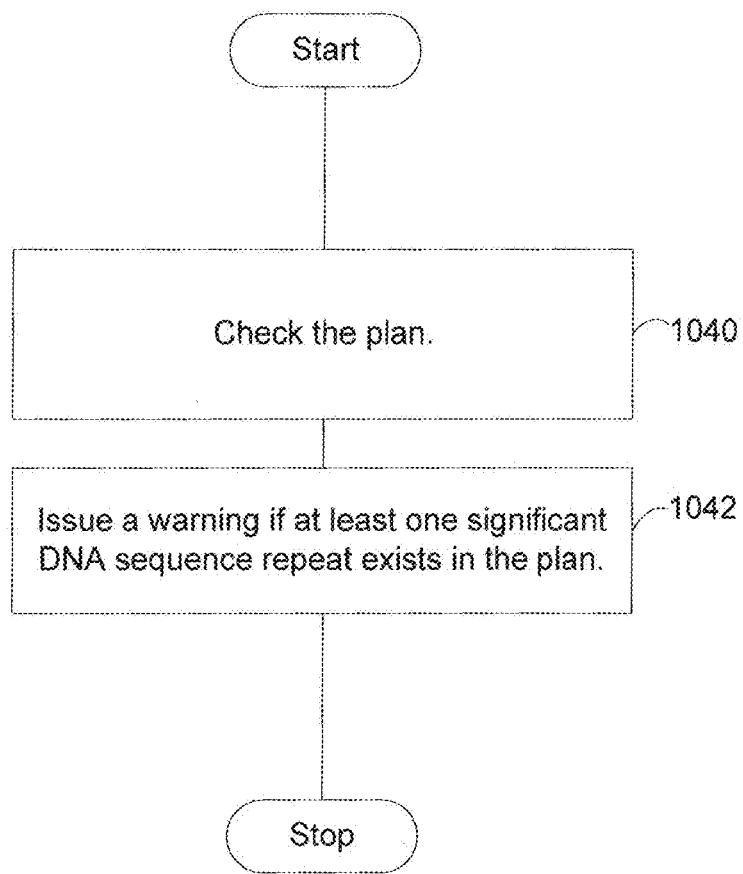

Referring to FIG. 10C, in an exemplary embodiment, the present invention further includes a step 1030 of checking the plan against oligo mis-priming and against assembly piece incompatibility events. Referring to FIG. 10D, in an exemplary embodiment, the present invention further includes a step 1040 of checking the plan and a step 1042 of issuing a warning if at least one significant DNA sequence repeat exists in the plan.

Figure 10E:
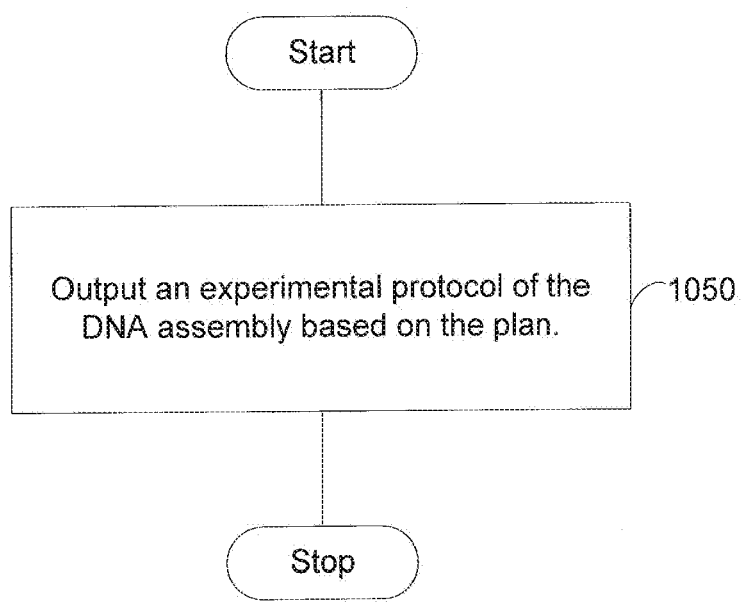
Figure 10F:
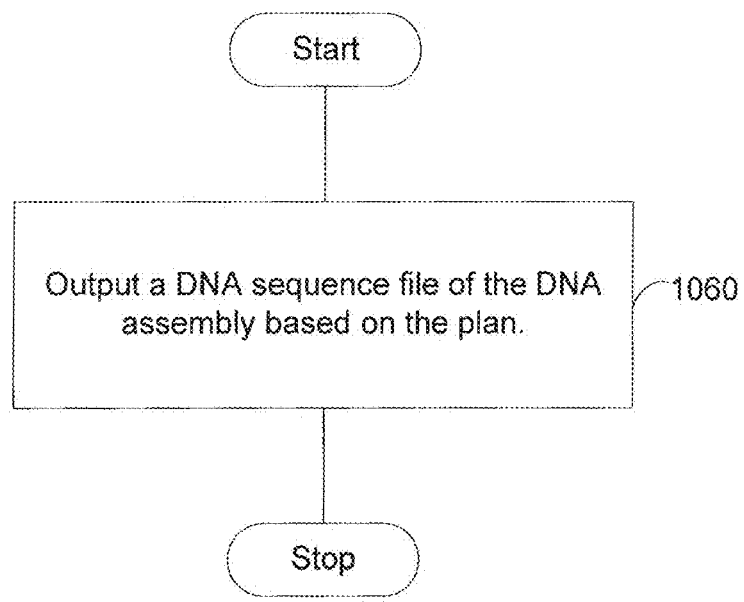

Referring to FIG. 10E, in an exemplary embodiment, the present invention further includes a step 1050 of outputting an experimental protocol of the DNA assembly based on the plan. Referring to FIG. 10F, in an exemplary embodiment, the present invention further includes a step 1060 of outputting a DNA sequence file of the DNA assembly based on the plan.

Receiving

In an exemplary embodiment, receiving step 1010 further includes a step of searching for at least one DNA sequence within a collection of physically existing DNA sequences, where the at least one DNA sequence includes at least two of the DNA sequence fragments, where the at least two of the DNA sequence fragments are assembled in accordance with the order. In an exemplary embodiment, receiving step 1010 further includes a step ensuring that the ends of the DNA sequence fragments do not have strong secondary structure.

In an exemplary embodiment, receiving step 1010 includes a step of receiving the list of DNA sequence fragments wherein at least one of the DNA sequence fragments has been physically instantiated. In an exemplary embodiment, receiving step 1010 includes a step of receiving the list of DNA sequence fragments wherein at least one of the DNA sequence fragments has not been physically instantiated. In an exemplary embodiment, receiving step 1010 includes a step of receiving at least one instruction to use at least one of the DNA sequence fragments at more than one place in the order.

Creating

In an exemplary embodiment, creating step 1014 includes a step of planning the flanking homology sequences with respect to a combinatorial library of DNA pieces. In an exemplary embodiment, creating step 1014 includes a step of creating the plan to add flanking DNA fragments containing the flanking homology sequences via splicing by overlap extension (SOE) to each of the DNA oligos and to each of the direct synthesis pieces after the DNA oligos have been incorporated at the ends of a product of a polymerase chain reaction.

Determining

In an exemplary embodiment, determining step 1020 includes a step of designing the DNA oligos and the direct synthesis pieces in accordance with the cost-minimizing assembly strategy. In an exemplary embodiment, determining step 1020 includes a step of creating the plan in accordance with the cost-minimizing assembly strategy.

Checking

In an exemplary embodiment, checking step 1030 further includes a step of suggesting a hierarchical assembly strategy, where the hierarchical assembly strategy is designed to mitigate the assembly piece incompatibility events.

Outputting

In an exemplary embodiment, outputting step 1050 includes a step of outputting the experimental protocol, where the protocol dictates how polymerase chain reactions (PCRs) to implement the DNA assembly are to be spatially arranged on a multi-well thermo-cycler block with an annealing temperature gradient. In an exemplary embodiment, outputting step 1060 further includes a step of providing annotations of features within the DNA assembly.

In an exemplary embodiment, checking step 1030 further includes a step of outputting an experimental protocol and a DNA sequence file of the DNA assembly based on the checked plan. In an exemplary embodiment, the outputting includes a step of outputting the experimental protocol, wherein the protocol dictates how polymerase chain reactions (PCRs) to implement the DNA assembly are to be spatially arranged on a multi-well thermo-cycler block with an annealing temperature gradient.

Optimized Overhang Sequences

Figure 18:
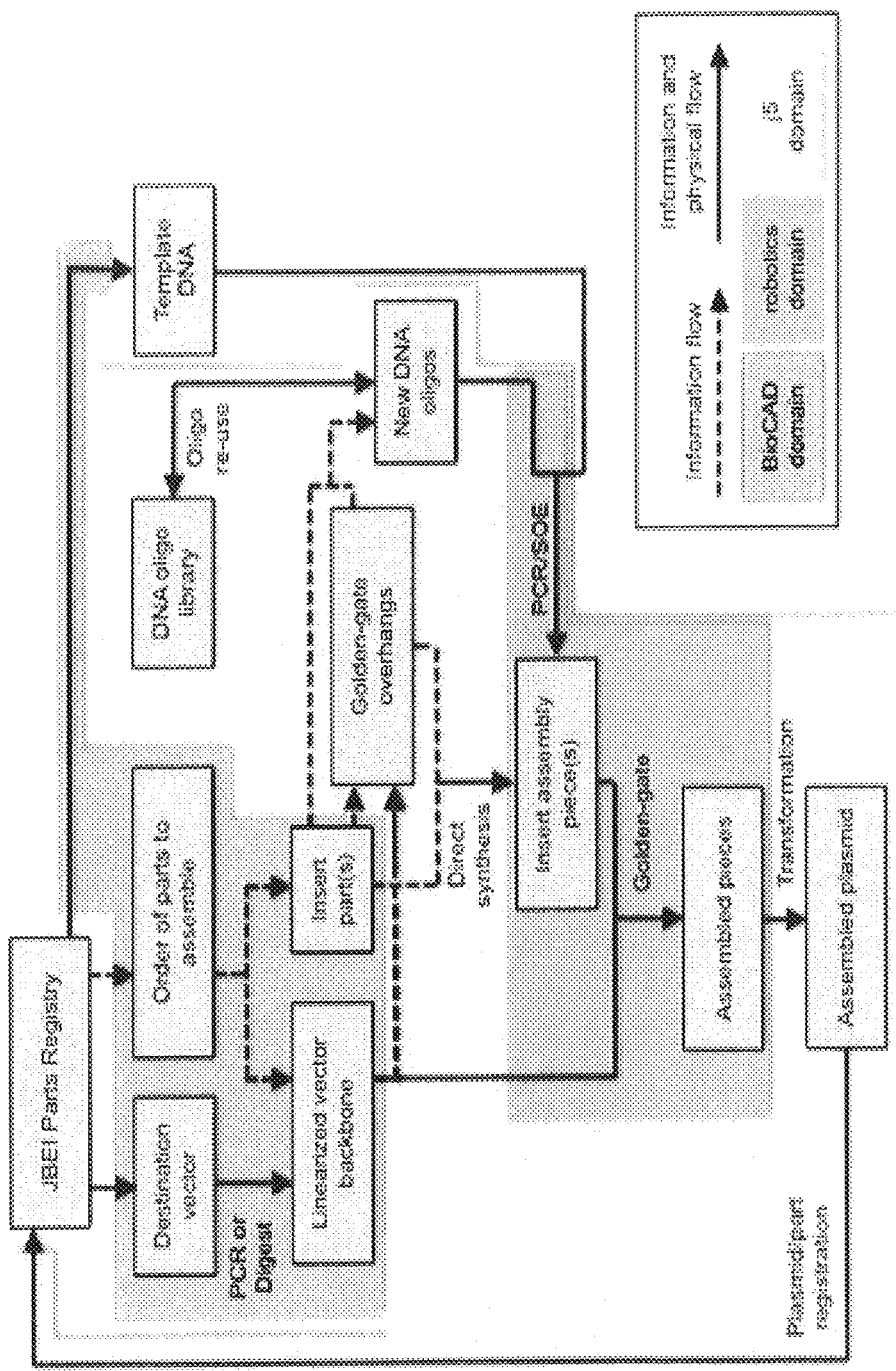
FIG. 18 illustrates a system in accordance with an embodiment of the present invention.

FIG. 18 depicts a process flow of an exemplary embodiment of the present invention using optimized overhang sequences via Golden-gate assembly. In an exemplary embodiment, the present invention allows for the selection of parts to assemble from a Registry of Biological Parts (e.g., the JBEI Parts Registry) or a local collection of DNA sequences. In an exemplary embodiment, the present invention uses BioCAD (biological computer-aided design) tools in this process. Specifically, to the benefit of Golden-gate assembly, in an exemplary embodiment, the present invention uses BioCAD tools (1) to suggest viable alternatives to undesirable repeated homologous sequences (e.g., identifying two distinct terminators with comparable function), (2) to suggest point mutations to make that disrupt internal BioBrick/BsaI restriction sites, and (3) to query collections of DNA sequences for physically existing and available sequences that already contain two or more of the parts to be assembled together in the proper order and proper orientation, thereby reducing redundant fragment assembly steps where at all possible. The present invention then categorizes the parts to be assembled into either the linearized destination vector, or insert parts. The linearized destination vector is nominally physically achieved by digesting the destination vector with restriction enzymes or by PCR-amplifying the vector backbone, although direct DNA synthesis of an entire vector backbone could be done as well.

Given the sequences of the linearized vector backbone and the insert parts, the present invention designs 4 bp overhang sequences for each assembly piece, and performs an analysis to determine for which, if any, portions of the assembly direct synthesis would be more cost-effective than either PCR/SOE or oligo embedding. The present invention then designs DNA oligos for synthesis, and/or suggests re-use of existing oligos where possible, to amplify the desired assembly pieces. Notably, the vector backbone and/or any of the insert parts to be assembled do not necessarily need to physically exist (a prerequisite endonuclease digestion or PCR amplification) before the present invention is used to design the assembly, since it is possible to specify a direct synthesis strategy for any assembly fragment.

The present invention allows for liquid handling robotics or other devices to assist the execution of PCR/SOE to generate the assembly pieces, as well as their subsequent SLIC/Gibson/CPEC assembly. The present invention facilitates this process by condensing/aggregating designs for multiple independent assemblies (into 96-well plate format, including optimally distributing reactions across a thermo-cycler annealing temperature gradient. After transforming a competent cloning strain with the assembly reaction, the present invention sequence verifies a clonal isolate of the assembled plasmid, and deposits the clonal isolate into the parts registry or local collection for subsequent re-use.

When designing Golden-gate assemblies, the present invention assumes that there are no internal BsaI sites in any of the DNA fragments to be assembled.

DNA Oligonucleotides (Oligos)

Figure 19A:
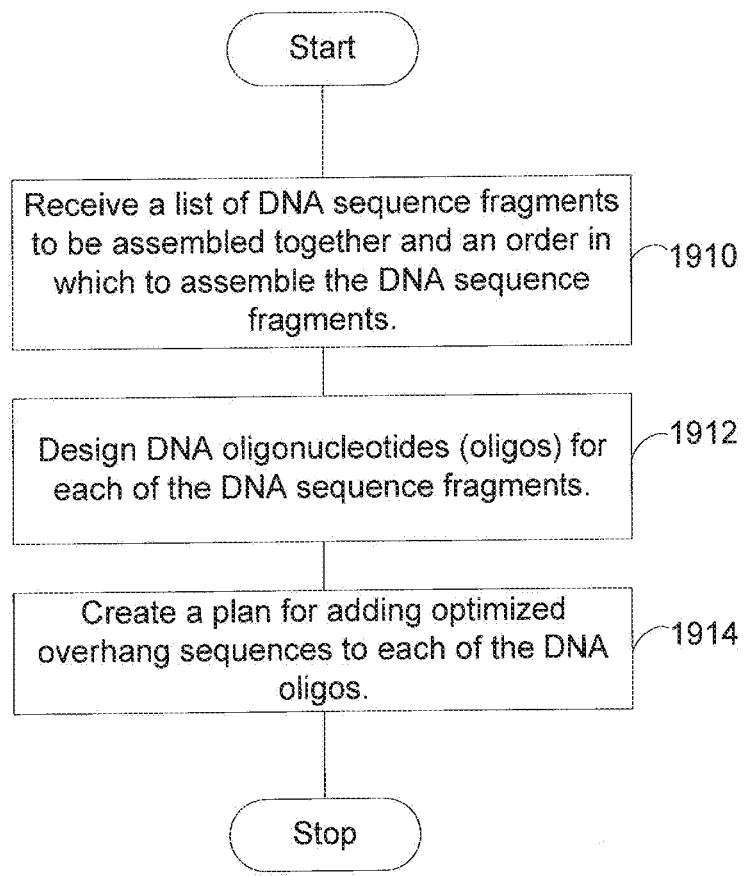
FIG. 19A-19G are flowcharts in accordance with an exemplary embodiment of the present invention.
Figure 19B:
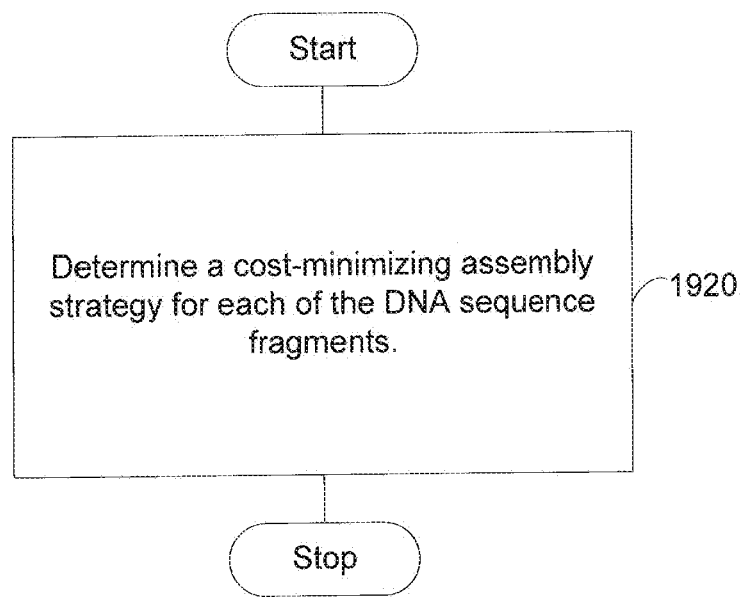

Referring to FIG. 19A, in an exemplary embodiment, the present invention includes a step 1910 of receiving a list of DNA sequence fragments to be assembled together and an order in which to assemble the DNA sequence fragments, a step 1912 of designing DNA oligonucleotides (oligos) for each of the DNA sequence fragments, and a step 1914 of creating a plan for adding optimized overhang sequences to each of the DNA oligos. Referring to FIG. 19B, in an exemplary embodiment, the present invention further includes a step 1920 of determining a cost-minimizing assembly strategy for each of the DNA sequence fragments.

Figure 19C:
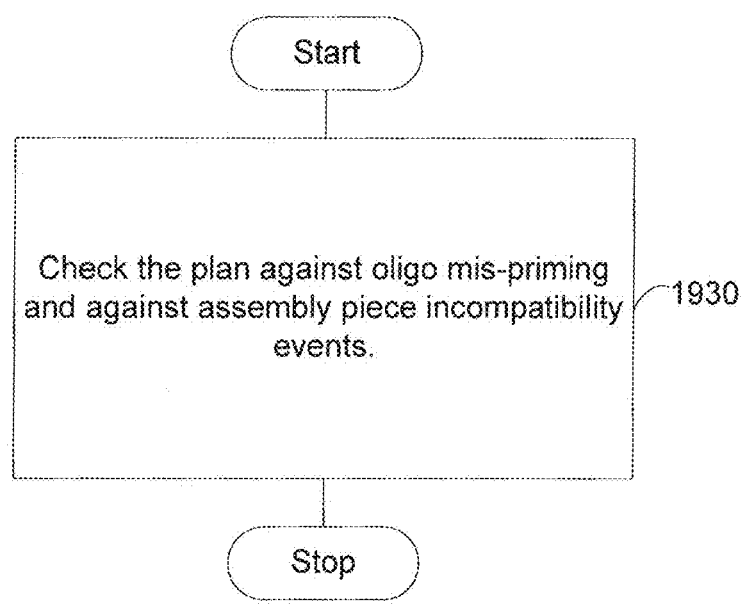
Figure 19D:
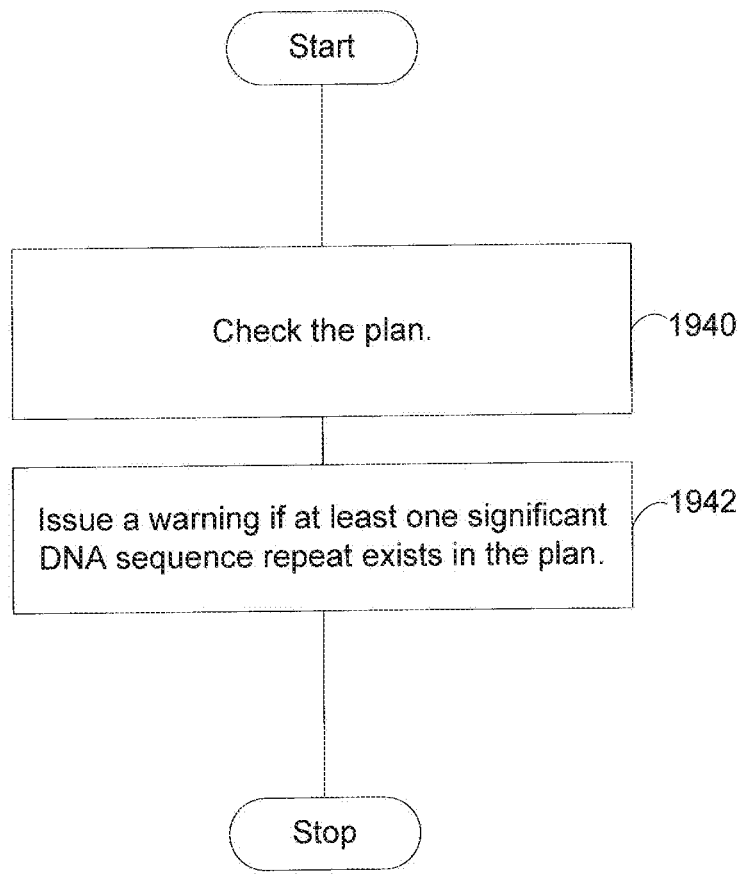
Figure 19E:
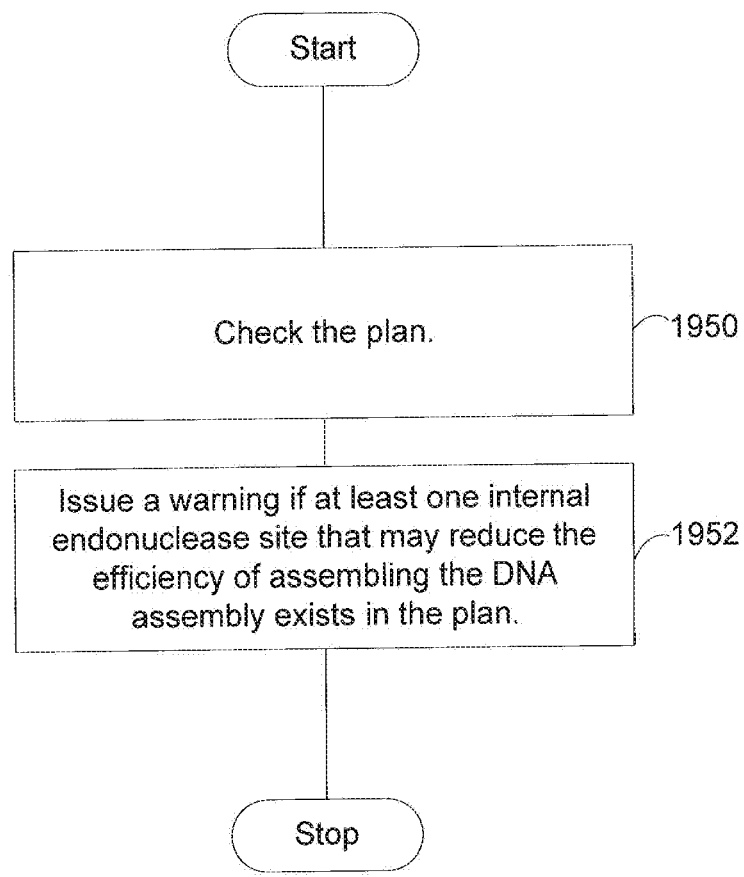

Referring to FIG. 19C, in an exemplary embodiment, the present invention further includes a step 1930 of checking the plan against oligo mis-priming and against assembly piece incompatibility events. Referring to FIG. 19D, in an exemplary embodiment, the present invention further includes a step 1940 of checking the plan and a step 1942 of issuing a warning if at least one significant DNA sequence repeat exists in the plan. Referring to FIG. 19E, in an exemplary embodiment, the present invention further includes a step 1950 of checking the plan and a step 1952 of issuing a warning if at least one internal endonuclease site that may reduce the efficiency of assembling the DNA assembly exists in the plan.

Figure 19F:
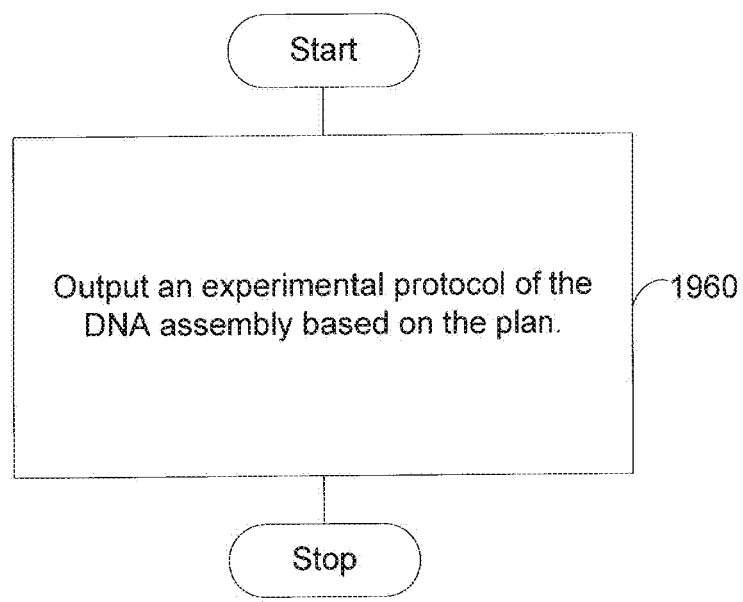
Figure 19G:
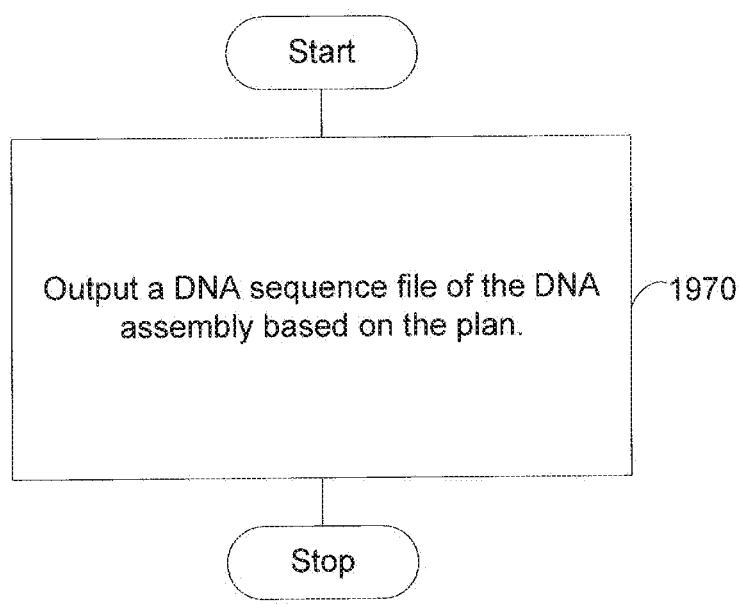

Referring to FIG. 19F, in an exemplary embodiment, the present invention further includes a step 1960 of outputting an experimental protocol of the DNA assembly based on the plan. Referring to FIG. 19O, in an exemplary embodiment, the present invention further includes a step 1970 of outputting a DNA sequence file of the DNA assembly based on the plan.

Receiving

Figure 20A:
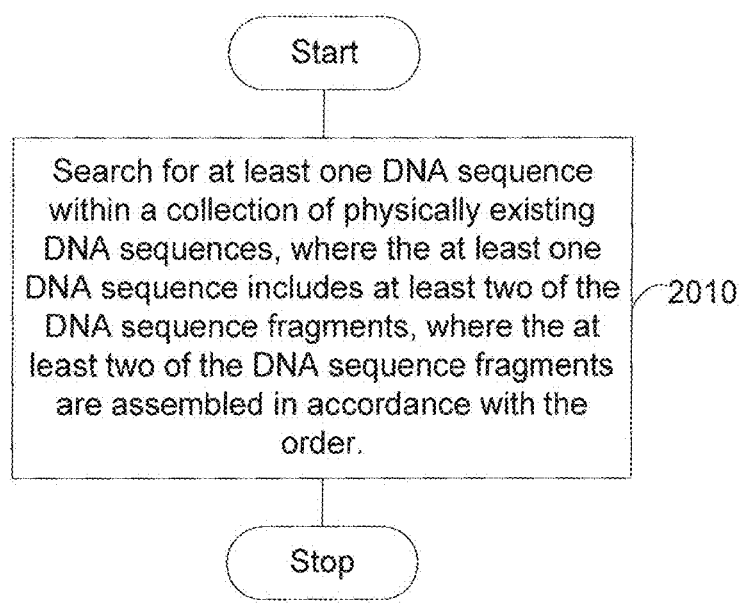
FIG. 20A-20D are flowcharts in accordance with an exemplary embodiment of the present invention.
Figure 20B:
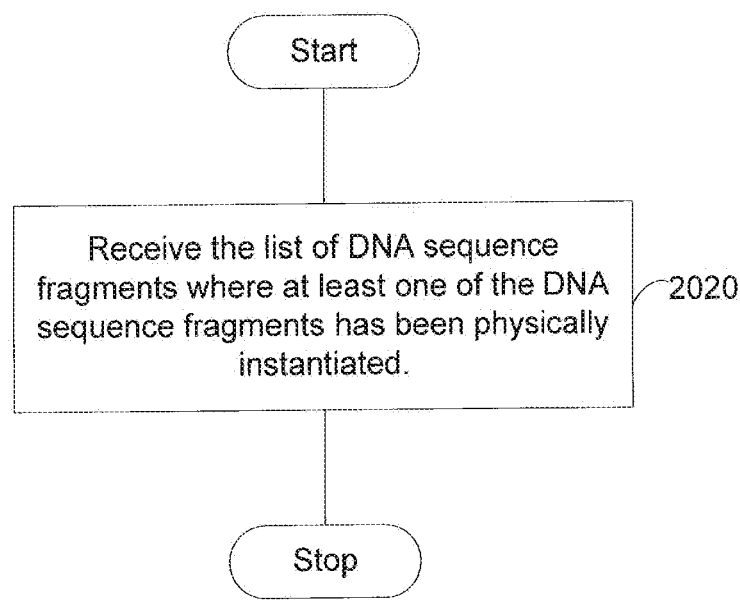
Figure 20C:
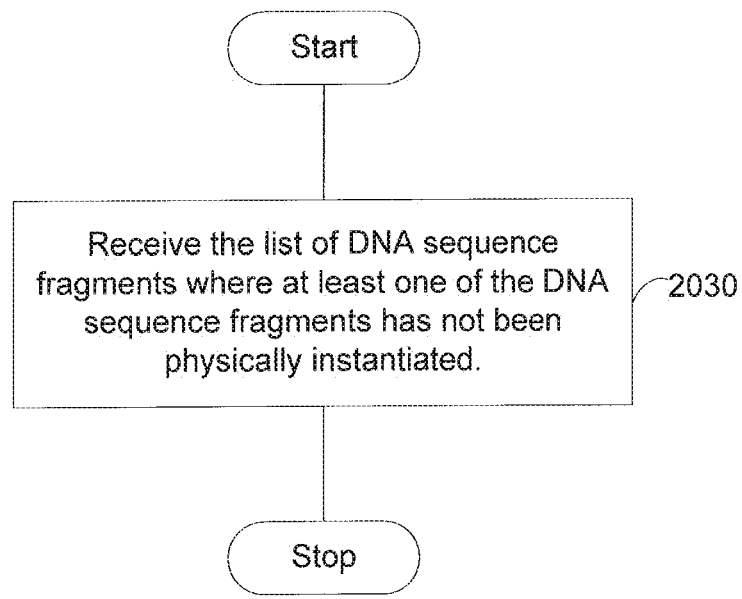
Figure 20D:
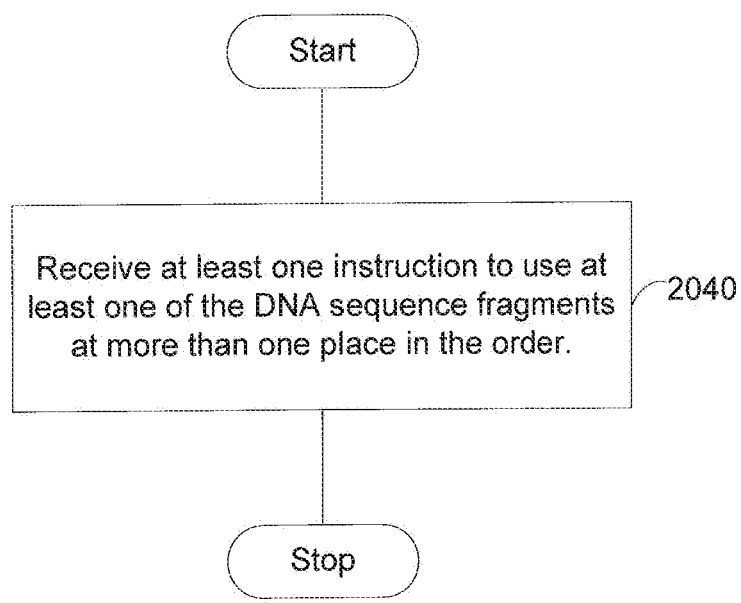

Referring to FIG. 20A, in an exemplary embodiment, receiving step 1910 further includes a step 2010 of searching for at least one DNA sequence within a collection of physically existing DNA sequences, where the at least one DNA sequence includes at least two of the DNA sequence fragments, where the at least two of the DNA sequence fragments are assembled in accordance with the order. Referring to FIG. 20B, in an exemplary embodiment, receiving step 1910 includes a step 2020 of receiving the list of DNA sequence fragments where at least one of the DNA sequence fragments has been physically instantiated. Referring to FIG. 20C, in an exemplary embodiment, receiving step 1910 includes a step 2030 of receiving the list of DNA sequence fragments where at least one of the DNA sequence fragments has not been physically instantiated. Referring to FIG. 20D, in an exemplary embodiment, receiving step 1910 includes a step 2040 of receiving at least one instruction to use at least one of the DNA sequence fragments at more than one place in the order.

Creating

Figure 21A:
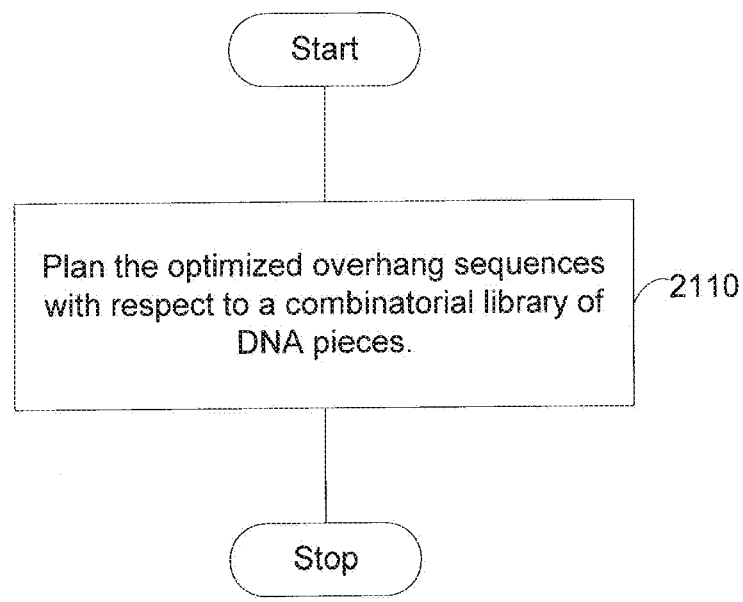
FIG. 21A-21C are flowcharts in accordance with an exemplary embodiment of the present invention.
Figure 21B:
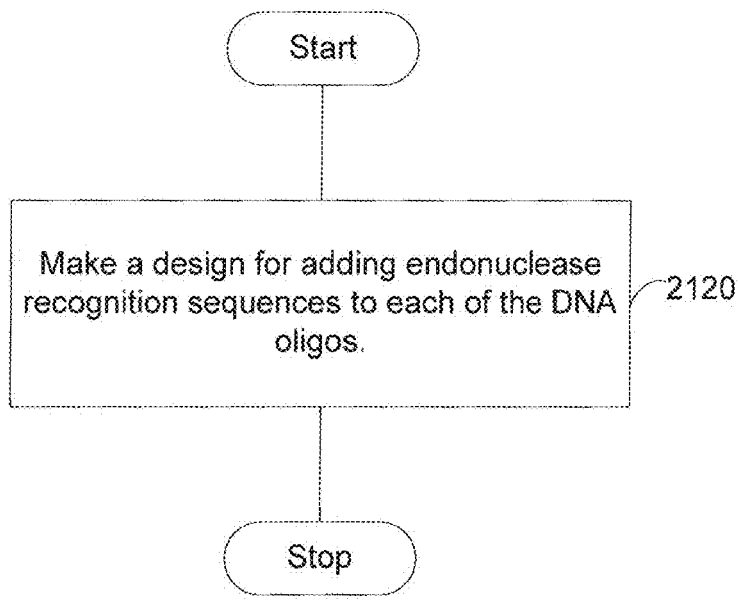
Figure 21C:
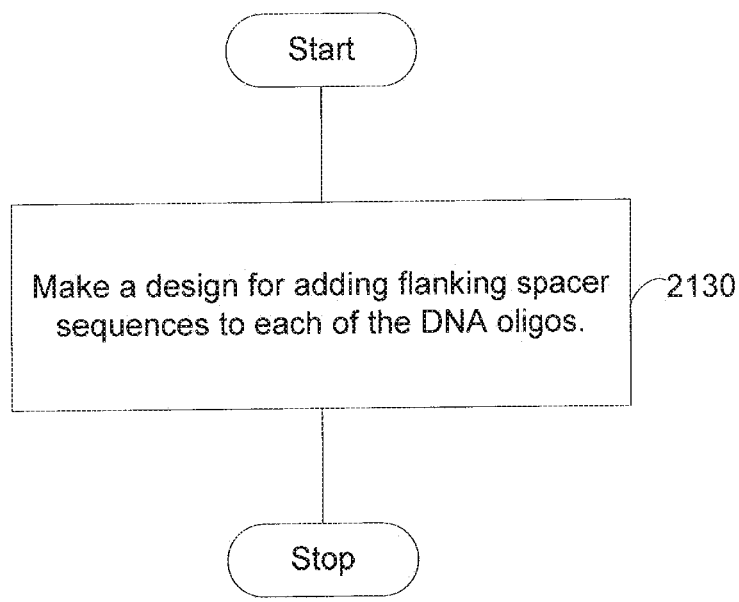

Referring to FIG. 21A, in an exemplary embodiment, creating step 1914 includes a step 2110 of planning the optimized overhang sequences with respect to a combinatorial library of DNA pieces. Referring to FIG. 21B, in an exemplary embodiment, creating step 1914 further includes a step 2120 of making a design for adding endonuclease recognition sequences to each of the DNA oligos. Referring to FIG. 21C, in an exemplary embodiment, creating step 1914 further includes a step 2130 making a design for adding flanking spacer sequences to each of the DNA oligos.

Determining

Figure 22A:
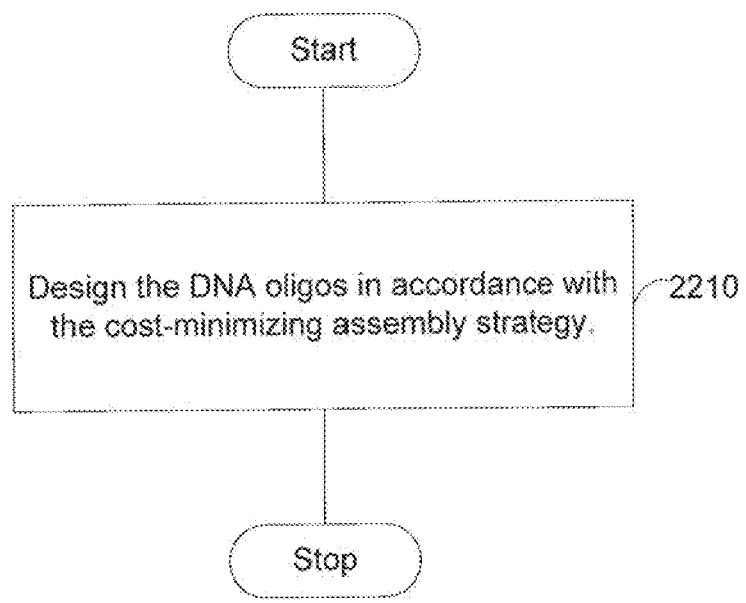
FIGS. 22A and 22B are flowcharts in accordance with an exemplary embodiment of the present invention.
Figure 22B:
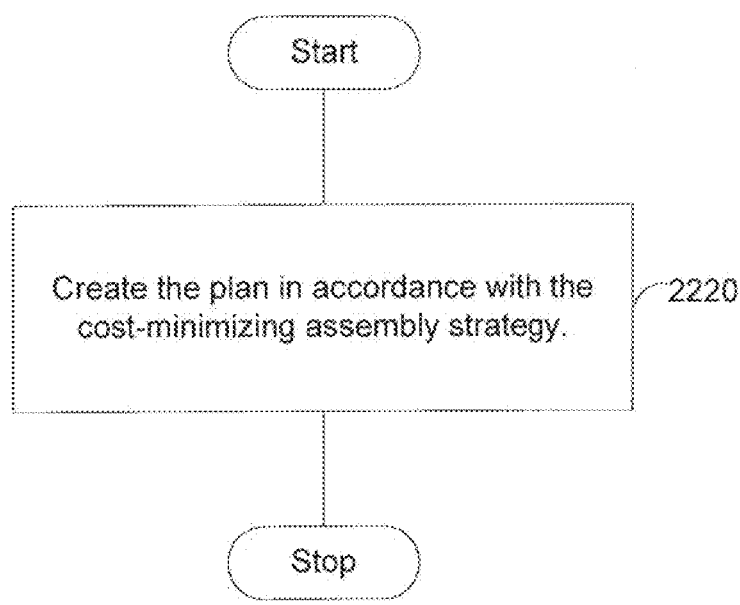

Referring to FIG. 22A, in an exemplary embodiment, determining step 1920 includes a step 2210 of designing the DNA oligos in accordance with the cost-minimizing assembly strategy. Referring to FIG. 22B, in an exemplary embodiment, determining step 1920 includes a step 2220 of creating the plan in accordance with the cost-minimizing assembly strategy.

Checking

Figure 23:
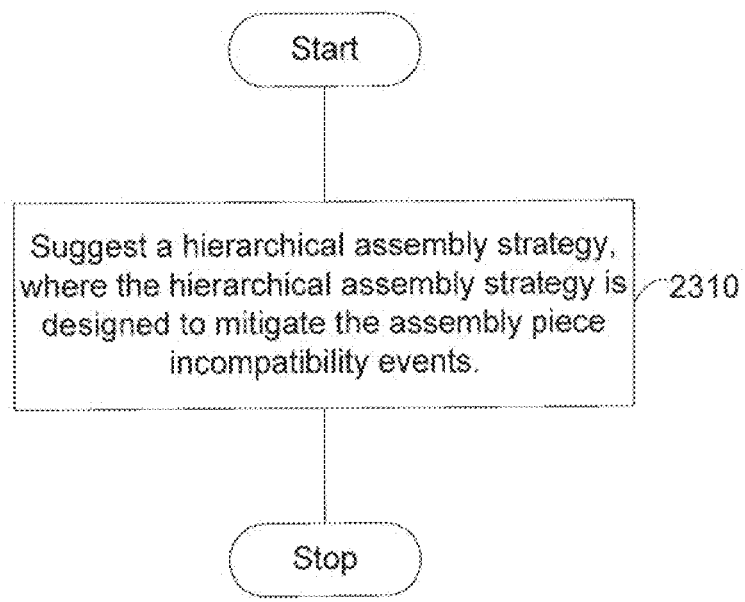
FIG. 23 is a flowchart in accordance with an exemplary embodiment of the present invention.

Referring to FIG. 23, in an exemplary embodiment, checking step 1930 further includes a step 2310 of suggesting a hierarchical assembly strategy, where the hierarchical assembly strategy is designed to mitigate the assembly piece incompatibility events.

Outputting

Figure 24A:
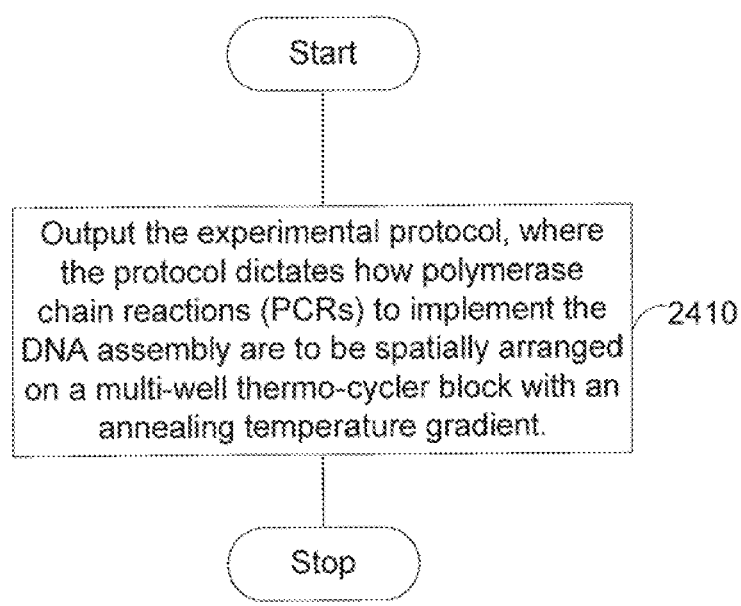
FIG. 24A-24D are flowcharts in accordance with an exemplary embodiment of the present invention.
Figure 24B:
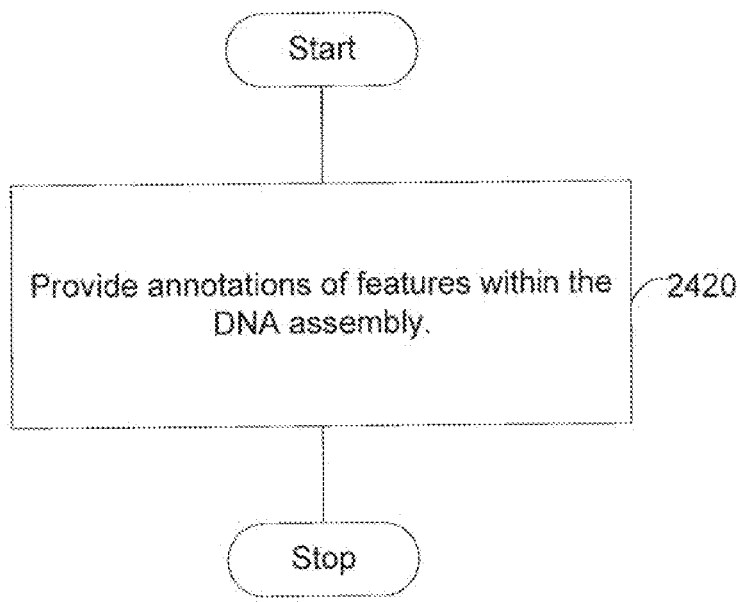

Referring to FIG. 24A, in an exemplary embodiment, outputting step 1960 includes a step 2410 of outputting the experimental protocol, where the protocol dictates how polymerase chain reactions (PCRs) to implement the DNA assembly are to be spatially arranged on a multi-well thermo-cycler block with an annealing temperature gradient. Referring to FIG. 24B, in an exemplary embodiment, outputting step 1970 further includes a step 2420 of providing annotations of features within the DNA assembly.

Figure 24C:
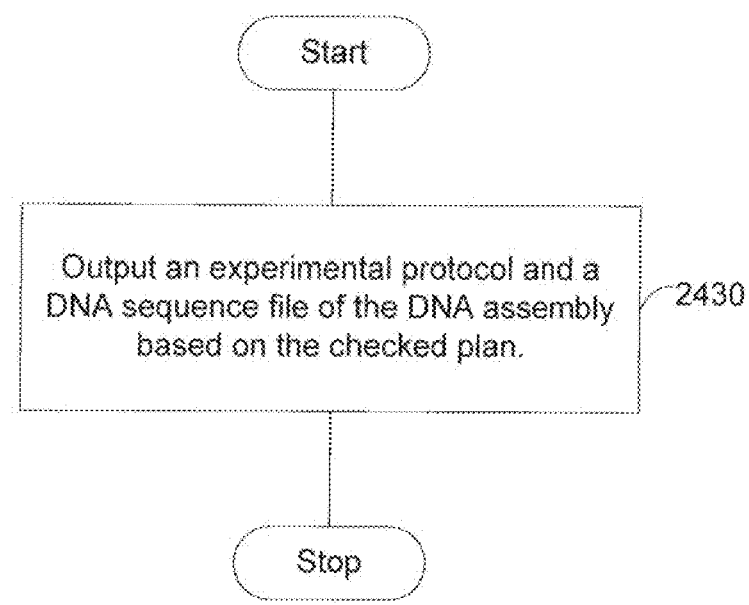

Referring to FIG. 24C, in an exemplary embodiment, checking step 1930 further includes a step 2430 of outputting an experimental protocol and a DNA sequence file of the DNA assembly based on the checked plan.

Figure 24D:
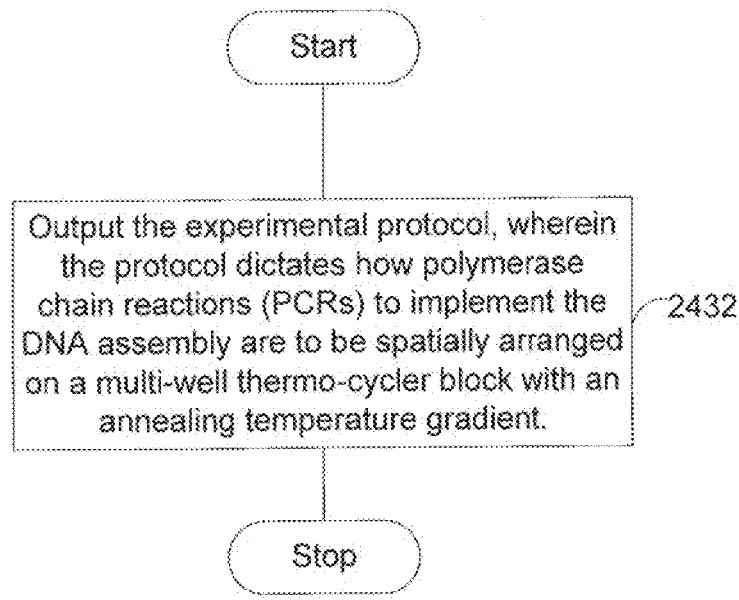

Referring to FIG. 24D, in an exemplary embodiment, outputting step 2430 includes a step 2432 of outputting the experimental protocol, wherein the protocol dictates how polymerase chain reactions (PCRs) to implement the DNA assembly are to be spatially arranged on a multi-well thermo-cycler block with an annealing temperature gradient.

Direct Synthesis Pieces and DNA Oligonucleotides (Oligos)

Figure 25A:
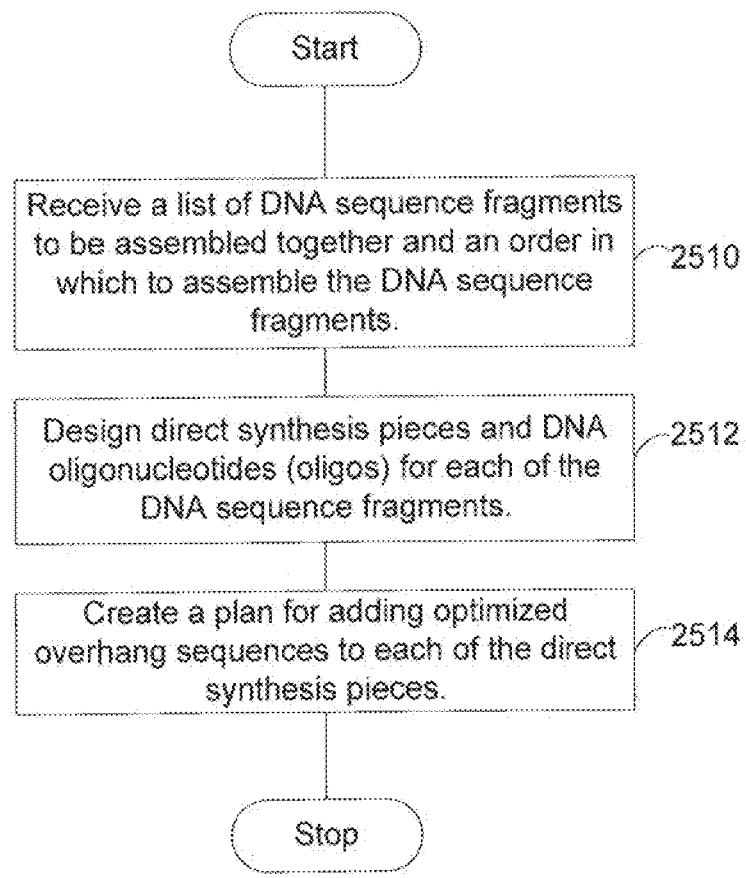
FIG. 25A-25G are flowcharts in accordance with an exemplary embodiment of the present invention.
Figure 25B:
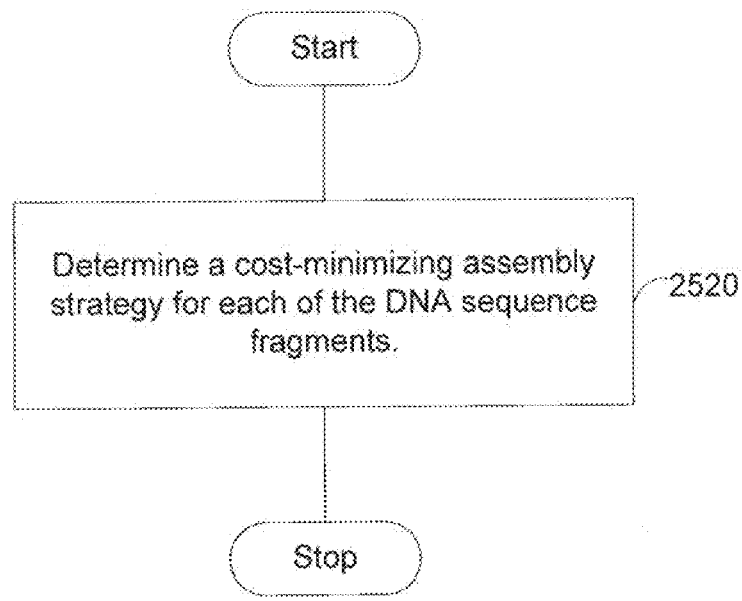

Referring to FIG. 25A, in an exemplary embodiment, the present invention includes a step 2510 of receiving a list of DNA sequence fragments to be assembled together and an order in which to assemble the DNA sequence fragments, a step 2512 of designing direct synthesis pieces and DNA oligonucleotides (oligos) for each of the DNA sequence fragments, and a step 2514 of creating a plan for adding optimized overhang sequences to each of the direct synthesis pieces. Referring to FIG. 25B, in an exemplary embodiment, the present invention further includes a step 2520 of determining a cost-minimizing assembly strategy for each of the DNA sequence fragments.

Figure 25C:
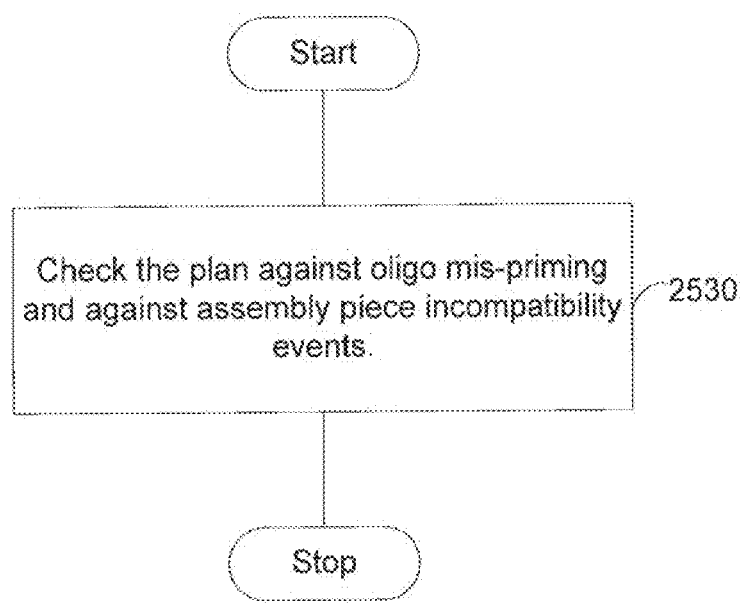
Figure 25D:
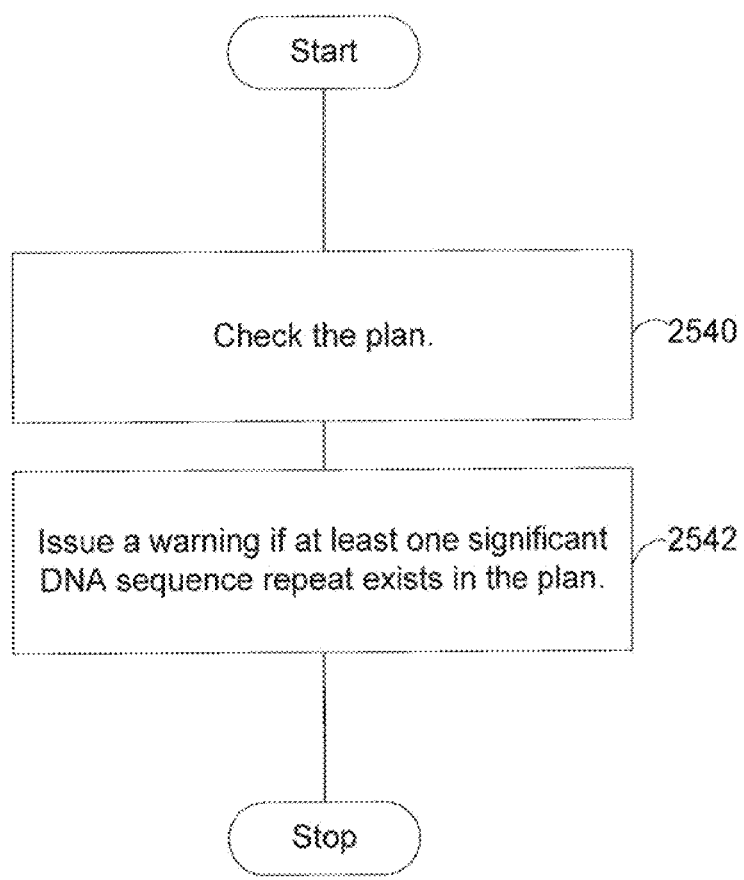
Figure 25E:
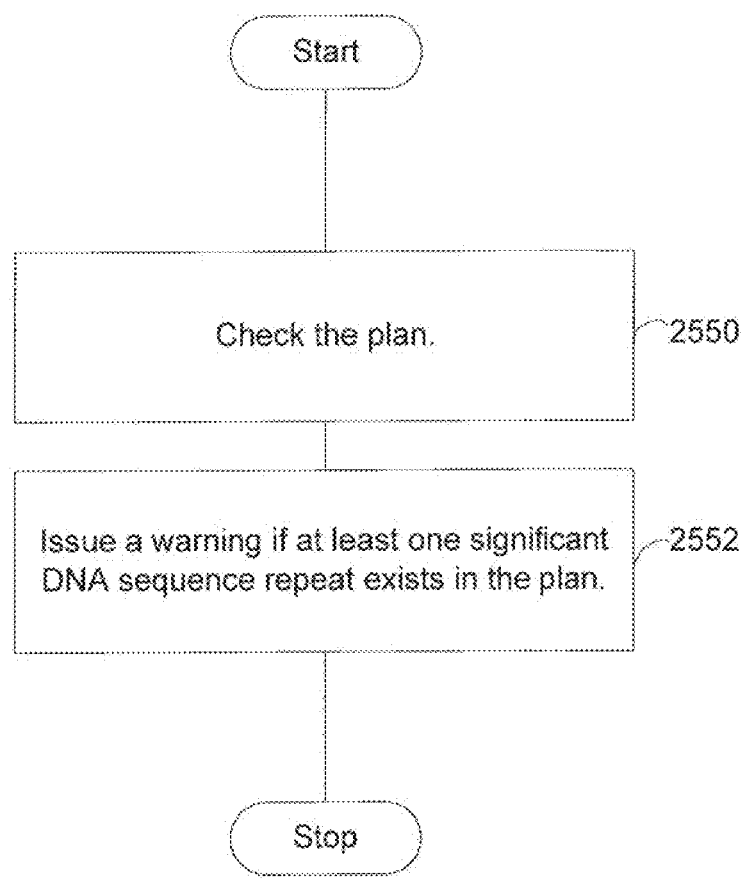

Referring to FIG. 25C, in an exemplary embodiment, the present invention further includes a step 2530 of checking the plan against oligo mis-priming and against assembly piece incompatibility events. Referring to FIG. 25D, in an exemplary embodiment, the present invention further includes a step 2540 of checking the plan and a step 2542 of issuing a warning if at least one significant DNA sequence repeat exists in the plan. Referring to FIG. 25E, in an exemplary embodiment, the present invention further includes a step 2550 of checking the plan and a step 2552 of issuing a warning if at least one internal endonuclease site that may reduce the efficiency of assembling the DNA assembly exists in the plan.

Figure 25F:
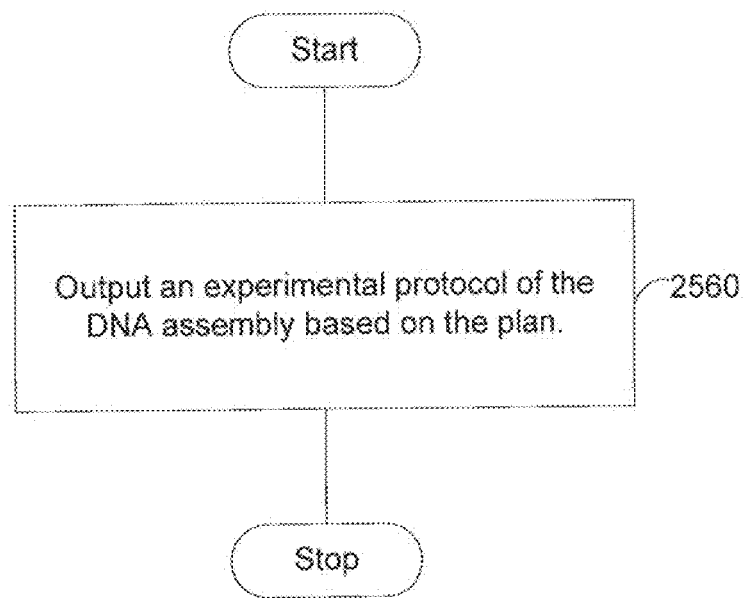
Figure 25G:
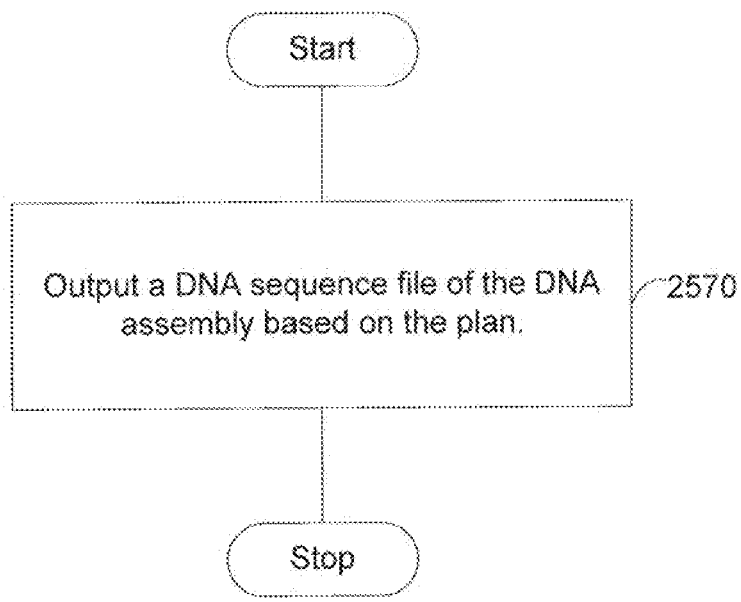

Referring to FIG. 25F, in an exemplary embodiment, the present invention further includes a step 2560 of outputting an experimental protocol of the DNA assembly based on the plan. Referring to FIG. 25G, in an exemplary embodiment, the present invention further includes a step 2570 of outputting a DNA sequence file of the DNA assembly based on the plan.

Receiving

In an exemplary embodiment, receiving step 2510 further includes a step of searching for at least one DNA sequence within a collection of physically existing DNA sequences, where the at least one DNA sequence includes at least two of the DNA sequence fragments, where the at least two of the DNA sequence fragments are assembled in accordance with the order. In an exemplary embodiment, receiving step 2510 includes a step of receiving the list of DNA sequence fragments where at least one of the DNA sequence fragments has been physically instantiated. In an exemplary embodiment, receiving step 2510 includes a step of receiving the list of DNA sequence fragments where at least one of the DNA sequence fragments has not been physically instantiated. In an exemplary embodiment, receiving step 2510 includes a step of receiving at least one instruction to use at least one of the DNA sequence fragments at more than one place in the order.

Creating

In an exemplary embodiment, creating step 2514 includes a step of planning the optimized overhang sequences with respect to a combinatorial library of DNA pieces. In an exemplary embodiment, creating step 2514 further includes a step of making a design for adding endonuclease recognition sequences to each of the direct synthesis pieces. In an exemplary embodiment, creating step 2514 further includes a step of making a design for adding flanking spacer sequences to each of the direct synthesis pieces.

Determining

In an exemplary embodiment, determining step 2520 includes a step of designing the direct synthesis pieces and the DNA oligos in accordance with the cost-minimizing assembly strategy. In an exemplary embodiment, determining step 2520 includes a step of creating the plan in accordance with the cost-minimizing assembly strategy.

Checking

In an exemplary embodiment, checking step 2530 further includes a step of suggesting a hierarchical assembly strategy, where the hierarchical assembly strategy is designed to mitigate the assembly piece incompatibility events.

Outputting

In an exemplary embodiment, outputting step 2560 includes a step of outputting the experimental protocol, wherein the protocol dictates how polymerase chain reactions (PCRs) to implement the DNA assembly are to be spatially arranged on a multi-well thermo-cycler block with an annealing temperature gradient. In an exemplary embodiment, outputting step 2570 further includes a step of providing annotations of features within the DNA assembly.

In an exemplary embodiment, checking step 2530 further includes a step of outputting an experimental protocol and a DNA sequence file of the DNA assembly based on the checked plan.

In an exemplary embodiment, the outputting includes a step of outputting the experimental protocol, wherein the protocol dictates how polymerase chain reactions (PCRs) to implement the DNA assembly are to be spatially arranged on a multi-well thermo-cycler block with an annealing temperature gradient.

DNA Oligonucleotides (Oligos) and Direct Synthesis Pieces

Figure 26A:
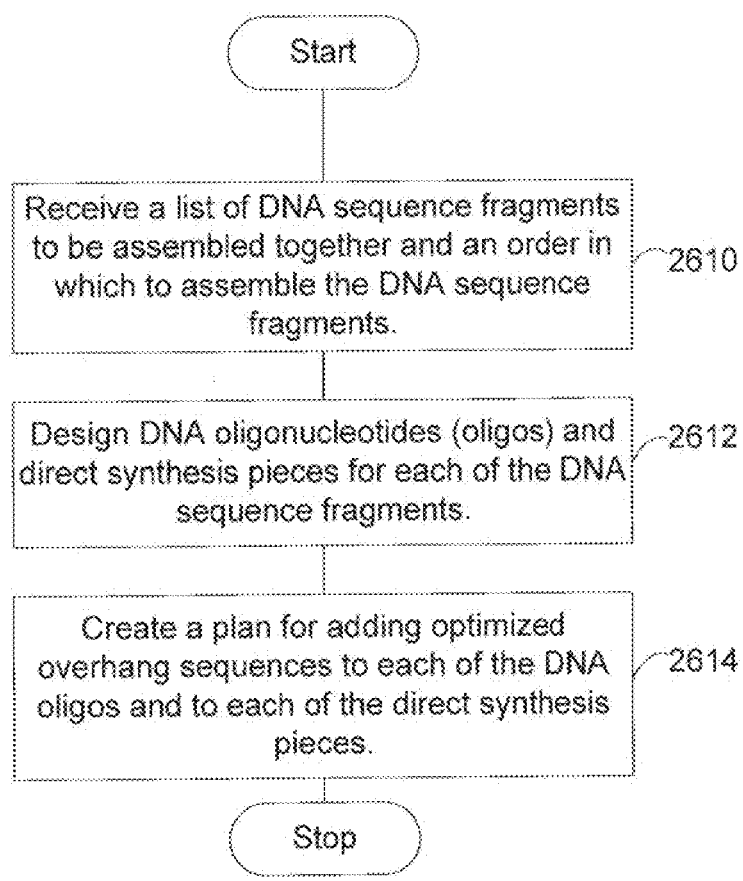
FIG. 26A-26G are flowcharts in accordance with an exemplary embodiment of the present invention.
Figure 26B:
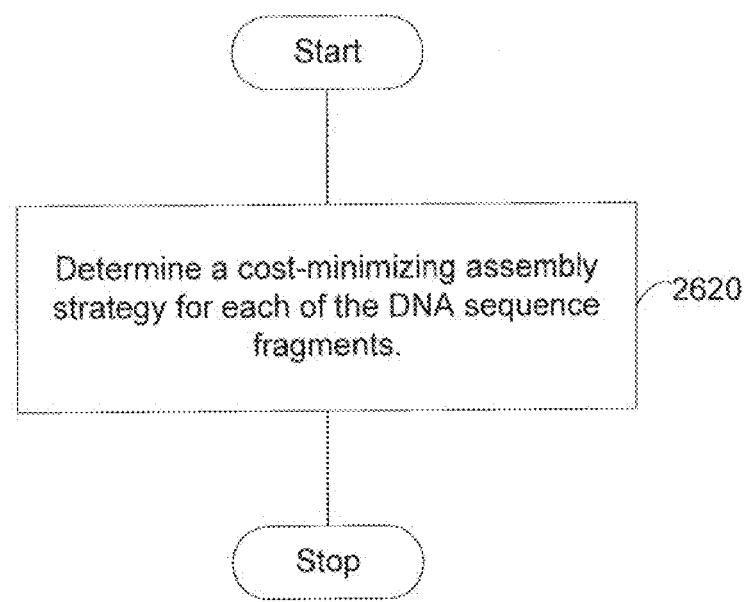

Referring to FIG. 26A, in an exemplary embodiment, the present invention includes a step 2610 of receiving a list of DNA sequence fragments to be assembled together and an order in which to assemble the DNA sequence fragments, a step 2612 of designing DNA oligonucleotides (oligos) and direct synthesis pieces for each of the DNA sequence fragments, and a step 2614 of creating a plan for adding optimized overhang sequences to each of the DNA oligos and to each of the direct synthesis pieces. Referring to FIG. 26B, in an exemplary embodiment, the present invention further includes a step 2620 of determining a cost-minimizing assembly strategy for each of the DNA sequence fragments.

Figure 26C:
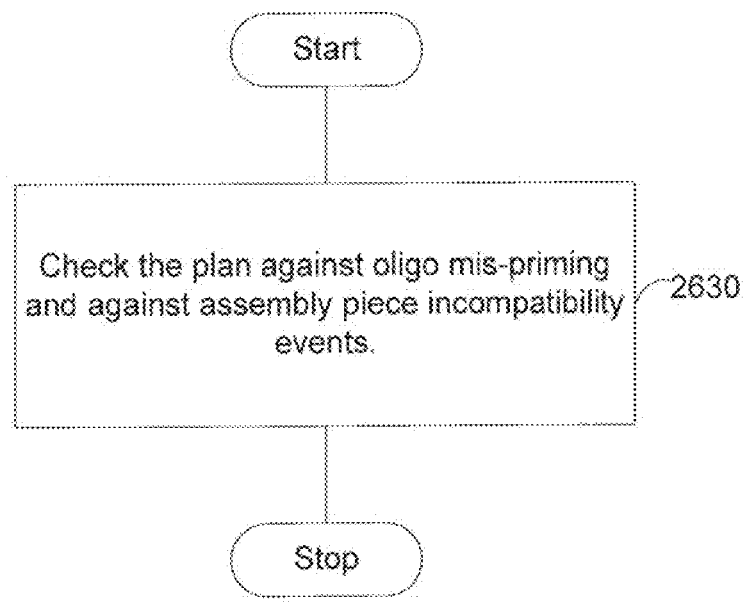
Figure 26D:
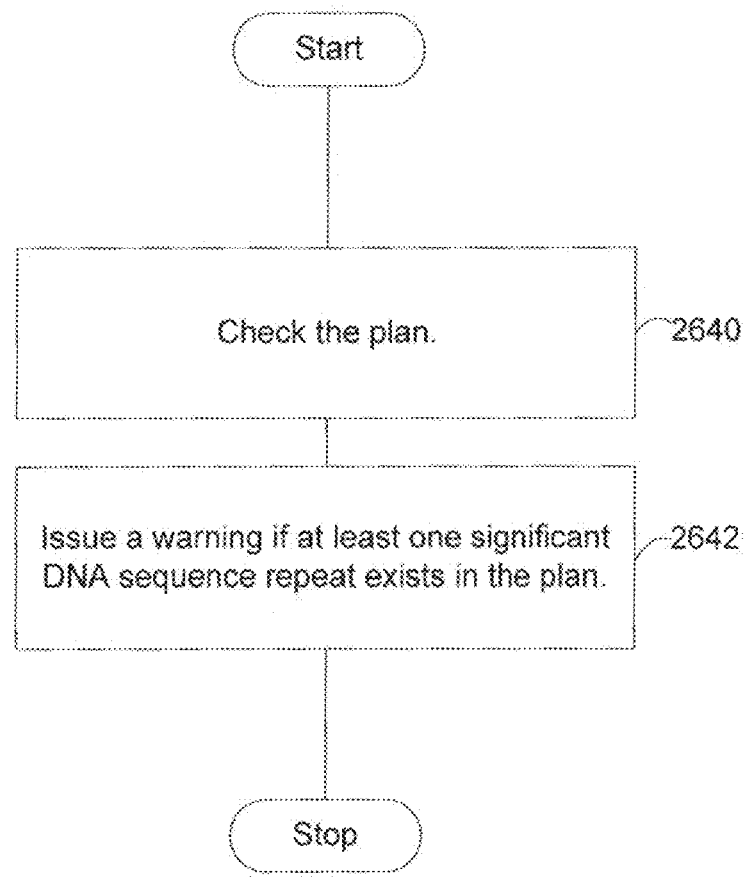
Figure 26E:
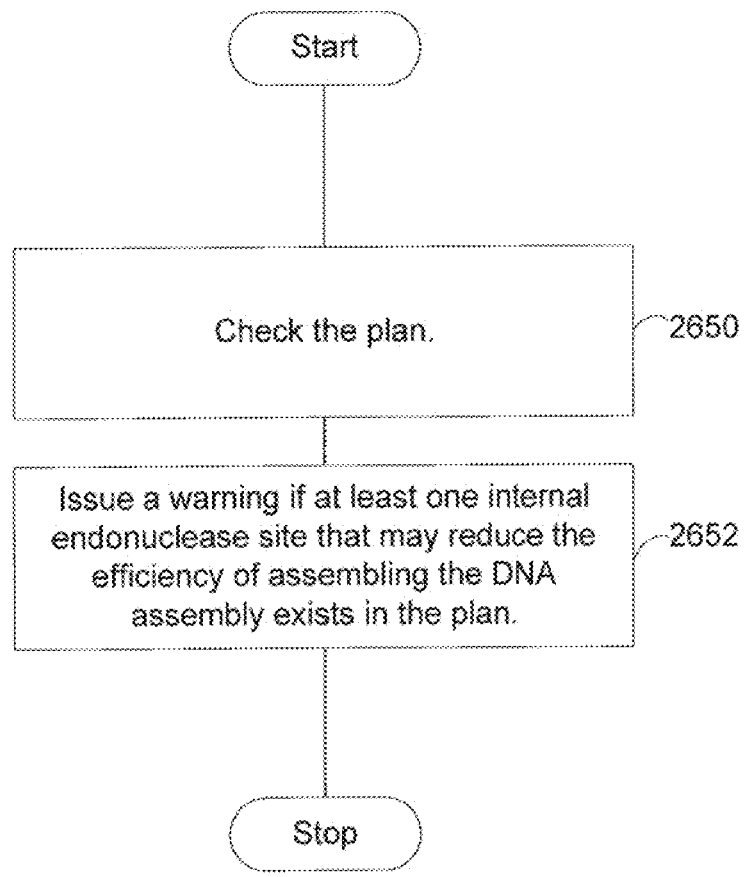

Referring to FIG. 26C, in an exemplary embodiment, the present invention further includes a step 2630 of checking the plan against oligo mis-priming and against assembly piece incompatibility events. Referring to FIG. 26D, in an exemplary embodiment, the present invention further includes a step 2640 of checking the plan and a step 2642 of issuing a warning if at least one significant DNA sequence repeat exists in the plan. Referring to FIG. 26E, in an exemplary embodiment, the present invention further includes a step 2650 of checking the plan and a step 2652 of issuing a warning if at least one internal endonuclease site that may reduce the efficiency of assembling the DNA assembly exists in the plan.

Figure 26F:
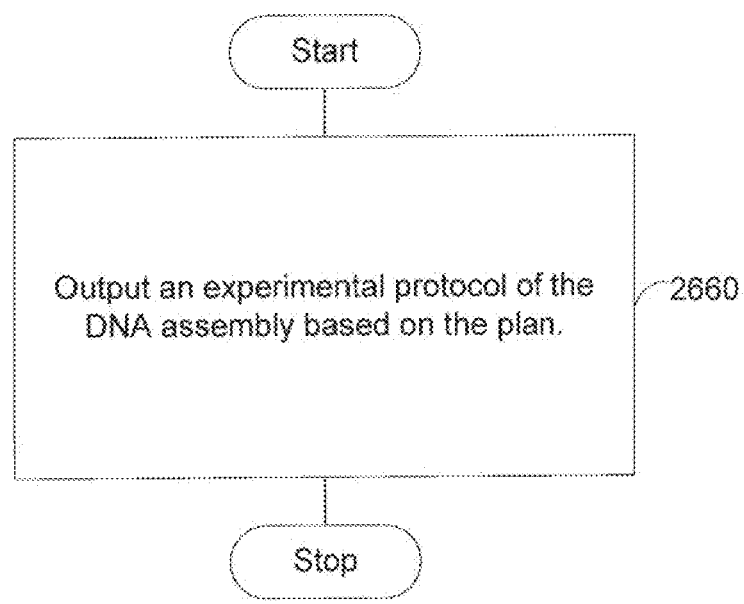
Figure 26G:
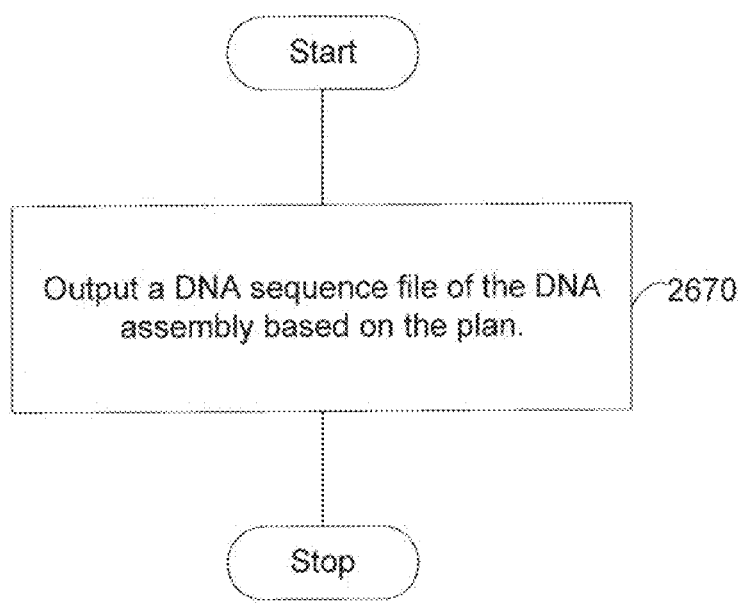

Referring to FIG. 26F, in an exemplary embodiment, the present invention further includes a step 2660 of outputting an experimental protocol of the DNA assembly based on the plan. Referring to FIG. 26G, in an exemplary embodiment, the present invention further includes a step 2670 of outputting a DNA sequence file of the DNA assembly based on the plan.

Receiving

In an exemplary embodiment, receiving step 2610 further includes a step of searching for at least one DNA sequence within a collection of physically existing DNA sequences, where the at least one DNA sequence includes at least two of the DNA sequence fragments, where the at least two of the DNA sequence fragments are assembled in accordance with the order.

In an exemplary embodiment, receiving step 2610 includes a step of receiving the list of DNA sequence fragments where at least one of the DNA sequence fragments has been physically instantiated.

In an exemplary embodiment, receiving step 2610 includes a step of receiving the list of DNA sequence fragments where at least one of the DNA sequence fragments has not been physically instantiated.

In an exemplary embodiment, receiving step 2610 includes a step of receiving at least one instruction to use at least one of the DNA sequence fragments at more than one place in the order.

Creating

In an exemplary embodiment, creating step 2614 includes a step of planning the optimized overhang sequences with respect to a combinatorial library of DNA pieces. In an exemplary embodiment, creating step 2614 further includes a step of making a design for adding endonuclease recognition sequences to each of the DNA oligos and to each of the direct synthesis pieces. In an exemplary embodiment, creating step 2614 further includes a step of making a design for adding flanking spacer sequences to each of the DNA oligos and to each of the direct synthesis pieces.

Determining

In an exemplary embodiment, determining step 2620 includes a step of designing the DNA oligos and the direct synthesis pieces in accordance with the cost-minimizing assembly strategy. In an exemplary embodiment, determining step 2620 includes a step of creating the plan in accordance with the cost-minimizing assembly strategy.

Checking

In an exemplary embodiment, checking step 2630 further includes a step of suggesting a hierarchical assembly strategy, where the hierarchical assembly strategy is designed to mitigate the assembly piece incompatibility events.

Outputting

In an exemplary embodiment, outputting step 2660 includes a step of outputting the experimental protocol, where the protocol dictates how polymerase chain reactions (PCRs) to implement the DNA assembly are to be spatially arranged on a multi-well thermo-cycler block with an annealing temperature gradient. In an exemplary embodiment, outputting step 2670 further includes a step of providing annotations of features within the DNA assembly.

In an exemplary embodiment, checking step 2630 further includes a step of outputting an experimental protocol and a DNA sequence file of the DNA assembly based on the checked plan.

In an exemplary embodiment, the outputting includes a step of outputting experimental protocol, wherein the protocol dictates how polymerase chain reactions (PCRs) to implement the DNA assembly are to be spatially arranged on a multi-well thereto-cycler block with an annealing temperature gradient.

EXAMPLE

The invention will be described in greater detail by way of a specific example. The following example is offered for illustrative purposes, and is intended neither to limit nor define the invention in any manner.

SLIC/Gibson/CPEC Assembly Design

In an exemplary embodiment, the present invention allows for the definition of the biological parts (sequences) to be assembled. Since the present invention designs for the SLIC/Gibson/CPEC assembly methods using flanking homology sequences and Golden-gate assembly methods using optimized overhang sequences that are largely sequence independent, the defined parts do not need to be "packaged" in any particular format (as would be required for BioBricks, for example).

FIG. 27A depicts a typical list of defined parts, where the list would have been defined in a parts list input file to be received by the present invention. In essence, a part is merely defined by a start and end base pair within a source sequence, and by its location on the top or bottom (reverse complement) strand.

Following the definitions of the parts to be assembled, in an exemplary embodiment, the present invention receives the order and direction (forward or reverse) of each of the parts to be assembled together in the final target construct. FIG. 27B depicts a typical list of ordered parts to be assembled, where the order and direction of each part would have been defined in a target part order list input file to be received by the present invention in this example assembly, the vector backbone (the very first part in the list) would be restriction digest linearized to yield the first assembly piece. The primary advantages of using a digest linearized vector backbone (over PCR amplification) are that PCR amplification of a (potentially) long vector backbone sequence would not be required, and point mutations that may be introduced into the vector backbone during PCR amplification would not be a concern. As a consequence, deep sequencing into the digest linearized vector backbone would not be required (although sequence verification of the vector backbone junctions with the other assembly pieces would still be necessary).

The main disadvantages of a restriction digest linearized vector backbone are that, first and foremost, it would require a (unique) cut-site which diminishes the sequence-independence of the assembly process, and second that it would place the entire SLIC/Gibson/CPEC sequence homology/overlap burden on the adjacent assembly pieces. For example, the 5' end of the first DNA part would have to be flanked to follow the digest linearized vector backbone (in this specific example, the 3' end of the atfA gene) with the entire homology region (e.g., the last 26 bps of the linearized vector backbone).

If, in contrast, the vector backbone were to be PCR-amplified, the SLIC/Gibson/CPEC sequence homology/overlap burden could be shared more equally between the linearized vector backbone and the neighboring assembly pieces (e.g., flanking only about 13 bps of homology sequence to the ends of the linearized vector backbone and first assembly pieces), and a cut-site to linearize the backbone would not be required.

In an exemplary embodiment, the present invention finds the most cost-effective assembly design, where the parameters used in the cost analysis are defined in a parameters file to be received by the present invention. While the present invention allows for specifying a strategy for each part (such as dictating that the vector backbone will be digest linearized in this particular example, the present invention has to determine for all parts with unspecified strategy if direct DNA synthesis, PCR/SOE, or oligo embedding is the best approach from a cost standpoint. In this particular example, with the exception of the digested vector backbone, all of the larger parts would be PCR amplified, the intermediate parts (too small for direct Gibson assembly) would be PCR amplified and then SOE'd together with neighboring parts until a sufficient assembly piece size is obtained (e.g., ~250 bp), and the very small parts would be directly embedded into the primers that amplify the intermediate or large parts. While direct DNA synthesis is not cost effective in this particular example, direct synthesis could be used by the present invention for other assemblies.

FIG. 28 depicts a typical list of DNA oligos to be used in an assembly, where the designed oligos would be appended to a master oligos list file by the present invention.

In an exemplary embodiment, the present invention utilizes the Primer3 primer design program in the oligo design process, using design parameters (such as the target Tm) defined in the parameters file received by the present invention. In an exemplary embodiment, the present invention design the following two types of primers, (1) "pure" primers that anneal perfectly to the template sequence and (2) full-length primers that contain a 5' SLIC/Gibson/CPEC flanking homology sequence, followed by the identical sequence of the corresponding "pure" primer.

In an alternative embodiment, the present invention allows for SOE'ing together the flanking sequences to the 5' and 3' termini of the fragment to be assembled. This could be highly desirable, for example, when designing a protocol for in-vivo yeast assembly using the DNA assembler approach (See Shao[12].), which may require long homology sequences (up to several hundreds of bp) which are too long to embed directly into a DNA oligo primer. In addition, in some instances, it could be desirable to use SLIC/Gibson/CPEC to assemble (in several PCR-amenable fragments) extremely long physically existing sequences (e.g., a metabolic pathway that is over 10 kb and has already been cloned, or is present in genomic DNA) into additional constructs. In this particular case, it would be possible to overlap PCR products to generate the necessary flanking homology overlaps, and it would not be necessary, then, to include the flanking homology sequences into the DNA oligos nor flank them onto the assembly piece by SOE'ing. The present invention supports the design of DNA assembler (in-vivo yeast assembly) protocols as well as for exploiting the flanking homology sequence that already is present in long physically available sequences.

While PCR amplifying the template sequence directly with full-length primers is generally effective, there are instances where a two-step process, first amplifying the template with "pure" primers and then reamplifying the resulting PCR product with the full-length primers, could yield superior results. In an exemplary embodiment, the present invention automatically names the oligos (with an iterative numbering scheme, based on the part(s) that the oligo anneals to and whether or not the primer is "pure") and checks to see if the designed oligo is already present in an oligo collection (e.g., of a user of the present invention), defined by a master oligos list file received by the present invention. In this particular example, as shown in FIG. 28, the oligos highlighted in red were already included in the oligo collection, and the previously ordered oligos would be re-used, adding no additional cost to the assembly process.

In the case of either Gibson or CPEC assembly, since flanking SLIC/Gibson/CPEC homology sequences at the termini of the assembly pieces serve to prime neighboring assembly pieces for polymerase extension, in an exemplary embodiment, the present invention additionally uses the Primer3 primer program to design the 5' SLIC/Gibson/CPEC flanking homology sequence portions of the full-length oligos.

During the primer design process, if Primer3 is unable to find an acceptable set of primers, in an exemplary embodiment, the present invention relieves Primer3 of the primer design constraints that are leading to the rejection of all considered primers (e.g., minimum Tin and self-complementary constraints), while still preferring primers that minimize the violation of design constraints.

In an exemplary embodiment, the present invention utilizes BLAST (b12seq) to check for probable mis-priming events that exceed a minimum Tm threshold, as specified in the parameters file received by the present invention.

With all of the direct DNA synthesis pieces and DNA oligos designed, in an exemplary embodiment, the present invention then outputs the PCR reactions that are required to generate the DNA fragments to be assembled together. FIG. 29A depicts a typical list of PCR reactions outputted by the present invention.

In this particular example, as show in FIG. 29A, the PCR reactions in the first half of the list use "pure" primers, and those in the second half of the list use full-length primers. The primary sequence templates of the PCR reactions in the second half of the list are the corresponding "pure" PCR reaction products. In an exemplary embodiment, the present invention suggests that the full-length PCR reactions can alternatively use plasmid templates directly, forgoing the "pure" reactions altogether. If the resulting PCR product size is smaller than the minimum required for Gibson assembly, defined in the parameters file received by the present invention, in an exemplary embodiment, the present invention annotates the PCR reaction as "SOE", indicating that this PCR product should be SOE'd together with neighboring assembly pieces until the minimum Gibson fragment size is achieved. Since neighboring assembly pieces already contain flanking homology sequences, and the requisite external primers are included in the list of designed oligos in FIG. 29A, this SOE'ing process would require no additional design or new oligos.

In an exemplary embodiment, the present invention then details the resulting DNA pieces that will be assembled together. FIG. 29B depicts is a typical list of assembly pieces as outputted by the present invention. In an exemplary embodiment, the present invention provides the number of base pairs of flanking homology sequence shared between neighboring assembly pieces (relevant to SLIC and Gibson assembly) and the Tms of annealing to their neighboring assembly pieces (relevant to CPEC assembly).

In an exemplary embodiment, the present invention also identifies SLIC/Gibson/CPEC assembly piece incompatibilities. Since DNA assembly is directed by the flanking homology sequences at the termini of the assembly pieces, the present invention checks to make sure that two different assembly pieces do not have the same flanking homology sequence. In the case of CPEC, the present invention makes sure that flanking homology sequence termini do not anneal to the internal sections of any of the assembly pieces. In an exemplary embodiment, the present invention utilizes BLAST (bl2seq) to check for probable mis-annealing events that exceed a minimum Tm threshold, as specified in the parameters file received by the present invention.

Figure 30:
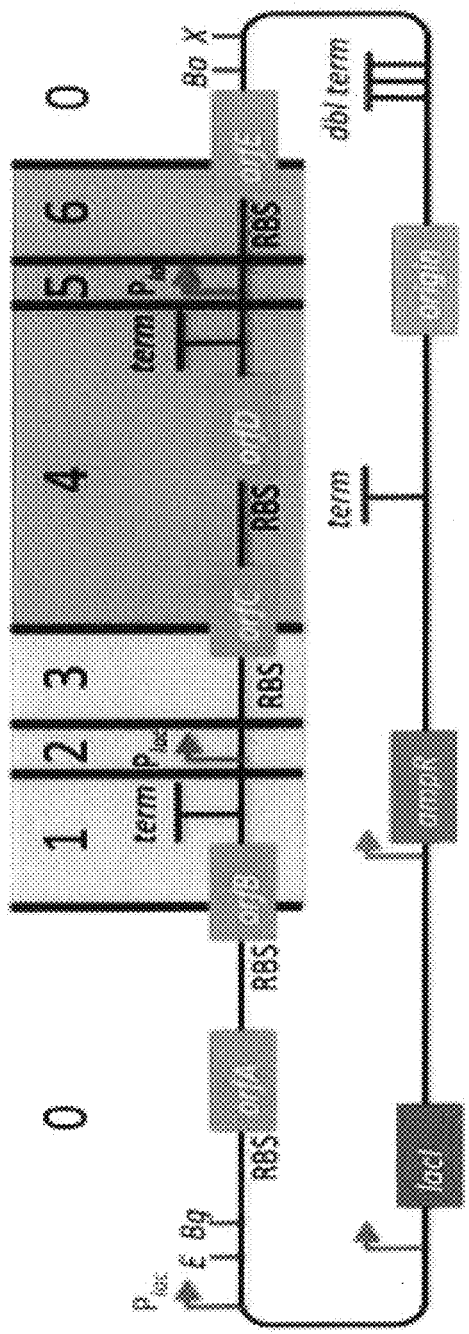
FIG. 30 shows data in accordance with the present invention.

In this particular example, there are incompatibilities amongst the set of assembly pieces, as is often the case when part(s) are used repetitively in the same assembly. Specifically, in this example, the Plac promoter part is used twice, and the Plac sequence is also found within the vector backbone. In this particular example, since the 5' ends of assembly pieces 2 and 5 are identical, assembly piece 1 might end up partnering with either assembly piece 2 or 5, resulting in undesired assembly products. In an exemplary embodiment, the present invention identifies these incompatibilities, and suggests a hierarchical assembly process, namely assembling pieces 1, 2 and 3 together, and separately 4, 5, and 6 together, as a preliminary step. The present invention then allows for piece 0 (white) to be assembled together with the contiguous piece containing 1, 2 and 3 (light grey), and with the contig containing 4, 5 and 6 (dark grey), as shown in FIG. 30. FIG. 30 depicts the list of assembly piece incompatibilities for this particular example, as identified by the present invention, and a suggested hierarchical assembly, as suggested by the present invention.

Figure 31:
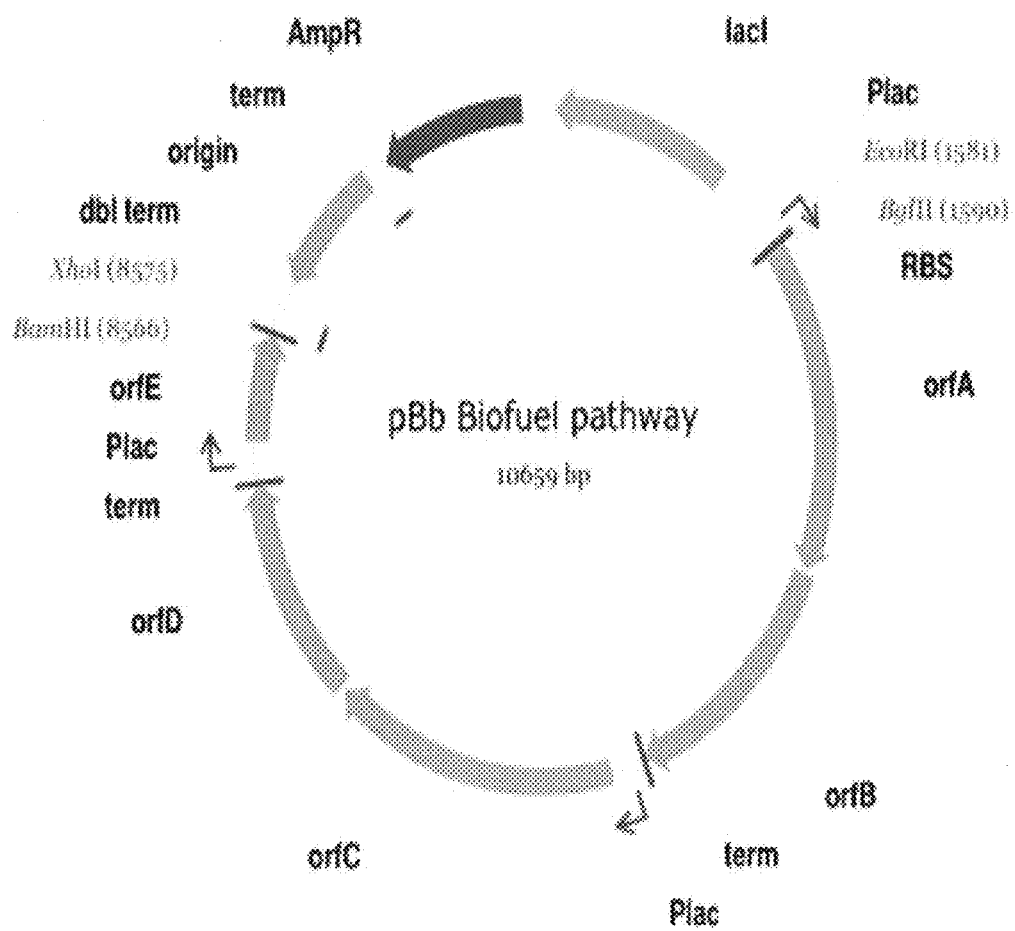
FIG. 31 shows data in accordance with the present invention.

In an exemplary embodiment, the present invention next prepares an annotated sequence file for the resulting assembly. Any feature annotations found within the sequence files going in to the assembly are correspondingly preserved in the resulting assembled sequence file by the present invention. FIG. 31 depicts a map of the resulting designed assembly for this particular example. The resulting annotated sequence file and corresponding plasmid map outputted by the present invention provides a quick way to check that the desired assembly would be the assembly to be assembled.

Combinatorial Golden-Gate Assembly Design

The present invention designs Golden-gate assemblies, using optimized overhang sequences, in a similar fashion to the present invention's designing a SLIC/Gibson/CPEC assembly. The key distinction between the two respective design processes, as shown in FIG. 2 and FIG. 18, is that whereas, for SLIC/Gibson/CPEC, the present invention uses sequence homology at the termini of the assembly pieces to direct the assembly process, for Golden-gate assembly, the present invention uses cohesive (generally 4 bp) single stranded overhangs, resulting from type IIs endonuclease digests. Similar to the present invention's checking for incompatible sequence homology termini when designing for SLIC/Gibson/CPEC, the present invention checks to make sure that Golden-gate assembly designs lack overhangs that are either self-incompatible (i.e., palindromic/self cohesive) or are cross-complementary (i.e., anneal with more than one (the desired) overhang)), as this would lead to off-target assembly products.

In an exemplary embodiment, the present invention utilizes the Primer3 primer design program in the oligo design process, using design parameters (such as the target Tm) defined in the parameters file received by the present invention. In an exemplary embodiment, the present invention designs the following two types of primers, (1) "pure" primers that anneal perfectly to the template sequence and (2) a 5' type IIs endonuclease site followed by a Golden-gate overhang, followed by the identical sequence of the corresponding "pure" primer.

Analogous to the present invention's utilizing the annealing Tm of two SLIC/Gibson/CPEC homology sequences to gauge the extent of their incompatibility, the present invention judges the extent of Golden-gate overhang (self-)incompatibility by the number of complementary base pairs shared between the two overhangs. In an exemplary embodiment, the maximum number of base-pair matches that the present invention allows between two overhangs that are not intended to be assembled together is determined by the parameters file received by the present invention. In a particular embodiment, the present invention allows at most 2 of the 4 overhang bp to be complementary.

If BsaI (or another selected type IIs endonuclease recognition sites were present within the DNA fragments to assemble (not only at the assembly piece termini), assembly could still occur (since the digest/ligation is a reversible-process), but the efficiency would be decreased. In an exemplary embodiment, the present invention reports a warning if these sites are encountered in the final assembled vector.

When selecting a set of Golden-gate overhangs for the assembly piece junctions (which is equivalent to selecting the set of relative overhang positions), the present invention exhaustively searches through all possible combinations of available overhangs for the assembly junctions and selects the set of overhangs (1) that are compatible with themselves and each other, and (2) that are as neutral as possible. The overhang search space (about the assembly junction) would be largely constrained by the maximum oligo size, as non-neutral relative overhang positions result in embedding additional sequence within one of the two affected oligos.

Occasionally (usually only if there are many Golden-gate junctions and the sequence regions around the junctions from which to select overhangs are highly constrained), it could be possible that the present invention could not find a set of overhangs that are compatible with themselves and with each other. In that case, in an exemplary embodiment, the present invention introduces additional scar base-pairs at one or more assembly junctions, to increase the number and diversity of the overhangs from which to select. In an exemplary embodiment, the present invention uses a particular overhang for a given Golden-gate assembly junction (by setting the relative overhang position for the junction in the target part order list file), although this would constrain the overhang selection process and could increase that chances that the present invention is unable to find a compatible set of Golden-gate overhangs.

This brings about the question of why forcibly setting a relative overhang position for Golden-gate assembly might be useful. The most common reasons to set an overhang position are (1) to be able to reuse a DNA oligo primer from a previous Golden-gate assembly (whose embedded type IIs endonuclease recognition site position determines the resulting overhang sequence) to re-amplify a part, and (2) to generate combinatorial Golden-gate libraries, where it is essential that all parts in a given combinatorial bin have the same flanking overhang termini.

In order to achieve scar-less DNA assemblies, when the present invention designs a combinatorial Golden-gate assembly, the present invention constrains the overhang search space about a given combinatorial assembly junction on the 5' side of the junction by the first (3'-most) non-identical (amongst the parts in the 5' bin) base pair, and similarly on the 3' side of the junction by the first (5'-most) non-identical (amongst the parts in the 3' bin) base pair. Note that ambiguous base pairs (such as 'N'), even if uniform at a given sequence position throughout the parts in a combinatorial bin, are considered to be non-identical sequence positions. The more sequence identity the parts in a bin have at their termini, the less constrained the overhang selection process will be. If the number of identical base pairs adjacent to or spanning the junction is not at least the length of the Golden-gate overhang, a scar-less assembly for the entire combinatorial library will not be possible, and the present invention would not be able to complete the design process. In this case, in an exemplary embodiment, the present invention adds a scar to one or more of the constructs, by inserting an identical base pair to all of the parts at the troublesome assembly junction, or alternatively preserving the parts' lengths, by (silently) mutating a base pair position of a subset of the parts to achieve a singular identity at that sequence position, effectively expanding the identical sequence span.

In an exemplary embodiment, another option that is particularly useful when designing combinatorial assemblies with the present invention is the use of direct synthesis firewalls. In an exemplary embodiment, the present invention first generates a template assembly to design all of the overhangs, and then the present invention uses the standard (single-construct) Golden-gate design process for each of the instances within the combinatorial library, thereby forcibly setting the overhang positions based on the results from the template assembly design. Since the present invention performs a cost-effective analysis for the use of direct DNA synthesis vs. PCR, etc., it could be the case that directly synthesizing two parts (in two contiguous combinatorial bins) together is less costly than performing the PCR of the two parts separately. Note that if this were the case, the combinatorial assembly benefit of keeping the parts separate would be lost. In an exemplary embodiment, the cost-effective calculation of the present invention is based on generating a single construct. In an exemplary embodiment, the cost-effective calculation of the present invention amortizes the initial cost of the oligos required for PCR over the construction cost of the entire library. In an exemplary embodiment, the present invention enforces a direct synthesis firewall between the two contiguous parts, which effectively prevents the present invention from suggesting to directly synthesize the two parts together, although the two parts could still be directly synthesized separately.

In the case of Golden-gate assembly, the main disadvantage of restriction digest backbone linearization is that it would require a Golden-gate specific entry vector with prescribed Golden-gate overhangs (which could greatly constrain the Golden-gate assembly design process).

Design Specification Rules

When designing combinatorial assemblies with the present invention, the present invention allows for the setting of design specification rules that (1) limit the total number of times a given part appears in a given assembly, (2) whether two given parts should not appear together in the same assembly, or (3) whether two given parts should only appear together in the same assembly.

Condensing Multiple Assembly Designs

In an exemplary embodiment, the present invention aggregates multiple assembly designs into a single assembly file. This is extremely useful for combinatorial library assembly, where the same direct DNA synthesis fragment or PCR product is used multiple times, but only needs to be generated once. It is also a very powerful way to condense multiple independent assemblies into the same assembly design file outputted by the present invention, which is an important step towards executing all of the assemblies in parallel in the same set of 96-well format plates.

General

For a recent review of currently available BioCAD tools, please see MacDonald[11].

SLIC/Gibson/CPEC

There are two situations that will potentially be problematic for SLIC/Gibson/CPEC assembly. First, sequence repeats, or highly homologous sequences at the termini of assembly pieces could be problematic for such assembly. It may be desirable to include a given part more than once in the same assembly (e.g., a repeated terminator or promoter). However, (aside from decreasing the physical stability of the resulting construct (via in vivo recombination processes)) these sequence repeats can be debilitating for the SLIC/Gibson/CPEC assembly methods, and should be avoided where possible. In an exemplary embodiment, the present invention uses BioCAD tools to identify parts with similar function but disparate DNA sequence (e.g., two sequences encoding the same protein with different cordons). If the repeated sequences are not located at the termini of the assembly pieces, they might not significantly affect SLIC or Gibson assembly, but they would be problematic for CPEC assembly. In certain situations, the present invention performs the assembly with the Golden-gate method, which is not as affected by sequence repeats. In an exemplary embodiment, the present invention performs highly homologous sequence detection so as to automatically issue an alert of potential problems when designing DNA assemblies, obviating the need to subsequently check with a separate tool.

Second, assembly piece termini with stable secondary structure could be problematic for such assembly. If the terminus of an assembly piece has very stable secondary structure (which can be assessed via the DINA Melt Quaffed server, or other related software), as would be anticipated for a terminator, it would not be able to base-pair/anneal with the neighboring assembly piece, and thus inhibit assembly. In an exemplary embodiment, the present invention adds sufficient flanking sequences so that the problematic section with secondary structure is no longer at the terminus. In certain situations, the present invention performs the assembly with the Golden-gate method, which is not as affected by termini with stable secondary structure. In an exemplary embodiment, the present invention performs secondary structure prediction so as to automatically alert the user to these potential problems when designing DNA assemblies, obviating the need to subsequently check with a separate tool.

For other designs, the particular rank-ordering of constraint relief may have a more significant impact. Over time, given an accumulated data set of PCR successes and failures, it would be possible to objectively analyze the relationship between relaxed constraint type and PCR or SLIC/Gibson/CPEC assembly failure rate.

Golden-Gate

There is one situation that will potentially be problematic for Golden-gate assembly. Namely, BsaI (or other selected type IIs endonuclease) recognition sites being present within the DNA fragments to assemble (not only at the assembly piece termini) would be problematic for such assembly. In this instance, in an exemplary embodiment, the present invention generates (silent) point mutations to disrupt these sites, where the site sequence is defined in the parameters file received by the present invention. Even with the undesired BsaI sites present, assembly may still occur (since the digest/ligation is a reversible-process), but the efficiency will be decreased.

BioBrick Compatible Assembly

If the resulting construct is desired to be BioBrick compatible, in an exemplary embodiment, the present invention removes any undesired BioBrick sites, by generating (silent) point mutations to disrupt these sites.

Further Example

The invention will be described in greater detail by way of a further specific example. The following example is offered for illustrative purposes, and is intended neither to limit nor define the invention in any manner.

Algorithm S5

In an exemplary embodiment, the present invention could closely approximate the optimal distribution of PCR reactions in multi-well plates across thermocycler block annealing temperature zone gradient(s) via Algorithm S5. Depending on the design of a given DNA assembly process, PCR may be required to generate (some of) the assembly pieces. While primer and flanking homology sequence design attempt to constrain melting temperature to a narrow acceptable range where possible, extreme % GC template composition may skew the resulting temperatures to well below (AT-rich) or above (GC-rich) the targeted optimum. Most modern thermocyclers feature standardized multi-well format blocks, and some (such as the Applied Biosystems Veriti Thermal Cycler employed in this study) now feature temperature gradients with individually controllable annealing temperature zones.

Algorithm S5 takes as input a set of PCR reactions with target annealing temperatures, taken here to be the minimum of the forward and reverse primer melting temperatures +2° C., and optimizes the annealing temperature zones of the thermocycler block(s) and the distribution of the PCR reactions (in multi-well plates) across the zones so as to minimize the objective function, namely the summed difference squared between the targeted annealing temperatures of the PCR reactions and the actual annealing temperatures of the thermocycler zones in which they are placed (as shown in Figure S5E). Algorithm S5 exploits a Monte-Carlo simulated annealing approach to converge upon the optimal distribution. Simulated annealing is a classical computational technique to find global minima in discrete search spaces with complicated energy landscapes.

This approach is well suited to the optimization problem addressed by Algorithm S5 because the search space (the placement of each PCR reaction in its own well, and the annealing temperature of each zone) is discrete, and there is a complicated relationship between zone temperatures, PCR reaction placements, and the objective function to be minimized.

Figure 32:
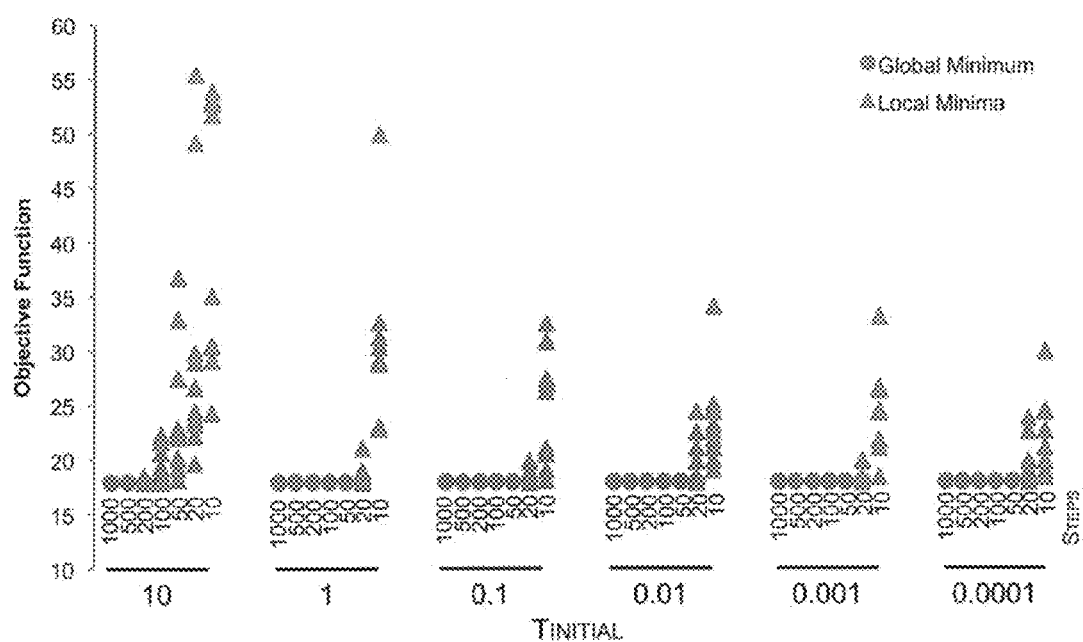
FIG. 32 shows data in accordance with the present invention.

FIG. 32 depicts the convergence of Algorithm S5 as a function of MAXMCSTEPSPERZONE and MCTEMPERATUREINITIAL. Algorithm S5 was run 10 times for each choice of MAXMCSTEPSPERZONE (here "STEPS") and MCTEMPERATUREINITIAL (here "TINITIAL"), with all other parameters set to their respective j5 default values. The best objective function encountered for each run is plotted with either a red triangle indicating a non-global minima, or a blue circle indicating the global minimum. All runs with 50 or more MAXMCSTEPSPERZONE (with the exception of MCTEMPERATUREINITIAL=10, which required 500 or more MAXMCSTEPSPERZONE) identified the global minimum. The default parameters for j5 are MCTEMPERATUREINITIAL=0.1 and MAXMCSTEPSPERZONE=1000.

REFERENCES

1. Ellis T, Adie T, Baldwin G S, "DNA assembly for synthetic biology: from parts to pathways and beyond", *Integra Boil* (Comb). 2011 Jan. 19.
2. Reshma P Shetty, Drew Endy, Thomas F. Knight, Jr., "Engineering BioBrick vectors from BioBrick parts", *J Biol Eng.* 2008; 2: 5.
3. J. Christopher Anderson, John E. Dueber, Mariana Leguia, Gabriel C. Wu, Jonathan A. Goler, Adam P. Arkin, Jay D. Keasling, "BglBricks: A flexible standard for biological part assembly", *J Biol Eng.* 2010; 4: 1.
4. Douglas Densmore, Timothy H. C. Hsiau, Joshua T. Kittleson, Will DeLoache, Christopher Batten, J. Christopher Anderson, "Algorithms for automated DNA assembly", *Nucl. Acids Res.* (2010).
5. Mamie Z. Li, Stephen J. Hedge, "Harnessing homologous recombination in vitro to generate recombinant DNA via RAC", *Nature Methods*—4, 251-256 (2007).
6. Daniel G. Gibson, Lei Young, Ray-Yuan Chuang, J. Craig Venter, Clyde A. Hutchison, Hamilton O, Smith, "Enzymatic assembly of DNA molecules up to several hundred kilobases", *Nature Methods* 6, 343-345 (2009).
7. Quan J., Tian J., "Circular Polymerase Extension Cloning of Complex Gene Libraries and Pathways", *PLoS ONE* 2009 4(7).
8. Ramon A., Smith, H O., "Single-step linker-based combinatorial assembly of promoter and gene cassettes for pathway engineering", *Biotechnol Lett.* 2010 Nov. 24.
9. Engler C., Kandzia R., Marillonnet S., "A One Pot, One Step, Precision Cloning Method with High Throughput Capability", *PLoS ONE* 2008 3(11).
10. Engler C., Gruetzner R., Kandzia R., Marillonnet S., "Golden Gate Shuffling: A One-Pot DNA Shuffling Method Based on Type Its Restriction Enzymes", *PLoS ONE* 2009 4(5).
11. Macdonald J T, Barnes C, Kitney R I, Freemont P S, Stan G B, "Computational design approaches and tools for synthetic biology", *Integr Biol* (Camb). 2011 Jan. 24.
12. Shao Z., Zhao H., Zhao H., "DNA assembler, an in vivo genetic method for rapid construction of biochemical pathways", *Nucleic Acids Res.* 2009 February; 37(2).

CONCLUSION

It is to be understood that the above description and examples are intended to be illustrative and not restrictive. Many embodiments will be apparent to those of skill in the art upon reading the above description and examples. The scope of the invention should, therefore, be determined not with reference to the above description and examples, but should instead be determined with reference to the appended claims, along with the full scope of equivalents to which such claims are entitled. The disclosures of all articles and references, including patent applications and publications, are incorporated herein by reference for all purposes.

What is claimed is:

1. A method of designing the parts and protocol for assembling a DNA construct via a synthetic method utilizing flanking overlap sequences, said method comprising:

receiving a list of DNA sequence fragments comprising the parts to be assembled together and an order in which to assemble said DNA sequence fragments to form said construct;

determining with a bioCAD computer system flanking overlap sequences for said fragments, wherein said determining comprises consideration of a plurality of flanking overlap sequences, where said plurality comprises flanking overlap sequences having different lengths and nucleotide sequence to determine the melting temperatures (Tm) of each of said different flanking overlap sequences with the corresponding flanking overlap sequence on an assembly piece that will be a neighboring assembly piece in the DNA sequence fragments to be assembled, and selecting from said plurality particular flanking overlap sequences for each assembly piece, where said flanking overlap sequences each have a nucleotide sequence, melting temperature, and number of base pairs so that said assembly pieces will assemble to each other in the sequence order required to form said construct;

designing with said bioCAD computer system oligonucleotide primers for the PCR amplification of said fragments with flanking overlap sequences where determined;

creating a plan and protocol for the preparation of said fragments with flanking overlap sequences and/or the assembly of said fragments to form said construct; and performing PCR and/or SOE utilizing said primers to generate the DNA sequence fragments comprising said parts with flanking overlap sequences.

2. The method of claim 1 wherein the receiving further comprises searching for at least one DNA sequence within a collection of physically existing DNA sequences in a registry of biological parts and/or a local collection of DNA sequences.

3. The method of claim 1 wherein said determining further comprises ensuring that the flanking overlap sequences of the DNA sequence fragments do not have stable single-stranded DNA secondary structure at a temperature at which said assembly pieces assemble to each other to form said construct.

4. The method of claim 1 wherein the receiving comprises receiving the list of DNA sequence fragments wherein at least one of the DNA sequence fragments has been physically instantiated.

5. The method of claim 1 wherein the receiving comprises receiving the list of DNA sequence fragments wherein at least one of the DNA sequence fragments has not been physically instantiated.

6. The method of claim 1 wherein the receiving comprises receiving at least one instruction to use at least one of the DNA sequence fragments at more than one place in the order.

7. The method of claim 1 wherein the creating comprises planning the flanking overlap sequences with respect to assembling a combinatorial library of constructs without scars.

8. The method of claim 7, further comprising assembling said DNA sequence fragments into a combinatorial construct library using an assembly method selected from the group consisting of SLIC, Gibson, CPEC, and SLiCE.

9. The method of claim 1 wherein the creating comprises creating the plan to add flanking DNA fragments containing the flanking overlap sequences via splicing by overlap extension (SOE) to each of said oligonucleotide primers after the primers have been incorporated at the ends of a product of a polymerase chain reaction.

10. The method of claim 1 further comprising determining an assembly strategy for each of the DNA sequence fragments that minimizes cost of fragment preparation.

11. The method of claim 10 wherein the designing comprises designing said oligonucleotide primers to provide the DNA sequence fragments at a minimum cost.

12. The method of claim 10 wherein the creating comprises creating a protocol that minimizes cost of construction and assembly of said construct.

13. The method of claim 1 further comprising checking the protocol against oligonucleotide mis-priming and against assembly piece incompatibility events.

14. The method of claim 13 wherein the checking further comprises providing a hierarchical assembly protocol, wherein the hierarchical assembly protocol is designed to mitigate the assembly piece incompatibility events.

15. The method of claim 13 further comprising outputting an experimental protocol of the DNA assembly based on the checked plan.

16. The method of claim 15 wherein the outputting comprises outputting the experimental protocol, wherein the protocol dictates the spatial arrangement of polymerase chain reactions (PCRs) to implement the DNA assembly on a multi-well thermo-cycler block with an annealing temperature gradient.

17. The method of claim 1 further comprising:
checking the plan; and
issuing a warning if at least one significant DNA sequence repeat exists in the plan.

18. The method of claim 1 further comprising outputting an experimental protocol for the DNA assembly based on the plan.

19. The method of claim 18 wherein the protocol dictates how polymerase chain reactions (PCRs) to implement the DNA assembly are to be spatially arranged on a multi-well thermo-cycler block with an annealing temperature gradient.

20. The method of claim 1 further comprising outputting a DNA sequence file of the DNA assembly based on the plan.

21. The method of claim 20 wherein the outputting further comprises providing annotations of features within the DNA assembly.

22. The method of claim 1, wherein said parts and protocol are for an assembly method selected from the group consisting of SLIC, Gibson, CPEC, and SLiCE.

23. The method of claim 1, further comprising assembling said DNA sequence fragments into said construct using an assembly method selected from the group consisting of SLIC, Gibson, CPEC, and SLiCE.

24. The method of claim 1, wherein said determining comprises selecting flanking sequences having a melting temperature and number of base pairs so that said assembly pieces will assemble to each other to form said construct where said construct will be assembled from more than two DNA sequence fragments.

25. A method of designing the parts and protocol for assembling a DNA construct via a synthetic method utilizing flanking overlap sequences, said method comprising:
receiving a list of DNA sequence fragments comprising the parts to be assembled together and an order in which to assemble said DNA sequence fragments;
determining with a bioCAD computer system flanking overlap sequences for said fragments, wherein said determining comprises consideration of a plurality of flanking overlap sequences, where said plurality comprises flanking overlap sequences having different lengths and nucleotide sequence to determine the melting temperatures (Tm) of each of said different flanking overlap sequences with the corresponding flanking overlap sequence on an assembly piece that will be a neighboring assembly piece in the DNA sequence fragments to be assembled, and selecting from said plurality particular flanking overlap sequences for each assembly piece, where said flanking overlap sequences each have a nucleotide sequence, melting temperature, and number of base pairs so that said assembly pieces will assemble to each other in the sequence order required to form said construct;
utilizing said computer system to design direct synthesis pieces and oligonucleotide primers for the preparation of the DNA sequence fragments with said flanking overlap sequences;
creating a plan and/or protocol for the preparation of said fragments with flanking overlap sequences and/or the assembly of said fragments; and
executing PCR utilizing said primers and providing direct synthesis to generate the DNA sequence fragments comprising said parts with the flanking overlap sequences.

26. The method of claim 25 wherein the receiving further comprises searching for at least one DNA sequence within a collection of physically existing DNA sequences in a registry of biological parts and/or a local collection of DNA sequences.

27. The method of claim 25 wherein said determining further comprises ensuring that the ends of the DNA sequence fragments do not have stable single-stranded DNA secondary structure at a temperature at which said assembly pieces assemble to each other to form said construct.

28. The method of claim 25 wherein the receiving comprises receiving the list of DNA sequence fragments wherein at least one of the DNA sequence fragments has been physically instantiated.

29. The method of claim 25 wherein the receiving comprises receiving the list of DNA sequence fragments wherein at least one of the DNA sequence fragments has not been physically instantiated.

30. The method of claim 25 wherein the receiving comprises receiving at least one instruction to use at least one of the DNA sequence fragments at more than one place in the order.

31. The method of claim 25 wherein the creating comprises planning the flanking overlap sequences with respect to assembling a combinatorial library of DNA constructs without scars.

32. The method of claim 31, further comprising assembling said DNA sequence fragments into a combinatorial construct library using an assembly method selected from the group consisting of SLIC, Gibson, CPEC, and SLiCE.

33. The method of claim 25 wherein the creating comprises creating the plan to add flanking DNA fragments containing the flanking overlap sequences via splicing by overlap extension (SOE) to each of said oligonucleotide primers after the primers have been incorporated at the ends of a product of a polymerase chain reaction.

34. The method of claim 25 further comprising determining an assembly strategy for each of the DNA sequence fragments that minimizes cost of fragment preparation.

35. The method of claim 34 wherein the designing comprises designing the direct synthesis pieces and said oligonucleotide primers to provide the DNA sequence fragments at a minimum cost.

36. The method of claim 34 wherein the creating comprises creating a protocol that minimizes cost of construction and assembly of said construct.

37. The method of claim 25 further comprising checking the protocol against oligonucleotide mis-priming and against assembly piece incompatibility events.

38. The method of claim 37 wherein the checking further comprises providing a hierarchical assembly protocol, wherein the hierarchical assembly protocol is designed to mitigate the assembly piece incompatibility events.

39. The method of claim 37 further comprising outputting an experimental protocol and a DNA sequence file of the DNA assembly based on the checked plan.

40. The method of claim 39 wherein the outputting comprises outputting the experimental protocol, wherein the protocol dictates the spatial arrangement of polymerase chain reactions (PCRs) to implement the DNA assembly on a multi-well thermo-cycler block with an annealing temperature gradient.

41. The method of claim 25 further comprising:
checking the plan; and
issuing a warning if at least one significant DNA sequence repeat exists in the plan.

42. The method of claim 25 further comprising outputting an experimental protocol for the DNA assembly based on the plan.

43. The method of claim 42 wherein the outputting comprises outputting the experimental protocol, wherein the protocol dictates how polymerase chain reactions (PCRs) to implement the DNA assembly are to be spatially arranged on a multi-well thermo-cycler block with an annealing temperature gradient.

44. The method of claim 25 further comprising outputting a DNA sequence file of the DNA assembly based on the plan.

45. The method of claim 44 wherein the outputting further comprises providing annotations of features within the DNA assembly.

46. The method of claim 25, wherein said parts and protocol are for an assembly method selected from the group consisting of SLIC, Gibson, CPEC, and SLiCE.

47. The method of claim 25, further comprising assembling said DNA sequence fragments into said construct using an assembly method selected from the group consisting of SLIC, Gibson, CPEC, and SLiCE.

48. The method of claim 25, wherein said determining comprises selecting flanking sequences having a melting temperature and number of base pairs so that said assembly pieces will assemble to each other to form said construct where said construct will be assembled from more than two DNA sequence fragments.

49. A method of designing the parts and protocol for assembling a DNA construct via a synthetic method utilizing flanking overlap sequences, said method comprising:
receiving a list of DNA sequence fragments comprising the parts to be assembled together and an order in which to assemble said DNA sequence fragments;
determining with a bioCAD computer system flanking overlap sequences for said fragments, wherein said determining comprises consideration of a plurality of flanking overlap sequences, where said plurality comprises flanking overlap sequences having different lengths and nucleotide sequence to determine the melting temperatures (Tm) of each of said different flanking overlap sequences with the corresponding flanking overlap sequence on an assembly piece that will be a neighboring assembly piece in the DNA sequence fragments to be assembled, and selecting from said plurality particular flanking overlap sequences for each assembly piece, where said flanking overlap sequences each have a nucleotide sequence, melting temperature, and number of base pairs so that said assembly pieces will assemble to each other in the sequence order required to form said construct;
utilizing said computer system to design direct synthesis pieces for the DNA sequence fragments;
creating a plan and/or protocol for the preparation of the direct synthesis pieces;
providing the direct synthesis pieces; and performing PCR and/or SOE utilizing said primers to generate the DNA sequence fragments comprising said parts with flanking overlap sequences; or executing PCR utilizing said primers and providing direct synthesis to generate the DNA sequence fragments comprising said parts with flanking overlap sequences.

50. The method of claim 49 wherein the receiving further comprises searching for at least one DNA sequence within a collection of physically existing DNA sequences in a registry of biological parts and/or a local collection of DNA sequences.

51. The method of claim 49 wherein said determining further comprises ensuring that the ends of the DNA sequence fragments do not have stable single-stranded DNA secondary structure at a temperature at which said assembly pieces assemble to each other to form said construct.

52. The method of claim 49 wherein the receiving comprises receiving the list of DNA sequence fragments wherein at least one of the DNA sequence fragments has been physically instantiated.

53. The method of claim 49 wherein the receiving comprises receiving the list of DNA sequence fragments wherein at least one of the DNA sequence fragments has not been physically instantiated.

54. The method of claim 49 wherein the receiving comprises receiving at least one instruction to use at least one of the DNA sequence fragments at more than one place in the order.

55. The method of claim 49 wherein the creating comprises planning the flanking overlap sequences to assemble a combinatorial library of DNA constructs.

56. The method of claim 55, further comprising assembling said DNA sequence fragments into a combinatorial construct library using an assembly method selected from the group consisting of SLIC, Gibson, CPEC, and SLiCE.

57. The method of claim 49 wherein the creating comprises creating the plan to add flanking DNA fragments containing the flanking overlap sequences via said direct synthesis.

58. The method of claim 49 further comprising determining an assembly strategy for each of the DNA sequence fragments that minimizes cost of fragment preparation.

59. The method of claim 58 wherein the designing comprises designing the direct synthesis pieces to provide the DNA sequence fragments at a minimum cost.

60. The method of claim 58 wherein the creating comprises creating a protocol that minimizes cost of construction and assembly of said construct.

61. The method of claim 49 further comprising checking the plan against assembly piece incompatibility events.

62. The method of claim 61 wherein the checking further comprises providing a hierarchical assembly protocol, wherein the hierarchical assembly protocol is designed to mitigate the assembly piece incompatibility events.

63. The method of claim 61 further comprising outputting an experimental protocol and a DNA sequence file of the DNA assembly based on the checked plan.

64. The method of claim 49 further comprising:
checking the plan; and
issuing a warning if at least one significant DNA sequence repeat exists in the plan.

65. The method of claim 49 further comprising outputting an experimental protocol for the DNA assembly based on the plan.

66. The method of claim 49 further comprising outputting a DNA sequence file of the DNA assembly based on the plan.

67. The method of claim 66 wherein the outputting further comprises providing annotations of features within the DNA assembly.

68. The method of claim 49, wherein said determining comprises selecting flanking sequences having a melting temperature and number of base pairs so that said assembly pieces will assemble to each other to form said construct where said construct will be assembled from more than two DNA sequence fragments.

69. A method of designing the parts and protocol for assembling a DNA construct via a synthetic method utilizing flanking overlap sequences, said method comprising:
receiving a list of DNA sequence fragments comprising the parts to be assembled together and an order in which to assemble said DNA sequence fragments;
determining with a bioCAD computer system flanking overlap sequences for said fragments, wherein said determining comprises consideration of a plurality of flanking overlap sequences, where said plurality comprises flanking overlap sequences having different lengths and nucleotide sequence to determine the melting temperatures (Tm) of each of said different flanking overlap sequences with the corresponding flanking overlap sequence on an assembly piece that will be a neighboring assembly piece in the DNA sequence fragments to be assembled, and selecting from said plurality particular flanking overlap sequences for each assembly piece, where said flanking overlap sequences each have a nucleotide sequence, melting temperature, and number of base pairs so that said assembly pieces will assemble to each other in the sequence order required to form said construct;
designing with said bioCAD computer system said oligonucleotide primers for the PCR amplification of said fragments with flanking overlap sequences where determined, and/or utilizing a said computer system to design direct synthesis pieces for the DNA sequence fragments with flanking overlap sequences where determined;
creating a plan and protocol for the preparation of said fragments with flanking overlap sequences and/or the assembly of said fragments;
outputting said plan and protocol to a user; and performing PCR and/or SOE utilizing said primers to generate the DNA sequence fragments comprising said parts with flanking overlap sequences; or executing PCR utilizing said primers and providing direct synthesis to generate the DNA sequence fragments comprising said parts with flanking overlap sequences.

70. The method of claim 69 wherein the receiving further comprises searching for at least one DNA sequence within a collection of physically existing DNA sequences in a registry of biological parts and/or a local collection of DNA sequences.

71. The method of claim 69 wherein the receiving comprises receiving the list of DNA sequence fragments wherein at least one of the DNA sequence fragments has been physically instantiated.

72. The method of claim 71, wherein said method further comprises providing the direct synthesis pieces.

73. The method of claim 69, wherein the creating comprises planning the flanking overlap sequences with respect to assembling a combinatorial library of constructs without scars.

74. The method of claim 69, wherein said parts and protocol are for an assembly method selected from the group consisting of SLIC, Gibson, CPEC, and SLiCE.

75. The method of claim 69, further comprising assembling said DNA sequence fragments into said construct using an assembly method selected from the group consisting of SLIC, Gibson, CPEC, and SLiCE.

76. The method of claim 69, wherein said determining comprises selecting flanking sequences having a melting temperature and number of base pairs so that said assembly pieces will assemble to each other to form said construct where said construct will be assembled from more than two DNA sequence fragments.

* * * * *

UNITED STATES PATENT AND TRADEMARK OFFICE
CERTIFICATE OF CORRECTION

PATENT NO. : 9,361,427 B2  
APPLICATION NO. : 13/364285  
DATED : June 7, 2016  
INVENTOR(S) : Nathan J. Hillson Page 1 of 1

It is certified that error appears in the above-identified patent and that said Letters Patent is hereby corrected as shown below:

In the Claims

Claim 49, Column 48, Line 52:
Please change "and/or SOE utilizing said primers to generate the DNA" to --and/or SOE utilizing primers to generate the DNA--

Claim 69, Column 50, Line 19:
Please change "designing with said bioCAD computer system said oligonucleotide primers for the PCR amplification of said" to --designing with said bioCAD computer system oligonucleotide primers for the PCR amplification of said--

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 44

<210> SEQ ID NO 1
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 1
cgcgccttcc                                                              10

<210> SEQ ID NO 2
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 2
ggactcaaca                                                              10

<210> SEQ ID NO 3
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 3
cgcaaaaaac                                                              10

<210> SEQ ID NO 4
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 4
cctgtggcgc                                                              10

<210> SEQ ID NO 5
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 5
aattcaaagg                                                              10

<210> SEQ ID NO 6
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 6
tgatggtccg                                                              10

<210> SEQ ID NO 7
<211> LENGTH: 10
<212> TYPE: DNA
<213> ORGANISM: Artificial Sequence

```
<220> FEATURE:
<223> OTHER INFORMATION: 5' end of an exemplary biological part

<400> SEQUENCE: 7
aaaaaaaaac                                                          10

<210> SEQ ID NO 8
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 8
aattcaaagg                                                          10

<210> SEQ ID NO 9
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 9
ggactcaaca                                                          10

<210> SEQ ID NO 10
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 10
atagtgctgt                                                          10

<210> SEQ ID NO 11
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 11
atccttaatt                                                          10

<210> SEQ ID NO 12
<211> LENGTH: 9
<212> TYPE: DNA
<213> ORGANISM: Artificial Sequence
<220> FEATURE:
<223> OTHER INFORMATION: 5' end of an exemplary biological part

<400> SEQUENCE: 12 ccggcgcca                                                            9

<210> SEQ ID NO 13
<211> LENGTH: 9
<212> TYPE: DNA
<213> ORGANISM: Artificial Sequence
<220> FEATURE:
<223> OTHER INFORMATION: 5' end of an exemplary biological part

<400> SEQUENCE: 13 cctgtggcg                                                            9
```

```
<210> SEQ ID NO 14
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 14
ggggtttttt                                                                  10

<210> SEQ ID NO 15
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 15
tgaaattgtt                                                                  10

<210> SEQ ID NO 16
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 16
cttcctttga                                                                  10

<210> SEQ ID NO 17
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 17
aattcaaagg                                                                  10

<210> SEQ ID NO 18
<211> LENGTH: 9
<212> TYPE: DNA
<213> ORGANISM: Artificial Sequence
<220> FEATURE:
<223> OTHER INFORMATION: 5' end of an exemplary biological part

<400> SEQUENCE: 18 tgtgagcgg                                                                    9

<210> SEQ ID NO 19
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 19
tggatcataa                                                                  10

<210> SEQ ID NO 20
<211> LENGTH: 10
<212> TYPE: DNA
<213> ORGANISM: Artificial Sequence
<220> FEATURE:
<223> OTHER INFORMATION: 5' end of an exemplary biological part
```

```
<400> SEQUENCE: 20
gttgttgtac                                                                10

<210> SEQ ID NO 21
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 21
tgatggtccg                                                                10

<210> SEQ ID NO 22
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 22
aagttatgat                                                                10

<210> SEQ ID NO 23
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 23
agatccttag                                                                10

<210> SEQ ID NO 24
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 24
ccggcgccca                                                                10

<210> SEQ ID NO 25
<211> LENGTH: 9
<212> TYPE: DNA
<213> ORGANISM: Artificial Sequence
<220> FEATURE:
<223> OTHER INFORMATION: 5' end of an exemplary biological part

<400> SEQUENCE: 25 cctgtggcg                                                                  9

<210> SEQ ID NO 26
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 26
cggggttttt                                                                10
```

```
<210> SEQ ID NO 27
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 27
tgaaattgtt                                                          10

<210> SEQ ID NO 28
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 28
cttcctttga                                                          10

<210> SEQ ID NO 29
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 29
aattcaaagg                                                          10

<210> SEQ ID NO 30
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 30
tgtgagcgga                                                          10

<210> SEQ ID NO 31
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 31
ccagtccttg                                                          10

<210> SEQ ID NO 32
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 32
gatgctgttt                                                          10

<210> SEQ ID NO 33
<211> LENGTH: 10
<212> TYPE: DNA
<213> ORGANISM: Artificial Sequence
<220> FEATURE:
<223> OTHER INFORMATION: 5' end of an exemplary biological part
```

```
<400> SEQUENCE: 33
ggactcaaca                                                          10

<210> SEQ ID NO 34
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 34
cctgtggcgc                                                          10

<210> SEQ ID NO 35
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 35
aattcaaagg                                                          10

<210> SEQ ID NO 36
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 36
tgatggtccg                                                          10

<210> SEQ ID NO 37
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 37
cctgtggcgc                                                          10

<210> SEQ ID NO 38
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 38
aattcaaagg                                                          10

<210> SEQ ID NO 39
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 39
atagtgctgt                                                          10
```

-continued

```
<210> SEQ ID NO 40
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 40
ggggtttttt                                                              10

<210> SEQ ID NO 41
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 41
tgtgagcgga                                                              10

<210> SEQ ID NO 42
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 42
aagttatgat                                                              10

<210> SEQ ID NO 43
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 43
cggggttttt                                                              10

<210> SEQ ID NO 44
<211> LENGTH: 10
<212> TYPE: DNA
<213> ORGANISM: Artificial Sequence
<220> FEATURE:
<223> OTHER INFORMATION: 5' end of an exemplary biological part

<400> SEQUENCE: 44
tgtgagcgga                                                              10
```